(12) United States Patent
Davies et al.

(10) Patent No.: US 8,217,148 B2
(45) Date of Patent: Jul. 10, 2012

(54) C-MET ANTIBODIES

(75) Inventors: Julian Davies, La Jolla, CA (US); Ling Liu, Carmel, IN (US); Jirong Lu, Carmel, IN (US); Peter Edward Vaillancourt, Del Mar, CA (US); Mark Andrew Wortinger, Greenwood, IN (US); Wei Zeng, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 282 days.

(21) Appl. No.: 12/620,617

(22) Filed: Nov. 18, 2009

(65) Prior Publication Data

US 2010/0129369 A1 May 27, 2010

Related U.S. Application Data

(60) Provisional application No. 61/116,825, filed on Nov. 21, 2008, provisional application No. 61/219,903, filed on Jun. 24, 2009.

(51) Int. Cl.
*C07K 16/00* (2006.01)
(52) U.S. Cl. .................................. 530/387.1; 530/388.8
(58) Field of Classification Search ........................ None
See application file for complete search history.

(56) References Cited

U.S. PATENT DOCUMENTS

| | | | |
|---|---|---|---|
| 5,571,509 | A | 11/1996 | Comoglio et al. |
| 6,214,344 | B1 | 4/2001 | Schwall et al. |
| 7,494,650 | B2 | 2/2009 | Kim et al. |
| 7,556,804 | B2 | 7/2009 | Prat |
| 2008/0038256 | A1 | 2/2008 | Chung et al. |

FOREIGN PATENT DOCUMENTS

| | | |
|---|---|---|
| WO | WO 96/38557 A1 | 12/1996 |
| WO | WO 2004/072117 A2 | 8/2004 |
| WO | WO 2005/016382 A1 | 2/2005 |
| WO | WO 2005/058965 A1 | 6/2005 |
| WO | WO 2005/063816 A2 | 7/2005 |
| WO | WO 2006/015371 A2 | 2/2006 |
| WO | WO 2006/104911 A2 | 10/2006 |
| WO | WO 2007/090807 A1 | 8/2007 |
| WO | WO 2007/126799 A2 | 11/2007 |
| WO | WO 2009/007427 A2 | 1/2009 |

OTHER PUBLICATIONS

Michaud, et al., Targeting the hepatocyte growth factor receptor c-Met with neutralizing human monoclonal antibodies for the treatment of cancer, (abstract 3027), Proceedings of the American Association for Cancer Research Annual Meeting, vol. 47, pp. 712-713 (Apr. 2006).
Tseng, et al., "Preclinical efficacy of the c-Met inhibitor CE-355621 in a U87 MG mouse xenograft model evaluated by 18F-FDG small-animal PET," Journal of Nuclear Medicine: Official Publication, Society of Nuclear Medicine, vol. 49, No. 1, pp. 129-134 (Jan. 2008).
Jarvis, "Big Biotechs Take Antibody Approach to Blocking Met Receptors." Chemical & Engineering News, vol. 85, No. 34, pp. 22 (Aug. 20, 2007).
Corvaia, et al., "First Bivalent Fully Antagonistic Anti-c-Met Antibody Targeting the c-Met Receptor: I) In Vitro Mechanism of Action," (poster 835), Proceedings of the American Association for Cancer Research Annual Meeting (Denver, CO) in Apr. 20, 2009.
Goetsch, et al., First Bivalent Fully Antagonistic Anti-c-Met Antibody Targeting the c-Met Receptor: I) In Vivo Activity, poster 2792), Proceedings of the American Association for Cancer Research Annual Meeting (Denver, CO) in Apr. 20, 2009.
Liu, et al. "Targeting the c-Met signaling pathway for cancer therapy." Expert Opin. Investig. Drugs (Review) 17 (7), pp. 997-1011 (2008).
Martens, et al. "A Novel One-Armed Anti-c-Met Antibody Inhibits Glioblastoma Growth In vivo." Clin Cancer Res 2006; 12 (20) Oct. 15, 2006, pp. 6144-6152.
Van Der Horst, et al., "Discovery of Fully Human Anti-MET Monoclonal Antibodies with Antitumor Activity against Colon Caner Tumor Models In Vivo," Neoplasia, vol. 11, No. 4, pp. 355-364 (Apr. 2009).

*Primary Examiner* — Hong Sang
(74) *Attorney, Agent, or Firm* — Robert L. Sharp; Alejandro Martinez

(57) ABSTRACT

Provided are monoclonal antibodies, antigen-binding fragments thereof, and combinations of the foregoing, that bind to, and inhibit the activity of, c-Met, and that are effective in treating cancers and other diseases, disorders, or conditions where pathogenesis is mediated by c-Met.

19 Claims, No Drawings

SEQUENCE LISTING

```
<160> NUMBER OF SEQ ID NOS: 97

<210> SEQ ID NO 1
<211> LENGTH: 108
<212> TYPE: PRT
<213> ORGANISM: Artificial Sequence
```

<220> FEATURE:
<223> OTHER INFORMATION: Synthetic Construct

<400> SEQUENCE: 1

```
Glu Ile Val Leu Thr Gln Ser Pro Gly Thr Leu Ser Leu Ser Pro Gly
1               5                   10                  15
Glu Arg Ala Thr Leu Ser Cys Ser Val Ser Ser Ser Ile Ser Ser Thr
            20                  25                  30
Asn Leu His Trp Tyr Gln Gln Lys Pro Gly Gln Ala Pro Arg Leu Leu
        35                  40                  45
Ile Tyr Gly Thr Ser Tyr Leu Ala Ser Gly Ile Pro Asp Arg Phe Ser
50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Trp Ser Ser Tyr Pro
                85                  90                  95
Tyr Ser Phe Gly Gln Gly Thr Lys Leu Glu Ile Lys
            100                 105
```

<210> SEQ ID NO 2
<211> LENGTH: 108
<212> TYPE: PRT
<213> ORGANISM: Artificial Sequence
<220> FEATURE:
<223> OTHER INFORMATION: Synthetic Construct

<400> SEQUENCE: 2

```
Glu Ile Val Leu Thr Gln Ser Pro Gly Thr Leu Ser Leu Ser Pro Gly
1               5                   10                  15
Glu Arg Ala Thr Leu Ser Cys Ser Val Ser Ser Ser Ile Ser Ser Thr
            20                  25                  30
Asn Leu His Trp Tyr Gln Gln Lys Pro Gly Gln Ala Pro Arg Leu Leu
        35                  40                  45
Ile Tyr Gly Thr Ser Tyr Leu Ala Ser Gly Ile Pro Asp Arg Phe Ser
50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Trp Ser Ser Tyr Pro
                85                  90                  95
Tyr Ser Phe Gly Gln Gly Thr Lys Leu Glu Ile Lys
            100                 105
```

<210> SEQ ID NO 3
<211> LENGTH: 108
<212> TYPE: PRT
<213> ORGANISM: Artificial Sequence
<220> FEATURE:
<223> OTHER INFORMATION: Synthetic Construct

<400> SEQUENCE: 3

```
Glu Ile Val Leu Thr Gln Ser Pro Gly Thr Leu Ser Leu Ser Pro Gly
1               5                   10                  15
Glu Arg Ala Thr Leu Ser Cys Ser Val Ser Ser Ser Ile Ser Ser Thr
            20                  25                  30
Asn Leu His Trp Tyr Gln Gln Lys Pro Gly Gln Ala Pro Arg Leu Leu
        35                  40                  45
Ile Tyr Gly Thr Ser Arg Leu Arg Ser Gly Ile Pro Asp Arg Phe Ser
50                  55                  60
Gly Ser Gly Ser Gly Thr Asp Phe Thr Leu Thr Ile Ser Arg Leu Glu
```

```
                65                  70                  75                  80
Pro Glu Asp Phe Ala Val Tyr Tyr Cys Gln Gln Trp Ser Ser Tyr Pro
                    85                  90                  95
Tyr Ser Phe Gly Gln Gly Thr Lys Leu Glu Ile Lys
                100                 105

<210> SEQ ID NO 4
<211> LENGTH: 108
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Ser Ser Ile
                20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Ile Gln Tyr Ser Gly Tyr Pro
                    85                  90                  95

Leu Thr Phe Gly Gly Gly Thr Lys Val Glu Ile Lys
                100                 105

<210> SEQ ID NO 5
<211> LENGTH: 108
<212> TYPE: PRT
<213> ORGANISM: Artificial Sequence
<220> FEATURE:
<223> OTHER INFORMATION: Synthetic Construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Ser Ser Ile
                20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                    85                  90                  95

Leu Thr Phe Gly Gly Gly Thr Lys Val Glu Ile Lys
                100                 105

<210> SEQ ID NO 6
<211> LENGTH: 108
<212> TYPE: PRT
<213> ORGANISM: Artificial Sequence
<220> FEATURE:
<223> OTHER INFORMATION: Synthetic Construct

<400> SEQUENCE: 6
```

-continued

```
Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Arg Ser Ile
            20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Arg Gly Tyr Pro
                85                  90                  95

Leu Thr Phe Gly Gly Gly Thr Lys Val Glu Ile Lys
            100                 105
```

<210> SEQ ID NO 7
<211> LENGTH: 324
<212> TYPE: DNA
<213> ORGANISM: Artificial Sequence
<220> FEATURE:
<223> OTHER INFORMATION: Synthetic Construct

<400> SEQUENCE: 7

```
gaaattgtgt tgacgcagtc tccaggcacc ctgtctttgt ctccagggga aagagccacc      60
ctctcctgca gtgtcagctc aagtataagt tccaccaact acactggta ccagcagaaa      120
cctggccagg ctcccaggct cctcatctat ggcacatcct atctggcttc tggcatccca     180
gacaggttca gtggcagtgg gtctgggaca gacttcactc tcaccatcag cagactggag     240
cctgaagatt ttgcagtgta ttactgtcaa cagtggagta gttacccgta cagtttcggc     300
caagggacca agttggagat caaa                                            324
```

<210> SEQ ID NO 8
<211> LENGTH: 324
<212> TYPE: DNA
<213> ORGANISM: Artificial Sequence
<220> FEATURE:
<223> OTHER INFORMATION: Synthetic Construct

<400> SEQUENCE: 8

```
gaaattgtgt tgacgcagtc tccaggcacc ctgtctttgt ctccagggga aagagccacc      60
ctctcctgca gtgtcagctc aagtataagt tccaccaact acactggta ccagcagaaa      120
cctggccagg ctcccaggct cctcatctat ggcacatcct acctggcttc tggcatccca     180
gacaggttca gtggcagtgg gtctgggaca gacttcactc tcaccatcag cagactggag     240
cctgaagatt ttgcagtgta ttactgtcaa cagtggagta gttacccgta cagtttcggc     300
caagggacca agttggagat caaa                                            324
```

<210> SEQ ID NO 9
<211> LENGTH: 324
<212> TYPE: DNA
<213> ORGANISM: Artificial Sequence
<220> FEATURE:
<223> OTHER INFORMATION: Synthetic Construct

<400> SEQUENCE: 9

```
gaaattgtgt tgacgcagtc tccaggcacc ctgtctttgt ctccagggga aagagccacc      60
ctctcctgca gtgtcagctc aagtataagt tccaccaact acactggta ccagcagaaa      120
cctggccagg ctcccaggct cctcatctat ggcacatcca gactgagatc tggcatccca    180
```

```
gacaggttca gtggcagtgg gtctgggaca gacttcactc tcaccatcag cagactggag    240
cctgaagatt ttgcagtgta ttactgtcaa cagtggagta gttacccgta cagtttcggc    300
caagggacca agttggagat caaa                                           324

<210> SEQ ID NO 10
<211> LENGTH: 324
<212> TYPE: DNA
<213> ORGANISM: Artificial Sequence
<220> FEATURE:
<223> OTHER INFORMATION: Synthetic Construct

<400> SEQUENCE: 10
gacatccaga tgacccagtc tccatcctcc ctgtctgcat ctgtaggaga cagagtcacc    60
atcacttgca gtgtcagctc aagtgtaagt tccatttact tgcactggta tcagcagaaa   120
ccagggaaag cccctaagct cctgatctat agcacatcca acttggcttc tggagtccca   180
tcaaggttca gtggcagtgg atctgggaca gatttcactc tcaccatcag cagtctgcaa   240
cctgaagatt ttgcaactta ctactgtatt cagtacagtg ttacccgct cacgttcggc    300 ggagggacca aggtggagat caaa                                           324

<210> SEQ ID NO 11
<211> LENGTH: 324
<212> TYPE: DNA
<213> ORGANISM: Artificial Sequence
<220> FEATURE:
<223> OTHER INFORMATION: Synthetic Construct

<400> SEQUENCE: 11
gacatccaga tgacccagtc tccatcctcc ctgtctgcat ctgtaggaga cagagtcacc    60
atcacttgca gtgtcagctc aagtgtaagt tccatttact tgcactggta tcagcagaaa   120
ccagggaaag cccctaagct cctgatctat agcacatcca acttggcttc tggagtccca   180
tcaaggttca gtggcagtgg atctgggaca gatttcactc tcaccatcag cagtctgcaa   240
cctgaagatt ttgcaactta ctactgtcag gtgtacagtg gttacccgct cacgttcggc    300
ggagggacca aggtggagat caaa                                           324

<210> SEQ ID NO 12
<211> LENGTH: 324
<212> TYPE: DNA
<213> ORGANISM: Artificial Sequence
<220> FEATURE:
<223> OTHER INFORMATION: Synthetic Construct

<400> SEQUENCE: 12
gacatccaga tgacccagtc tccatcctcc ctgtctgcat ctgtaggaga cagagtcacc    60
atcacttgca gtgtcagctc aagtgtacgt tccatttact tgcactggta tcagcagaaa   120
ccagggaaag cccctaagct cctgatctat agcacatcca acttggcttc tggagtccca   180
tcaaggttca gtggcagtgg atctgggaca gatttcactc tcaccatcag cagtctgcaa   240
cctgaagatt ttgcaactta ctactgtcag gtgtacaggg gttacccgct cacgttcggc    300
ggagggacca aggtggagat caaa                                           324

<210> SEQ ID NO 13
<211> LENGTH: 115
<212> TYPE: PRT
<213> ORGANISM: Artificial Sequence
<220> FEATURE:
<223> OTHER INFORMATION: Synthetic Construct
```

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Arg
            20                  25                  30

Tyr Ile His Trp Val Arg Gln Ala Pro Gly Gln Gly Leu Glu Trp Met
        35                  40                  45

Gly Trp Ile Tyr Pro Val Thr Gly Asp Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Ala Phe Tyr Tyr Trp Gly Gln Gly Thr Leu Val
            100                 105                 110

Thr Val Ser
        115

<210> SEQ ID NO 14
<211> LENGTH: 115
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Arg
            20                  25                  30

Tyr Ile His Trp Val Arg Gln Ala Pro Gly Gln Gly Leu Glu Trp Met
        35                  40                  45

Gly Trp Ile Tyr Pro Val Thr Gly Asp Thr Tyr Tyr Ile Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Ala Phe Phe Tyr Trp Gly Gln Gly Thr Leu Val
            100                 105                 110

Thr Val Ser
        115

<210> SEQ ID NO 15
<211> LENGTH: 115
<212> TYPE: PRT
<213> ORGANISM: Artificial Sequence
<220> FEATURE:
<223> OTHER INFORMATION: Synthetic Construct

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Arg
            20                  25                  30

Tyr Ile His Trp Val Arg Gln Ala Pro Gly Gln Gly Leu Glu Trp Met
        35                  40                  45

-continued

Gly Trp Ile Tyr Pro Val Thr Gly Asp Thr Tyr Tyr Arg Glu Pro Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Tyr Gly Ala Phe Tyr Tyr Trp Gly Gln Gly Thr Leu Val
            100                 105                 110

Thr Val Ser
        115

<210> SEQ ID NO 16
<211> LENGTH: 114
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Thr Asn Trp Leu Asp Tyr Trp Gly Gln Gly Thr Thr Val Thr
            100                 105                 110

Val Ser

<210> SEQ ID NO 17
<211> LENGTH: 114
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Arg Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Ala Asn Trp Leu Asp Tyr Trp Gly Gln Gly Thr Thr Val Thr
            100                 105                 110

Val Ser

<210> SEQ ID NO 18
<211> LENGTH: 114
<212> TYPE: PRT
<213> ORGANISM: Artificial Sequence
<220> FEATURE:
<223> OTHER INFORMATION: Synthetic Construct

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Tyr Arg Gly Ser Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Ile Leu Asp Tyr Trp Gly Gln Gly Thr Thr Val Thr
            100                 105                 110

Val Ser
```

<210> SEQ ID NO 19
<211> LENGTH: 345
<212> TYPE: DNA
<213> ORGANISM: Artificial Sequence
<220> FEATURE:
<223> OTHER INFORMATION: Synthetic Construct

<400> SEQUENCE: 19

```
caggtgcagc tggtgcagtc tggggctgag gtgaagaagc ctgggtcctc ggtgaaggtc    60
tcctgcaagg cttctggcta caccttcaca agtaggtata cactgggt gcgacaggcc    120 cctggacaag ggcttgagtg gatgggatgg atttatcctg taactggtga tacttactac    180
aacgagaagt tcaagggcag agtcacgatt accgcggaca atccacgag cacagcctac    240 atggagctga gcagcctgag atctgaggac acggccgtgt attactgtgc gagaggctac    300
ggagcttttt actactgggg ccagggcacc ctggtcaccg tctcc                  345
```

<210> SEQ ID NO 20
<211> LENGTH: 345
<212> TYPE: DNA
<213> ORGANISM: Artificial Sequence
<220> FEATURE:
<223> OTHER INFORMATION: Synthetic Construct

<400> SEQUENCE: 20

```
caggtgcagc tggtgcagtc tggggctgag gtgaagaagc ctgggtcctc ggtgaaggtc    60
tcctgcaagg cttctggcta caccttcaca agtaggtata cactgggt gcgacaggcc    120 cctggacaag ggcttgagtg gatgggatgg atttatcctg taactggtga tacttactac    180
atcgagaagt tcaagggcag agtcacgatt accgcggaca atccacgag cacagcctac    240 atggagctga gcagcctgag atctgaggac acggccgtgt attactgtgc gagaggctat    300
ggtgcttttt tctactgggg ccagggcacc ctggtcaccg tctcc                   345
```

<210> SEQ ID NO 21

```
<211> LENGTH: 345
<212> TYPE: DNA
<213> ORGANISM: Artificial Sequence
<220> FEATURE:
<223> OTHER INFORMATION: Synthetic Construct

<400> SEQUENCE: 21
caggtgcagc tggtgcagtc tggggctgag gtgaagaagc ctgggtcctc ggtgaaggtc      60
tcctgcaagg cttctggcta caccttcaca agtaggtata cactgggt gcgacaggcc      120
cctggacaag ggcttgagtg gatgggatgg atttatcctg taactggtga tacttactac      180
agagagcctt tcaagggcag agtcacgatt accgcggaca atccacgag cacagcctac      240
atggagctga gcagcctgag atctgaggac acggccgtgt attactgtgc gagaggctat      300
ggggcttttt actactgggg ccagggcacc ctggtcaccg tctcc                     345

<210> SEQ ID NO 22
<211> LENGTH: 342
<212> TYPE: DNA
<213> ORGANISM: Artificial Sequence
<220> FEATURE:
<223> OTHER INFORMATION: Synthetic Construct

<400> SEQUENCE: 22
caggttcagc tggtgcagtc tggtgctgag gtgaagaagc ctggtgcctc agtgaaggtc      60
tcctgcaagg cttctggtta cacctttacc gactactaca tgcactgggt gcgtcaggcc      120
cctggtcaag gtcttgagtg gatgggtcgt gttaatccta accggggtgg tactacctac      180
aaccagaaat tcgagggccg tgtcaccatg accacagaca catccacgag cacagcctac      240
atggagctgc gtagcctgcg ttctgacgac acggccgtgt attactgtgc gcgtacgaac      300
tggcttgact actggggcca gggcaccacc gtcaccgtct cc                         342

<210> SEQ ID NO 23
<211> LENGTH: 342
<212> TYPE: DNA
<213> ORGANISM: Artificial Sequence
<220> FEATURE:
<223> OTHER INFORMATION: Synthetic Construct

<400> SEQUENCE: 23
caggttcagc tggtgcagtc tggtgctgag gtgaagaagc ctggtgcctc agtgaaggtc      60
tcctgcaagg cttctggtta cacctttacc gactactaca tgcactgggt gcgtcaggcc      120
cctggtcaag gtcttgagtg gatgggtcgt gttaatccta accggagggg tactacctac      180
aaccagaaat tcgagggccg tgtcaccatg accacagaca catccacgag cacagcctac      240
atggagctgc gtagcctgcg ttctgacgac acggccgtgt attactgtgc gcgtgcgaac      300
tggcttgact actggggcca gggcaccacc gtcaccgtct cc                         342

<210> SEQ ID NO 24
<211> LENGTH: 342
<212> TYPE: DNA
<213> ORGANISM: Artificial Sequence
<220> FEATURE:
<223> OTHER INFORMATION: Synthetic Construct

<400> SEQUENCE: 24
caggttcagc tggtgcagtc tggtgctgag gtgaagaagc ctggtgcctc agtgaaggtc      60
tcctgcaagg cttctggtta cacattcact gactactaca tgcactgggt gcgtcaggcc      120
cctggtcaag gtcttgagtg gatgggtcgt gttaatccta atcggggtag tactacctac      180
```

-continued

```
aaccagaaat tcgagggccg tgtcaccatg accacagaca catccacgag cacagcctac    240
atggagctgc gtagcctgcg ttctgacgac acggccgtgt attactgtgc gcgtgcgaac    300
attcttgact actggggcca gggcaccacc gtcaccgtct cc                       342
```

<210> SEQ ID NO 25
<211> LENGTH: 215
<212> TYPE: PRT
<213> ORGANISM: Artificial Sequence
<220> FEATURE:
<223> OTHER INFORMATION: Synthetic Construct

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Thr
            20                  25                  30

Asn Leu His Trp Tyr Gln Gln Lys Pro Gly Gln Ala Pro Arg Leu Leu
        35                  40                  45

Ile Tyr Gly Thr Ser Tyr Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Tyr Ser Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 26
<211> LENGTH: 215
<212> TYPE: PRT
<213> ORGANISM: Artificial Sequence
<220> FEATURE:
<223> OTHER INFORMATION: Synthetic Construct

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Thr
            20                  25                  30

Asn Leu His Trp Tyr Gln Gln Lys Pro Gly Gln Ala Pro Arg Leu Leu
        35                  40                  45

Ile Tyr Gly Thr Ser Tyr Leu Ala Ser Gly Ile Pro Asp Arg Phe Ser
    50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Trp Ser Ser Tyr Pro
                 85                  90                  95

Tyr Ser Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 215
<212> TYPE: PRT
<213> ORGANISM: Artificial Sequence
<220> FEATURE:
<223> OTHER INFORMATION: Synthetic Construct

<400> SEQUENCE: 27

Glu Ile Val Leu Thr Gln Ser Pro Gly Thr Leu Ser Leu Ser Pro Gly
  1               5                  10                  15

Glu Arg Ala Thr Leu Ser Cys Ser Val Ser Ser Ser Ile Ser Ser Thr
                 20                  25                  30

Asn Leu His Trp Tyr Gln Gln Lys Pro Gly Gln Ala Pro Arg Leu Leu
             35                  40                  45

Ile Tyr Gly Thr Ser Arg Leu Arg Ser Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Trp Ser Ser Tyr Pro
                 85                  90                  95

Tyr Ser Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
```

<210> SEQ ID NO 28
<211> LENGTH: 215
<212> TYPE: PRT
<213> ORGANISM: Artificial Sequence
<220> FEATURE:
<223> OTHER INFORMATION: Synthetic Construct

<400> SEQUENCE: 28

```
Asp Ile Gln Met Thr Gln Ser Pro Ser Ser Leu Ser Ala Ser Val Gly
1               5                  10                  15

Asp Arg Val Thr Ile Thr Cys Ser Val Ser Ser Val Ser Ser Ile
            20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Ile Gln Tyr Ser Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 29
<211> LENGTH: 215
<212> TYPE: PRT
<213> ORGANISM: Artificial Sequence
<220> FEATURE:
<223> OTHER INFORMATION: Synthetic Construct

<400> SEQUENCE: 29

```
Asp Ile Gln Met Thr Gln Ser Pro Ser Ser Leu Ser Ala Ser Val Gly
1               5                  10                  15

Asp Arg Val Thr Ile Thr Cys Ser Val Ser Ser Val Ser Ser Ile
            20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
```

```
                     85                  90                  95
Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 30
<211> LENGTH: 215
<212> TYPE: PRT
<213> ORGANISM: Artificial Sequence
<220> FEATURE:
<223> OTHER INFORMATION: Synthetic Construct

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Ser Val Arg Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Arg Gly Tyr Pro
                85                  90                  95

Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 31
```

-continued

```
<211> LENGTH: 645
<212> TYPE: DNA
<213> ORGANISM: Artificial Sequence
<220> FEATURE:
<223> OTHER INFORMATION: Synthetic Construct

<400> SEQUENCE: 31
gaaattgtgt tgacgcagtc tccaggcacc ctgtctttgt ctccagggga aagagccacc      60
ctctcctgca gtgtcagctc aagtataagt tccaccaact tacactggta ccagcagaaa     120
cctggccagg ctcccaggct cctcatctat ggcacatcct acctggcttc tggcatccca     180
gacaggttca gtggcagtgg gtctgggaca gacttcactc tcaccatcag cagactggag     240
cctgaagatt ttgcagtgta ttactgtcaa cagtggagta gttacccgta cagtttcggc     300
caagggacca gttggagat caaacgaact gtggctgcac catctgtctt catcttcccg      360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagacta cgagaaacac aaagtctacg cctgcgaagt cacccatcag     600
ggcctgagct cgcccgtcac aaagagcttc aacaggggag agtgc                      645

<210> SEQ ID NO 32
<211> LENGTH: 645
<212> TYPE: DNA
<213> ORGANISM: Artificial Sequence
<220> FEATURE:
<223> OTHER INFORMATION: Synthetic Construct

<400> SEQUENCE: 32
gaaattgtgt tgacgcagtc tccaggcacc ctgtctttgt ctccagggga aagagccacc      60
ctctcctgca gtgtcagctc aagtataagt tccaccaact tacactggta ccagcagaaa     120
cctggccagg ctcccaggct cctcatctat ggcacatcct acctggcttc tggcatccca     180
gacaggttca gtggcagtgg gtctgggaca gacttcactc tcaccatcag cagactggag     240
cctgaagatt ttgcagtgta ttactgtcaa cagtggagta gttacccgta cagtttcggc     300
caagggacca gttggagat caaacgaact gtggctgcac catctgtctt catcttcccg      360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagacta cgagaaacac aaagtctacg cctgcgaagt cacccatcag     600
ggcctgagct cgcccgtcac aaagagcttc aacaggggag agtgc                      645

<210> SEQ ID NO 33
<211> LENGTH: 645
<212> TYPE: DNA
<213> ORGANISM: Artificial Sequence
<220> FEATURE:
<223> OTHER INFORMATION: Synthetic Construct

<400> SEQUENCE: 33
gaaattgtgt tgacgcagtc tccaggcacc ctgtctttgt ctccagggga aagagccacc      60
ctctcctgca gtgtcagctc aagtataagt tccaccaact tacactggta ccagcagaaa     120
cctggccagg ctcccaggct cctcatctat ggcacatcca gactgagatc tggcatccca     180
gacaggttca gtggcagtgg gtctgggaca gacttcactc tcaccatcag cagactggag     240
```

```
cctgaagatt ttgcagtgta ttactgtcaa cagtggagta gttacccgta cagtttcggc      300
caagggacca agttggagat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgc                     645

<210> SEQ ID NO 34
<211> LENGTH: 645
<212> TYPE: DNA
<213> ORGANISM: Artificial Sequence
<220> FEATURE:
<223> OTHER INFORMATION: Synthetic Construct

<400> SEQUENCE: 34
gacatccaga tgacccagtc tccatcctcc ctgtctgcat ctgtaggaga cagagtcacc       60
atcacttgca gtgtcagctc aagtgtaagt tccatttact tgcactggta tcagcagaaa      120
ccagggaaag cccctaagct cctgatctat agcacatcca acttggcttc tggagtccca      180
tcaaggttca gtggcagtgg atctgggaca gatttcactc tcaccatcag cagtctgcaa      240
cctgaagatt ttgcaactta ctactgtatt cagtacagtg ttacccgct cacgttcggc       300 ggagggacca aggtggagat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgc                     645

<210> SEQ ID NO 35
<211> LENGTH: 645
<212> TYPE: DNA
<213> ORGANISM: Artificial Sequence
<220> FEATURE:
<223> OTHER INFORMATION: Synthetic Construct

<400> SEQUENCE: 35
gacatccaga tgacccagtc tccatcctcc ctgtctgcat ctgtaggaga cagagtcacc       60
atcacttgca gtgtcagctc aagtgtatcc tccatttact tgcactggta tcagcagaaa      120
ccagggaaag cccctaagct cctgatctat agcacatcca acttggcttc tggagtccca      180
tcaaggttca gtggcagtgg atctgggaca gatttcactc tcaccatcag cagtctgcaa      240
cctgaagatt ttgcaactta ctactgtcaa gtctacagtg ttacccgct cacgttcggc       300 ggagggacca aggtggagat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgc                     645

<210> SEQ ID NO 36
```

<211> LENGTH: 645
<212> TYPE: DNA
<213> ORGANISM: Artificial Sequence
<220> FEATURE:
<223> OTHER INFORMATION: Synthetic Construct

<400> SEQUENCE: 36

```
gacatccaga tgacccagtc tccatcctcc ctgtctgcat ctgtaggaga cagagtcacc    60
atcacttgca gtgtcagctc aagtgtacgt tccatttact tgcactggta tcagcagaaa   120
ccagggaaag cccctaagct cctgatctat agcacatcca acttggcttc tggagtccca   180
tcaaggttca gtggcagtgg atctgggaca gatttcactc tcaccatcag cagtctgcaa   240
cctgaagatt ttgcaactta ctactgtcag gtgtacaggg gttacccgct cacgttcggc   300
ggagggacca aggtggagat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgc                   645
```

<210> SEQ ID NO 37
<211> LENGTH: 441
<212> TYPE: PRT
<213> ORGANISM: Artificial Sequence
<220> FEATURE:
<223> OTHER INFORMATION: Synthetic Construct

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Arg
            20                  25                  30

Tyr Ile His Trp Val Arg Gln Ala Pro Gly Gln Gly Leu Glu Trp Met
        35                  40                  45

Gly Trp Ile Tyr Pro Val Thr Gly Asp Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Ala Phe Tyr Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
```

-continued

```
                210                 215                 220
Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
                260                 265                 270

Tyr Val Asp Gly Met Glu Val His Asn Ala Lys Thr Lys Pro Arg Glu
                275                 280                 285

Glu Gln Phe Asn Ser Thr Phe Arg Val Val Ser Val Leu Thr Val Val
                290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
                340                 345                 350

Met Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly
                435                 440

<210> SEQ ID NO 38
<211> LENGTH: 441
<212> TYPE: PRT
<213> ORGANISM: Artificial Sequence
<220> FEATURE:
<223> OTHER INFORMATION: Synthetic Construct

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Arg
                20                  25                  30

Tyr Ile His Trp Val Arg Gln Ala Pro Gly Gln Gly Leu Glu Trp Met
            35                  40                  45

Gly Trp Ile Tyr Pro Val Thr Gly Asp Thr Tyr Tyr Ile Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Ala Phe Phe Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Cys Val Glu Cys Pro Pro
        210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Met Glu Val His Asn Ala Lys Thr Lys Pro Arg Glu
            275                 280                 285

Glu Gln Phe Asn Ser Thr Phe Arg Val Val Ser Val Leu Thr Val Val
        290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly
            435                 440

<210> SEQ ID NO 39
<211> LENGTH: 441
<212> TYPE: PRT
<213> ORGANISM: Artificial Sequence
<220> FEATURE:
<223> OTHER INFORMATION: Synthetic Construct

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Arg
            20                  25                  30

Tyr Ile His Trp Val Arg Gln Ala Pro Gly Gln Gly Leu Glu Trp Met
        35                  40                  45

Gly Trp Ile Tyr Pro Val Thr Gly Asp Thr Tyr Tyr Arg Glu Pro Phe
    50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Gly Ala Phe Tyr Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Met Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 40
<211> LENGTH: 440
<212> TYPE: PRT
<213> ORGANISM: Artificial Sequence
<220> FEATURE:
<223> OTHER INFORMATION: Synthetic Construct
```

<400> SEQUENCE: 40

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Thr Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Met Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415
```

```
Phe Ser Cys Ser Val Met His Glu Ala Leu His Asn His Tyr Thr Gln
            420                 425                 430

Lys Ser Leu Ser Leu Ser Pro Gly
        435                 440

<210> SEQ ID NO 41
<211> LENGTH: 440
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Met Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
```

```
                        340                 345                 350
Thr Lys Asn Gln Val Ser Leu Thr Cys Leu Val Lys Gly Phe Tyr Pro
                    355                 360                 365

Ser Asp Ile Ala Val Glu Trp Glu Ser Asn Gly Gln Pro Glu Asn Asn
                370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                    405                 410                 415

Phe Ser Cys Ser Val Met His Glu Ala Leu His Asn His Tyr Thr Gln
                420                 425                 430

Lys Ser Leu Ser Leu Ser Pro Gly
                435                 440

<210> SEQ ID NO 42
<211> LENGTH: 440
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Arg Val Asn Pro Tyr Arg Gly Ser Thr Thr Tyr Asn Gln Lys Phe
50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Ala Asn Ile Leu Asp Tyr Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270
```

Val Asp Gly Met Glu Val His Asn Ala Lys Thr Lys Pro Arg Glu Glu
            275                 280                 285

Gln Phe Asn Ser Thr Phe Arg Val Val Ser Val Leu Thr Val Val His
        290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly
        435                 440

<210> SEQ ID NO 43
<211> LENGTH: 1323
<212> TYPE: DNA
<213> ORGANISM: Artificial Sequence
<220> FEATURE:
<223> OTHER INFORMATION: Synthetic Construct

<400> SEQUENCE: 43
caggtgcagc tggtgcagtc tggggctgag gtgaagaagc ctgggtcctc ggtgaaggtc     60
tcctgcaagg cttctggcta caccttcaca agtaggtata cactgggt gcgacaggcc    120 cctggacaag gcttgagtg gatgggatgg atttatcctg taactggtga tacttactac    180
aacgagaagt tcaagggcag agtcacgatt accgcggaca atccacgag cacagcctac    240 atggagctga gcagcctgag atctgaggac acggccgtgt attactgtgc gagaggctat    300
ggggcttttt actactgggg ccagggcacc ctggtcaccg tctcctccgc ctccaccaag    360
ggcccatcgg tcttccccgct agcgccctgc tccaggagca cctccgagag cacagccgcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc aacttcggca cccagaccta cacctgcaac    600
gtagatcaca agcccagcaa caccaaggtg gacaagacag ttgagcgcaa atgttgtgtc    660
gagtgcccac cgtgcccagc accacctgtg gcaggaccgt cagtcttcct cttccccccca    720 aaacccaagg acaccctcat gatctcccgg acccctgagg tcacgtgcgt ggtggtggac    780
gtgagccacg aagaccccga ggtccagttc aactggtacg tggacggcat ggaggtgcat    840
aatgccaaga caaagccacg ggaggagcag ttcaacagca cgttccgtgt ggtcagcgtc    900
ctcaccgtcg tgcaccagga ctggctgaac ggcaaggagt acaagtgcaa ggtctccaac    960
aaaggcctcc cagcccccat cgagaaaacc atctccaaaa ccaaagggca gccccgagaa   1020
ccacaggtgt acaccctgcc cccatcccgg gaggagatga ccaagaacca ggtcagcctg   1080

```
acctgcctgg tcaaaggctt ctaccccagc gacatcgccg tggagtggga gagcaatggg    1140
cagccggaga acaactacaa gaccacacct cccatgctgg actccgacgg ctccttcttc    1200
ctctacagca agctcaccgt ggacaagagc aggtggcagc aggggaacgt cttctcatgc    1260
tccgtgatgc atgaggctct gcacaaccac tacacacaga gagcctctc cctgtctccg    1320 ggt                                                                  1323
```

<210> SEQ ID NO 44
<211> LENGTH: 1323
<212> TYPE: DNA
<213> ORGANISM: Artificial Sequence
<220> FEATURE:
<223> OTHER INFORMATION: Synthetic Construct

<400> SEQUENCE: 44

```
caggtgcagc tggtgcagtc tggggctgag gtgaagaagc ctgggtcctc ggtgaaggtc     60
tcctgcaagg cttctggcta caccttcaca agtaggtata tacactgggt gcgacaggcc    120
cctggacaag gcttgagtg gatgggatgg atttatcctg taactggtga tacttactac    180
atcgagaagt tcaagggcag agtcacgatt accgcggaca atccacgag cacagcctac    240 atggagctga gcagcctgag atctgaggac acggccgtgt attactgtgc gagaggctat    300
ggtgcttttt tctactgggg ccagggcacc ctggtcaccg tctcctccgc ctccaccaag    360
ggcccatcgg tcttccccgct agcgccctgc tccaggagca cctccgagag cacagccgcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc aacttcggca cccagaccta cacctgcaac    600
gtagatcaca agcccagcaa caccaaggtg gacaagacag ttgagcgcaa atgttgtgtc    660
gagtgcccac cgtgcccagc accacctgtg gcaggaccgt cagtcttcct cttccccca    720 aaacccaagg acaccctcat gatctcccgg acccctgagg tcacgtgcgt ggtggtggac    780
gtgagccacg aagaccccga ggtccagttc aactggtacg tggacggcat ggaggtgcat    840
aatgccaaga caaagccacg ggaggagcag ttcaacagca cgttccgtgt ggtcagcgtc    900
ctcaccgtcg tgcaccagga ctggctgaac ggcaaggagt acaagtgcaa ggtctccaac    960
aaaggcctcc cagcccccat cgagaaaacc atctccaaaa ccaaagggca gccccgagaa   1020
ccacaggtgt acaccctgcc cccatcccgg gaggagatga ccaagaacca ggtcagcctg   1080
acctgcctgg tcaaaggctt ctaccccagc gacatcgccg tggagtggga gagcaatggg   1140
cagccggaga acaactacaa gaccacacct cccatgctgg actccgacgg ctccttcttc   1200
ctctacagca agctcaccgt ggacaagagc aggtggcagc aggggaacgt cttctcatgc   1260
tccgtgatgc atgaggctct gcacaaccac tacacacaga gagcctctc cctgtctccg   1320 ggt                                                                 1323
```

<210> SEQ ID NO 45
<211> LENGTH: 1323
<212> TYPE: DNA
<213> ORGANISM: Artificial Sequence
<220> FEATURE:
<223> OTHER INFORMATION: Synthetic Construct

<400> SEQUENCE: 45

```
caggtgcagc tggtgcagtc tggggctgag gtgaagaagc ctgggtcctc ggtgaaggtc     60
tcctgcaagg cttctggcta caccttcaca agtaggtata tacactgggt gcgacaggcc    120
```

```
cctggacaag ggcttgagtg gatgggatgg atttatcctg taactggtga tacttactac        180
agagagcctt tcaagggcag agtcacgatt accgcggaca atccacgag cacagcctac          240 atggagctga gcagcctgag atctgaggac acggccgtgt attactgtgc gagaggctac         300 ggagctttt actactgggg ccagggcacc ctggtcaccg tctcctccgc ctccaccaag          360
ggcccatcgg tcttccccgct agcgccctgc tccaggagca cctccgagag cacagccgcc       420
ctgggctgcc tggtcaagga ctacttcccc gaaccggtga cggtgtcgtg aactcaggc         480 gccctgacca gcggcgtgca caccttcccg gctgtcctac agtcctcagg actctactcc        540
ctcagcagcg tggtgaccgt gccctccagc aacttcggca cccagaccta cacctgcaac        600
gtagatcaca agcccagcaa caccaaggtg gacaagacag ttgagcgcaa atgttgtgtc        660
gagtgcccac cgtgcccagc accacctgtg gcaggaccgt cagtcttcct cttccccccca      720 aaacccaagg acaccctcat gatctcccgg acccctgagg tcacgtgcgt ggtggtggac       780
gtgagccacg aagaccccga ggtccagttc aactggtacg tggacggcat ggaggtgcat      840
aatgccaaga caaagccacg ggaggagcag ttcaacagca cgttccgtgt ggtcagcgtc      900
ctcaccgtcg tgcaccagga ctggctgaac ggcaaggagt acaagtgcaa ggtctccaac      960
aaaggcctcc cagcccccat cgagaaaacc atctccaaaa ccaaagggca gccccgagaa     1020
ccacaggtgt acaccctgcc cccatcccgg gaggagatga ccaagaacca ggtcagcctg     1080
acctgcctgg tcaaaggctt ctaccccagc gacatcgccg tggagtggga gagcaatggg     1140
cagccggaga acaactacaa gaccacacct cccatgctgg actccgacgg ctccttcttc     1200
ctctacagca agctcaccgt ggacaagagc aggtggcagc aggggaacgt cttctcatgc     1260
tccgtgatgc atgaggctct gcacaaccac tacacacaga gagcctctc cctgtctccg     1320 ggt                                                                    1323

<210> SEQ ID NO 46
<211> LENGTH: 1323
<212> TYPE: DNA
<213> ORGANISM: Artificial Sequence
<220> FEATURE:
<223> OTHER INFORMATION: Synthetic Construct

<400> SEQUENCE: 46
caggttcagc tggtgcagtc tggtgctgag gtgaagaagc tggtgcctc agtgaaggtc          60 tcctgcaagg cttctggtta caccttacc gactactaca tgcactgggt gcgtcaggcc        120
cctggtcaag tcttgagtg gatgggtcgt gttaatccta accggggtgg tactacctac         180
aaccagaaat tcgagggccg tgtcaccatg accacagaca catccacgag cacagcctac        240
atggagctgc gtagcctgcg ttctgacgac acggccgtgt attactgtgc gcgtacgaac        300
tggcttgact actggggcca gggcaccacc gtcaccgtct cctccgcctc caccaagggc        360
ccatcggtct tcccgctagc gccctgctcc aggagcacct ccgagagcac agccgccctg       420 gctgcctgg tcaaggacta cttccccgaa ccggtgacgg tgtcgtggaa ctcaggcgcc         480
ctgaccagcg gcgtgcacac cttcccggct gtcctacagt cctcaggact ctactccctc        540
agcagcgtgg tgaccgtgcc ctccagcagc ttgggcacga agacctacac ctgcaacgta        600
gatcacaagc ccagcaacac caaggtggac aagagagttg agtccaaata tggtccccca      660
tgcccaccct gcccagcacc tgaggccgcc ggggaccat cagtcttcct gttccccca        720 aaacccaagg acactctcat gatctcccgg acccctgagg tcacgtgcgt ggtggtggac       780
gtgagccagg aagaccccga ggtccagttc aactggtacg tggatggcgt ggaggtgcat      840
```

```
aatgccaaga caaagccgcg ggaggagcag ttcaacagca cgtaccgtgt ggtcagcgtc    900
ctcaccgtcc tgcaccagga ctggctgaac ggcaaggagt acaagtgcaa ggtctccaac    960
aaaggcctcc cgtcctccat cgagaaaacc atctccaaag ccaaagggca gccccgagag   1020
ccacaggtgt acaccctgcc cccatcccag gaggagatga ccaagaacca ggtcagcctg   1080
acctgcctgg tcaaaggctt ctaccccagc gacatcgccg tggagtggga aagcaatggg   1140
cagccggaga caactacaa gaccacgcct cccgtgctgg actccgacgg ctccttcttc    1200
ctctacagca ggctaaccgt ggacaagagc aggtggcagg aggggaatgt cttctcatgc   1260
tccgtgatgc atgaggctct gcacaaccac tacacacaga gagcctctc cctgtctctg    1320 ggt    1323
```

`<210>` SEQ ID NO 47
`<211>` LENGTH: 1323
`<212>` TYPE: DNA
`<213>` ORGANISM: Artificial Sequence
`<220>` FEATURE:
`<223>` OTHER INFORMATION: Synthetic Construct

`<400>` SEQUENCE: 47

```
caggttcagc tggtgcagtc tggtgctgag gtgaagaagc ctggtgcctc agtgaaggtc     60
tcctgcaagg cttctggtta cacattcact gactactaca tgcactgggt gcgtcaggcc    120
cctggtcaag gtcttgagtg gatgggtcgt gttaatccta accggagggg tactacctac    180
aaccagaaat tcgagggccg tgtcaccatg accacagaca catccacgag cacagcctac    240
atggagctgc gtagcctgcg ttctgacgac acggccgtgt attactgtgc gcgtgcgaac    300
tggcttgact actggggcca gggcaccacc gtcaccgtct cctccgcctc caccaagggc    360
ccatcggtct tccccgctag cgccctgctc caggagcacct ccgagagcac agccgccctg    420
ggctgcctgg tcaaggacta cttccccgaa ccggtgacgg tgtcgtggaa ctcaggcgcc    480
ctgaccagcg gcgtgcacac cttccgggct gtcctacagt cctcaggact ctactccctc    540
agcagcgtgg tgaccgtgcc ctccagcagc ttgggcacga agacctacac ctgcaacgta    600
gatcacaagc ccagcaacac caaggtggac aagagagttg agtccaaata tggtccccca    660
tgcccaccct gcccagcacc tgaggccgcc ggggaccat cagtcttcct gttccccca    720 aaacccaagg acactctcat gatctcccgg acccctgagg tcacgtgcgt ggtggtggac    780
gtgagccagg aagaccccga ggtccagttc aactggtacg tggatggcgt ggaggtgcat    840
aatgccaaga caaagccgcg ggaggagcag ttcaacagca cgtaccgtgt ggtcagcgtc    900
ctcaccgtcc tgcaccagga ctggctgaac ggcaaggagt acaagtgcaa ggtctccaac    960
aaaggcctcc cgtcctccat cgagaaaacc atctccaaag ccaaagggca gccccgagag   1020
ccacaggtgt acaccctgcc cccatcccag gaggagatga ccaagaacca ggtcagcctg   1080
acctgcctgg tcaaaggctt ctaccccagc gacatcgccg tggagtggga aagcaatggg   1140
cagccggaga caactacaa gaccacgcct cccgtgctgg actccgacgg ctccttcttc    1200
ctctacagca ggctaaccgt ggacaagagc aggtggcagg aggggaatgt cttctcatgc   1260
tccgtgatgc atgaggctct gcacaaccac tacacacaga gagcctctc cctgtctctg    1320 ggt    1323
```

`<210>` SEQ ID NO 48
`<211>` LENGTH: 1323
`<212>` TYPE: DNA
`<213>` ORGANISM: Artificial Sequence
`<220>` FEATURE:

<223> OTHER INFORMATION: Synthetic Construct

<400> SEQUENCE: 48

```
caggttcagc tggtgcagtc tggtgctgag gtgaagaagc ctggtgcctc agtgaaggtc    60
tcctgcaagg cttctggtta cacattcact gactactaca tgcactgggt gcgtcaggcc   120
cctggtcaag gtcttgagtg gatgggtcgt gttaatcctt atcggggtag tactacctac   180
aaccagaaat cgagggccg tgtcaccatg accacagaca catccacgag cacagcctac   240
atggagctgc gtagcctgcg ttctgacgac acggccgtgt attactgtgc gcgtgcgaac   300
attcttgact actggggcca gggcaccacc gtcaccgtct cctccgcctc caccaagggc   360
ccatcggtct tccccgctagc gccctgctcc aggagcacct ccgagagcac agccgccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgt gaccgtgcc ctccagcagc ttgggcacga agacctacac ctgcaacgta   600
gatcacaagc ccagcaacac caaggtggac aagagagttg agtccaaata tggtccccca   660
tgcccaccct gcccagcacc tgaggccgcc ggggaccat cagtcttcct gttcccccca    720
aaacccaagg acactctcat gatctcccgg acccctgagg tcacgtgcgt ggtggtggac   780
gtgagccagg aagaccccga ggtccagttc aactggtacg tggatggcgt ggaggtgcat   840
aatgccaaga caaagccgcg ggaggagcag ttcaacagca cgtaccgtgt ggtcagcgtc   900
ctcaccgtcc tgcaccagga ctggctgaac ggcaaggagt acaagtgcaa ggtctccaac   960
aaaggcctcc cgtcctccat cgagaaaacc atctccaaag ccaaagggca gccccgagag  1020
ccacaggtgt acaccctgcc cccatcccag gaggagatga ccaagaacca ggtcagcctg  1080
acctgcctgg tcaaaggctt ctaccccagc gacatcgccg tggagtggga aagcaatggg  1140
cagccggaga acaactacaa gaccacgcct cccgtgctgg actccgacgg ctccttcttc  1200
ctctacagca ggctaaccgt ggacaagagc aggtggcagc aggggaatgt cttctcatgc  1260
tccgtgatgc atgaggctct gcacaaccac tacacacaga gagcctctc cctgtctctg   1320
ggt                                                               1323
```

<210> SEQ ID NO 49
<211> LENGTH: 12
<212> TYPE: PRT
<213> ORGANISM: Artificial Sequence
<220> FEATURE:
<223> OTHER INFORMATION: Synthetic Construct

<400> SEQUENCE: 49

Ser Val Ser Ser Ser Ile Ser Ser Thr Asn Leu His
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct

<400> SEQUENCE: 50

Gly Thr Ser Tyr Leu Ala Ser
1               5

<210> SEQ ID NO 51
<211> LENGTH: 9
<212> TYPE: PRT

```
<213> ORGANISM: Artificial Sequence
<220> FEATURE:
<223> OTHER INFORMATION: Synthetic Construct

<400> SEQUENCE: 51

Gln Gln Trp Ser Ser Tyr Pro Tyr Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Gly Thr Ser Arg Leu Arg Ser
1               5

<210> SEQ ID NO 53
<211> LENGTH: 12
<212> TYPE: PRT
<213> ORGANISM: Artificial Sequence
<220> FEATURE:
<223> OTHER INFORMATION: Synthetic Construct

<400> SEQUENCE: 53

Ser Val Ser Ser Ser Val Ser Ser Ile Tyr Leu His
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Ser Thr Ser Asn Leu Ala Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Ile Gln Tyr Ser Gly Tyr Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Construct

<400> SEQUENCE: 56

Gln Val Tyr Ser Gly Tyr Pro Leu Thr
1               5

<210> SEQ ID NO 57
<211> LENGTH: 12
<212> TYPE: PRT
<213> ORGANISM: Artificial Sequence
<220> FEATURE:
```

<223> OTHER INFORMATION: Synthetic Construct

<400> SEQUENCE: 57

Ser Val Ser Ser Ser Val Arg Ser Ile Tyr Leu His
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

Gln Val Tyr Arg Gly Tyr Pro Leu Thr
1               5

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Gly Tyr Thr Phe Thr Ser Arg Tyr Ile His
1               5                   10

<210> SEQ ID NO 60
<211> LENGTH: 17
<212> TYPE: PRT
<213> ORGANISM: Artificial Sequence
<220> FEATURE:
<223> OTHER INFORMATION: Synthetic Construct

<400> SEQUENCE: 60

Trp Ile Tyr Pro Val Thr Gly Asp Thr Tyr Tyr Asn Glu Lys Phe Lys
1               5                   10                  15

Gly

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct

<400> SEQUENCE: 61

Gly Tyr Gly Ala Phe Tyr Tyr
1               5

<210> SEQ ID NO 62
<211> LENGTH: 17
<212> TYPE: PRT
<213> ORGANISM: Artificial Sequence
<220> FEATURE:
<223> OTHER INFORMATION: Synthetic Construct

<400> SEQUENCE: 62

Trp Ile Tyr Pro Val Thr Gly Asp Thr Tyr Tyr Ile Glu Lys Phe Lys
1               5                   10                  15

Gly

<210> SEQ ID NO 63
<211> LENGTH: 7
<212> TYPE: PRT

<213> ORGANISM: Artificial Sequence
<220> FEATURE:
<223> OTHER INFORMATION: Synthetic Construct

<400> SEQUENCE: 63

Gly Tyr Gly Ala Phe Phe Tyr
1               5

<210> SEQ ID NO 64
<211> LENGTH: 17
<212> TYPE: PRT
<213> ORGANISM: Artificial Sequence
<220> FEATURE:
<223> OTHER INFORMATION: Synthetic Construct

<400> SEQUENCE: 64

Trp Ile Tyr Pro Val Thr Gly Asp Thr Tyr Tyr Arg Glu Pro Phe Lys
1               5                   10                  15

Gly

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Gly Tyr Thr Phe Thr Asp Tyr Tyr Met His
1               5                   10

<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

Arg Val Asn Pro Asn Arg Gly Gly Thr Thr Tyr Asn Gln Lys Phe Glu
1               5                   10                  15

Gly

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct

<400> SEQUENCE: 67

Thr Asn Trp Leu Asp Tyr
1               5

<210> SEQ ID NO 68
<211> LENGTH: 17
<212> TYPE: PRT
<213> ORGANISM: Artificial Sequence
<220> FEATURE:
<223> OTHER INFORMATION: Synthetic Construct

<400> SEQUENCE: 68

Arg Val Asn Pro Asn Arg Arg Gly Thr Thr Tyr Asn Gln Lys Phe Glu
1               5                   10                  15

Gly

<210> SEQ ID NO 69
<211> LENGTH: 6
<212> TYPE: PRT
<213> ORGANISM: Artificial Sequence
<220> FEATURE:
<223> OTHER INFORMATION: Synthetic Construct

<400> SEQUENCE: 69

Ala Asn Trp Leu Asp Tyr
1               5

<210> SEQ ID NO 70
<211> LENGTH: 17
<212> TYPE: PRT
<213> ORGANISM: Artificial Sequence
<220> FEATURE:
<223> OTHER INFORMATION: Synthetic Construct

<400> SEQUENCE: 70

Arg Val Asn Pro Tyr Arg Gly Ser Thr Thr Tyr Asn Gln Lys Phe Glu
1               5                   10                  15

Gly

<210> SEQ ID NO 71
<211> LENGTH: 6
<212> TYPE: PRT
<213> ORGANISM: Artificial Sequence
<220> FEATURE:
<223> OTHER INFORMATION: Synthetic Construct

<400> SEQUENCE: 71

Ala Asn Ile Leu Asp Tyr
1               5

<210> SEQ ID NO 72
<211> LENGTH: 1192
<212> TYPE: PRT
<213> ORGANISM: Homo sapiens

<400> SEQUENCE: 72

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val

```
                165                 170                 175
Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
                210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
                290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
                550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590
```

```
Asn Asn Lys Phe Asp Leu Lys Lys Thr Arg Val Leu Leu Gly Asn Glu
    595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                    675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                    755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
            805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                    835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
            885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
                    915                 920                 925

Gln Asn Phe Thr Leu Glu Val Leu Phe Gln Gly Pro Asp Ile Glu Pro
930                 935                 940

Lys Ser Cys Asp Lys Thr His Thr Cys Pro Pro Cys Pro Ala Pro Glu
945                 950                 955                 960

Leu Leu Gly Gly Pro Ser Val Phe Leu Phe Pro Pro Lys Pro Lys Asp
            965                 970                 975

Thr Leu Met Ile Ser Arg Thr Pro Glu Val Thr Cys Val Val Val Asp
                980                 985                 990

Val Ser His Glu Asp Pro Glu Val  Lys Phe Asn Trp Tyr  Val Asp Gly
            995                1000                1005

Val Glu  Val His Asn Ala Lys  Thr Lys Pro Arg Glu  Glu Gln Tyr
    1010                1015                1020
```

```
Asn Ser Thr Tyr Arg Val Val Ser Val Leu Thr Val Leu His Gln
    1025                1030                1035

Asp Trp Leu Asn Gly Lys Glu Tyr Lys Cys Lys Val Ser Asn Lys
    1040                1045                1050

Ala Leu Pro Ala Pro Ile Glu Lys Thr Ile Ser Lys Ala Lys Gly
    1055                1060                1065

Gln Pro Arg Glu Pro Gln Val Tyr Thr Leu Pro Pro Ser Arg Glu
    1070                1075                1080

Glu Met Thr Lys Asn Gln Val Ser Leu Thr Cys Leu Val Lys Gly
    1085                1090                1095

Phe Tyr Pro Ser Asp Ile Ala Val Glu Trp Glu Ser Asn Gly Gln
    1100                1105                1110

Pro Glu Asn Asn Tyr Lys Thr Thr Pro Pro Val Leu Asp Ser Asp
    1115                1120                1125

Gly Ser Phe Phe Leu Tyr Ser Lys Leu Thr Val Asp Lys Ser Arg
    1130                1135                1140

Trp Gln Gln Gly Asn Val Phe Ser Cys Ser Val Met His Glu Ala
    1145                1150                1155

Leu His Asn His Tyr Thr Gln Lys Ser Leu Ser Leu Ser Pro Gly
    1160                1165                1170

Lys Arg Ile Asp Tyr Lys Asp Asp Asp Lys His Val His His
    1175                1180                1185

His His His His
    1190

<210> SEQ ID NO 73
<211> LENGTH: 1192
<212> TYPE: PRT
<213> ORGANISM: Macaca mulatta

<400> SEQUENCE: 73

Met Lys Ala Pro Ala Val Leu Val Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Ala Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Asn Gln Cys Pro Asp Cys Val
                165                 170                 175

Val Ser Ala Leu Gly Ala Lys Val Leu Ser Ser Val Lys Asp Arg Phe
            180                 185                 190
```

```
Ile Asn Phe Phe Val Gly Asn Thr Ile Asn Ser Ser Tyr Phe Pro His
        195                 200                 205
His Pro Leu His Ser Ile Ser Val Arg Arg Leu Lys Glu Thr Lys Asp
    210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Ile His Ala Phe Glu Ser Asn
                245                 250                 255
Asn Phe Ile Tyr Phe Leu Thr Val Gln Arg Glu Thr Leu Asn Ala Gln
            260                 265                 270
Thr Phe His Thr Arg Ile Ile Arg Phe Cys Ser Leu Asn Ser Gly Leu
        275                 280                 285
His Ser Tyr Met Glu Met Pro Leu Glu Cys Ile Leu Thr Glu Lys Arg
        290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
            340                 345                 350
Ser Ala Glu Pro Met Asp Arg Ser Ala Met Cys Ala Phe Pro Ile Lys
        355                 360                 365
Tyr Val Asn Asp Phe Phe Asn Lys Ile Val Asn Lys Asn Asn Val Arg
        370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Ala Glu Phe Thr Thr Ala Leu Gln Arg Val Asp Leu Phe Met Gly
            420                 425                 430
Gln Phe Ser Glu Val Leu Leu Thr Ser Ile Ser Thr Phe Val Lys Gly
        435                 440                 445
Asp Leu Thr Ile Ala Asn Leu Gly Thr Ser Glu Gly Arg Phe Met Gln
    450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Pro Leu
                485                 490                 495
Asn Gln Asn Gly Tyr Thr Leu Val Val Thr Gly Lys Lys Ile Thr Lys
            500                 505                 510
Ile Pro Leu Asn Gly Leu Gly Cys Arg His Phe Gln Ser Cys Ser Gln
        515                 520                 525
Cys Leu Ser Ala Pro Pro Phe Val Gln Cys Gly Trp Cys His Asp Lys
530                 535                 540
Cys Val Arg Ser Glu Glu Cys Pro Ser Gly Thr Trp Thr Gln Gln Ile
545                 550                 555                 560
Cys Leu Pro Ala Ile Tyr Lys Val Phe Pro Thr Ser Ala Pro Leu Glu
                565                 570                 575
Gly Gly Thr Arg Leu Thr Ile Cys Gly Trp Asp Phe Gly Phe Arg Arg
            580                 585                 590
Asn Asn Lys Phe Asp Leu Lys Lys Thr Arg Val Leu Leu Gly Asn Glu
        595                 600                 605
Ser Cys Thr Leu Thr Leu Ser Glu Ser Thr Met Asn Thr Leu Lys Cys
```

-continued

```
            610                 615                 620
Thr Val Gly Pro Ala Met Asn Lys His Phe Asn Met Ser Ile Ile
625                 630                 635                 640

Ser Asn Gly His Gly Thr Thr Gln Tyr Ser Thr Phe Ser Tyr Val Asp
                    645                 650                 655

Pro Ile Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu His
            755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
            850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Leu Glu Val Leu Phe Gln Gly Pro Asp Ile Glu Pro
            930                 935                 940

Lys Ser Cys Asp Lys Thr His Thr Cys Pro Pro Cys Pro Ala Pro Glu
945                 950                 955                 960

Leu Leu Gly Gly Pro Ser Val Phe Leu Phe Pro Pro Lys Pro Lys Asp
                965                 970                 975

Thr Leu Met Ile Ser Arg Thr Pro Glu Val Thr Cys Val Val Val Asp
            980                 985                 990

Val Ser His Glu Asp Pro Glu Val Lys Phe Asn Trp Tyr Val Asp Gly
            995                 1000                1005

Val Glu Val His Asn Ala Lys Thr Lys Pro Arg Glu Glu Gln Tyr
        1010                1015                1020

Asn Ser Thr Tyr Arg Val Val Ser Val Leu Thr Val Leu His Gln
            1025                1030                1035
```

```
Asp Trp Leu Asn Gly Lys Glu Tyr Lys Cys Lys Val Ser Asn Lys
    1040                1045                1050

Ala Leu Pro Ala Pro Ile Glu Lys Thr Ile Ser Lys Ala Lys Gly
    1055                1060                1065

Gln Pro Arg Glu Pro Gln Tyr Thr Leu Pro Ser Arg Glu
    1070                1075                1080

Glu Met Thr Lys Asn Gln Val Ser Leu Thr Cys Leu Val Lys Gly
    1085                1090                1095

Phe Tyr Pro Ser Asp Ile Ala Val Glu Trp Glu Ser Asn Gly Gln
    1100                1105                1110

Pro Glu Asn Asn Tyr Lys Thr Thr Pro Pro Val Leu Asp Ser Asp
    1115                1120                1125

Gly Ser Phe Phe Leu Tyr Ser Lys Leu Thr Val Asp Lys Ser Arg
    1130                1135                1140

Trp Gln Gln Gly Asn Val Phe Ser Cys Ser Val Met His Glu Ala
    1145                1150                1155

Leu His Asn His Tyr Thr Gln Lys Ser Leu Ser Leu Ser Pro Gly
    1160                1165                1170

Lys Arg Ile Asp Tyr Lys Asp Asp Asp Lys His Val His His
    1175                1180                1185

His His His His
    1190

<210> SEQ ID NO 74
<211> LENGTH: 1194
<212> TYPE: PRT
<213> ORGANISM: Rattus rattus

<400> SEQUENCE: 74

Met Lys Ala Pro Thr Ala Leu Ala Pro Gly Ile Leu Leu Leu Leu
1                   5                   10                  15

Thr Leu Ala Gln Arg Ser His Gly Glu Cys Lys Glu Ala Leu Val Lys
            20                  25                  30

Ser Glu Met Asn Val Asn Met Lys Tyr Gln Leu Pro Asn Phe Thr Ala
            35                  40                  45

Glu Thr Pro Ile His Asn Val Val Leu His Gly His His Ile Tyr Leu
    50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Val Glu His Pro Asp Cys Phe
                85                  90                  95

Pro Cys Gln Asp Cys Ser Ser Lys Ala Asn Val Ser Gly Gly Val Trp
            100                 105                 110

Lys Asp Asn Val Asn Met Ala Leu Leu Val Asp Thr Tyr Tyr Asp Asp
            115                 120                 125

Gln Leu Ile Ser Cys Gly Ser Val Asn Arg Gly Thr Cys Gln Arg His
    130                 135                 140

Val Leu Pro Pro Asp Asn Ala Ala Asp Ile Gln Ser Glu Val His Cys
145                 150                 155                 160

Met Phe Ser Pro Leu Ala Glu Glu Ser Gly Gln Cys Pro Asp Cys
                165                 170                 175

Val Val Ser Ala Leu Gly Ala Lys Val Leu Leu Ser Glu Lys Asp Arg
            180                 185                 190

Phe Ile Asn Phe Phe Val Gly Asn Thr Ile Asn Ser Ser Tyr Pro Pro
            195                 200                 205
```

```
Asp Tyr Ser Leu His Ser Ile Ser Val Arg Arg Leu Lys Glu Thr Gln
    210                 215                 220

Asp Gly Phe Lys Phe Leu Thr Asp Gln Ser Tyr Ile Asp Val Leu Pro
225                 230                 235                 240

Glu Phe Arg Asp Ser Tyr Pro Ile Lys Tyr Ile His Ala Phe Glu Ser
                245                 250                 255

Asn His Phe Ile Tyr Phe Leu Thr Val Gln Lys Glu Thr Leu Asp Ala
                260                 265                 270

Gln Thr Phe His Thr Arg Ile Ile Arg Phe Cys Ser Val Asp Ser Gly
            275                 280                 285

Leu His Ser Tyr Met Glu Met Pro Leu Glu Cys Ile Leu Thr Glu Lys
    290                 295                 300

Arg Arg Lys Arg Ser Thr Arg Glu Glu Val Phe Asn Ile Leu Gln Ala
305                 310                 315                 320

Ala Tyr Val Ser Lys Pro Gly Ala Asn Leu Ala Lys Gln Ile Gly Ala
                325                 330                 335

Ser Pro Tyr Asp Asp Ile Leu Tyr Gly Val Phe Ala Gln Ser Lys Pro
                340                 345                 350

Asp Ser Ala Glu Pro Met Asn Arg Ser Ala Val Cys Ala Phe Pro Ile
            355                 360                 365

Lys Tyr Val Asn Asp Phe Phe Asn Lys Ile Val Asn Lys Asn Asn Val
    370                 375                 380

Arg Cys Leu Gln His Phe Tyr Gly Pro Asn His Glu His Cys Phe Asn
385                 390                 395                 400

Arg Thr Leu Leu Arg Asn Ser Ser Gly Cys Glu Val Arg Ser Asp Glu
                405                 410                 415

Tyr Arg Thr Glu Phe Thr Thr Ala Leu Gln Arg Val Asp Leu Phe Met
                420                 425                 430

Gly Arg Leu Asn His Val Leu Leu Thr Ser Ile Ser Thr Phe Ile Lys
            435                 440                 445

Gly Asp Leu Thr Ile Ala Asn Leu Gly Thr Ser Glu Gly Arg Phe Met
    450                 455                 460

Gln Val Val Leu Ser Arg Thr Ala His Phe Thr Pro His Val Asn Phe
465                 470                 475                 480

Leu Leu Asp Ser Tyr Pro Val Ser Pro Glu Val Ile Val Glu His Pro
                485                 490                 495

Ser Asn Gln Asn Gly Tyr Thr Leu Val Val Thr Gly Lys Lys Ile Thr
                500                 505                 510

Lys Ile Pro Leu Asn Gly Leu Gly Cys Gly His Phe Gln Ser Cys Ser
            515                 520                 525

Gln Cys Leu Ser Ala Pro Tyr Phe Ile Gln Cys Gly Trp Cys His Asn
    530                 535                 540

Arg Cys Val His Ser Asn Glu Cys Pro Ser Gly Thr Trp Thr Gln Glu
545                 550                 555                 560

Ile Cys Leu Pro Ala Val Tyr Lys Val Phe Pro Thr Ser Ala Pro Leu
                565                 570                 575

Glu Gly Gly Thr Met Leu Thr Ile Cys Gly Trp Asp Phe Gly Phe Lys
                580                 585                 590

Lys Asn Asn Lys Phe Asp Leu Arg Lys Thr Lys Val Leu Leu Gly Asn
            595                 600                 605

Glu Ser Cys Thr Leu Thr Leu Ser Glu Ser Thr Thr Asn Thr Leu Lys
    610                 615                 620

Cys Thr Val Gly Pro Ala Met Ser Glu His Phe Asn Val Ser Val Ile
625                 630                 635                 640
```

```
Val Ser Asn Ser Arg Glu Thr Thr Gln Tyr Ser Ala Phe Ser Tyr Val
            645                 650                 655

Asp Pro Val Ile Thr Ser Ile Ser Pro Arg Tyr Gly Pro His Ala Gly
            660                 665                 670

Gly Thr Leu Leu Thr Leu Thr Gly Lys Tyr Leu Asn Ser Gly Asn Ser
            675                 680                 685

Arg His Ile Ser Ile Gly Gly Lys Thr Cys Thr Leu Lys Ser Val Ser
            690                 695                 700

Asp Ser Ile Leu Glu Cys Tyr Thr Pro Gly His Thr Val Ser Ala Glu
705                 710                 715                 720

Phe Pro Val Lys Leu Lys Ile Asp Leu Ala Asp Arg Val Thr Ser Ser
                725                 730                 735

Phe Ser Tyr Arg Glu Asp Pro Val Val Ser Glu Ile His Pro Thr Lys
                740                 745                 750

Ser Phe Ile Ser Gly Gly Ser Thr Ile Thr Gly Ile Gly Lys Asn Leu
            755                 760                 765

Asn Ser Val Ser Thr Pro Lys Leu Val Ile Glu Val His Asp Val Gly
770                 775                 780

Val Asn Tyr Thr Val Ala Cys Gln His Arg Ser Ser Glu Ile Ile
785                 790                 795                 800

Cys Cys Thr Thr Pro Ser Leu Gln Gln Leu Asp Leu Gln Leu Pro Leu
                805                 810                 815

Lys Thr Lys Ala Phe Phe Leu Leu Asp Gly Ile Leu Ser Lys His Phe
                820                 825                 830

Asp Leu Thr Tyr Val His Asp Pro Met Phe Lys Pro Phe Glu Lys Pro
                835                 840                 845

Val Met Ile Ser Met Gly Asn Glu Asn Val Val Glu Ile Lys Gly Asp
850                 855                 860

Asp Ile Asp Pro Glu Ala Val Lys Gly Glu Val Leu Lys Val Gly Asn
865                 870                 875                 880

Lys Ser Cys Glu Asn Leu His Trp His Ser Glu Ala Leu Leu Cys Thr
                885                 890                 895

Val Pro Ser Asp Leu Leu Lys Leu Asn Gly Gly Glu Leu Asn Ile Glu
                900                 905                 910

Trp Lys Gln Ala Val Ser Ser Thr Val Leu Gly Lys Val Ile Val Gln
                915                 920                 925

Pro Asp Gln Asn Phe Ala Leu Glu Val Leu Phe Gln Gly Pro Asp Ile
            930                 935                 940

Glu Pro Lys Ser Cys Asp Lys Thr His Thr Cys Pro Pro Cys Pro Ala
945                 950                 955                 960

Pro Glu Leu Leu Gly Gly Pro Ser Val Phe Leu Phe Pro Pro Lys Pro
                965                 970                 975

Lys Asp Thr Leu Met Ile Ser Arg Thr Pro Glu Val Thr Cys Val Val
                980                 985                 990

Val Asp Val Ser His Glu Asp Pro  Glu Val Lys Phe Asn  Trp Tyr Val
            995                 1000                1005

Asp Gly Val Glu Val His Asn  Ala Lys Thr Lys Pro  Arg Glu Glu
    1010                1015                1020

Gln Tyr Asn Ser Thr Tyr Arg  Val Val Ser Val Leu  Thr Val Leu
        1025                1030                1035

His Gln Asp Trp Leu Asn Gly  Lys Glu Tyr Lys Cys  Lys Val Ser
    1040                1045                1050

Asn Lys Ala Leu Pro Ala Pro  Ile Glu Lys Thr Ile  Ser Lys Ala
```

-continued

```
              1055              1060              1065

Lys Gly Gln Pro Arg Glu Pro Gln Glu Tyr Thr Leu Pro Pro Ser
    1070              1075              1080

Arg Glu Glu Met Thr Lys Asn Gln Val Ser Leu Thr Cys Leu Val
    1085              1090              1095

Lys Gly Phe Tyr Pro Ser Asp Ile Ala Val Glu Trp Glu Ser Asn
    1100              1105              1110

Gly Gln Pro Glu Asn Asn Tyr Lys Thr Thr Pro Pro Val Leu Asp
    1115              1120              1125

Ser Asp Gly Ser Phe Phe Leu Tyr Ser Lys Leu Thr Val Asp Lys
    1130              1135              1140

Ser Arg Trp Gln Gln Gly Asn Val Phe Ser Cys Ser Val Met His
    1145              1150              1155

Glu Ala Leu His Asn His Tyr Thr Gln Lys Ser Leu Ser Leu Ser
    1160              1165              1170

Pro Gly Lys Arg Ile Asp Tyr Lys Asp Asp Asp Lys His Val
    1175              1180              1185

His His His His His His
    1190

<210> SEQ ID NO 75
<211> LENGTH: 932
<212> TYPE: PRT
<213> ORGANISM: Homo sapiens

<400> SEQUENCE: 75

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
```

```
              225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
                290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655
```

```
Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr
930

<210> SEQ ID NO 76
<211> LENGTH: 578
<212> TYPE: PRT
<213> ORGANISM: Homo sapiens

<400> SEQUENCE: 76

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95
```

-continued

```
Pro Cys Gln Asp Cys Ser Ser Lys Ala Asn Leu Ser Gly Gly Val Trp
                100                 105                 110
Lys Asp Asn Ile Asn Met Ala Leu Val Val Asp Thr Tyr Tyr Asp Asp
            115                 120                 125
Gln Leu Ile Ser Cys Gly Ser Val Asn Arg Gly Thr Cys Gln Arg His
        130                 135                 140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                165                 170                 175
Val Ser Ala Leu Gly Ala Lys Val Leu Ser Ser Val Lys Asp Arg Phe
            180                 185                 190
Ile Asn Phe Phe Val Gly Asn Thr Ile Asn Ser Ser Tyr Phe Pro Asp
        195                 200                 205
His Pro Leu His Ser Ile Ser Val Arg Arg Leu Lys Glu Thr Lys Asp
210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                245                 250                 255
Asn Phe Ile Tyr Phe Leu Thr Val Gln Arg Glu Thr Leu Asp Ala Gln
            260                 265                 270
Thr Phe His Thr Arg Ile Ile Arg Phe Cys Ser Ile Asn Ser Gly Leu
        275                 280                 285
His Ser Tyr Met Glu Met Pro Leu Glu Cys Ile Leu Thr Glu Lys Arg
290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
            340                 345                 350
Ser Ala Glu Pro Met Asp Arg Ser Ala Met Cys Ala Phe Pro Ile Lys
        355                 360                 365
Tyr Val Asn Asp Phe Phe Asn Lys Ile Val Asn Lys Asn Asn Val Arg
370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
        435                 440                 445
Asp Leu Thr Ile Ala Asn Leu Gly Thr Ser Glu Gly Arg Phe Met Gln
450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
            500                 505                 510
Ile Pro Leu Asn Gly Leu Gly Cys Arg His Phe Gln Ser Cys Ser Gln
        515                 520                 525
```

```
Cys Leu Ser Ala Pro Pro Phe Val Gln Cys Gly Trp Cys His Asp Lys
    530                 535                 540
Cys Val Arg Ser Glu Glu Cys Leu Ser Gly Thr Trp Thr Gln Gln Ile
545                 550                 555                 560
Cys Leu Asp Tyr Lys Asp Asp Asp Lys His Val His His His
                565                 570                 575
His His
```

<210> SEQ ID NO 77
<211> LENGTH: 10
<212> TYPE: PRT
<213> ORGANISM: Homo sapiens

<400> SEQUENCE: 77

```
Val Val Asp Thr Tyr Tyr Asp Asp Gln Leu
1               5                   10
```

<210> SEQ ID NO 78
<211> LENGTH: 25
<212> TYPE: PRT
<213> ORGANISM: Homo sapiens

<400> SEQUENCE: 78

```
Ile Ser Cys Gly Ser Val Asn Arg Gly Thr Cys Gln Arg His Val Phe
1               5                   10                  15
Pro His Asn His Thr Ala Asp Ile Gln
            20                  25
```

<210> SEQ ID NO 79
<211> LENGTH: 18
<212> TYPE: PRT
<213> ORGANISM: Homo sapiens

<400> SEQUENCE: 79

```
Ala Leu Gly Ala Lys Val Leu Ser Ser Val Lys Asp Arg Phe Ile Asn
1               5                   10                  15
Phe Phe
```

<210> SEQ ID NO 80
<211> LENGTH: 12
<212> TYPE: PRT
<213> ORGANISM: Homo sapiens

<400> SEQUENCE: 80

```
Val Arg Arg Leu Lys Glu Thr Lys Asp Gly Phe Met
1               5                   10
```

<210> SEQ ID NO 81
<211> LENGTH: 6
<212> TYPE: PRT
<213> ORGANISM: Homo sapiens

<400> SEQUENCE: 81

```
Asp Thr Tyr Tyr Asp Asp
1               5
```

<210> SEQ ID NO 82
<211> LENGTH: 13
<212> TYPE: PRT
<213> ORGANISM: Homo sapiens

<400> SEQUENCE: 82

His Val Phe Pro His Asn His Thr Ala Asp Ile Gln Ser
1               5                   10

<210> SEQ ID NO 83
<211> LENGTH: 4
<212> TYPE: PRT
<213> ORGANISM: Homo sapiens

<400> SEQUENCE: 83

Phe Ile Asn Phe
1

<210> SEQ ID NO 84
<211> LENGTH: 8
<212> TYPE: PRT
<213> ORGANISM: Homo sapiens

<400> SEQUENCE: 84

Lys Glu Thr Lys Asp Gly Phe Met
1               5

<210> SEQ ID NO 85
<211> LENGTH: 24
<212> TYPE: PRT
<213> ORGANISM: Homo sapiens

<400> SEQUENCE: 85

Tyr Lys Thr Gly Pro Val Leu Glu His Pro Asp Cys Phe Pro Cys Gln
1               5                   10                  15

Asp Cys Ser Ser Lys Ala Asn Leu
            20

<210> SEQ ID NO 86
<211> LENGTH: 11
<212> TYPE: PRT
<213> ORGANISM: Homo sapiens

<400> SEQUENCE: 86

Cys Phe Pro Cys Gln Asp Cys Ser Ser Lys Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 87

Gly Thr Ser Xaa Leu Xaa Ser
1               5

<210> SEQ ID NO 88
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature

```
<222> LOCATION: (7)..(7)
<223> OTHER INFORMATION: Xaa can be any naturally occurring amino acid

<400> SEQUENCE: 88

Ser Val Ser Ser Ser Val Xaa Ser Ile Tyr Leu His
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 89

Xaa Xaa Tyr Xaa Gly Tyr Pro Leu Thr
1               5

<210> SEQ ID NO 90
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 90

Trp Ile Tyr Pro Val Thr Gly Asp Thr Tyr Tyr Xaa Glu Xaa Phe Lys
1               5                   10                  15

Gly

<210> SEQ ID NO 91
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid

<400> SEQUENCE: 91

Gly Tyr Gly Ala Phe Xaa Tyr
1               5

<210> SEQ ID NO 92
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid
```

```
<220> FEATURE:
<221> NAME/KEY: misc_feature
<222> LOCATION: (7)..(8)
<223> OTHER INFORMATION: Xaa can be any naturally occurring amino acid

<400> SEQUENCE: 92

Arg Val Asn Pro Xaa Arg Xaa Xaa Thr Thr Tyr Asn Gln Lys Phe Glu
1               5                   10                  15

Gly

<210> SEQ ID NO 93
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 93

Xaa Asn Xaa Leu Asp Tyr
1               5

<210> SEQ ID NO 94
<211> LENGTH: 108
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 94

Glu Ile Val Leu Thr Gln Ser Pro Gly Thr Leu Ser Leu Ser Pro Gly
1               5                   10                  15

Glu Arg Ala Thr Leu Ser Cys Ser Val Ser Ser Ile Ser Ser Thr
            20                  25                  30

Asn Leu His Trp Tyr Gln Gln Lys Pro Gly Gln Ala Pro Arg Leu Leu
        35                  40                  45

Ile Tyr Gly Thr Ser Xaa Leu Xaa Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Tyr Ser Phe Gly Gln Gly Thr Lys Leu Glu Ile Lys
            100                 105

<210> SEQ ID NO 95
<211> LENGTH: 108
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Ser Val Xaa Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Xaa Xaa Tyr Xaa Gly Tyr Pro
                85                  90                  95

Leu Thr Phe Gly Gly Gly Thr Lys Val Glu Ile Lys
            100                 105

<210> SEQ ID NO 96
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Arg
            20                  25                  30

Tyr Ile His Trp Val Arg Gln Ala Pro Gly Gln Gly Leu Glu Trp Met
        35                  40                  45

Gly Trp Ile Tyr Pro Val Thr Gly Asp Thr Tyr Tyr Xaa Glu Xaa Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Ala Phe Xaa Tyr Trp Gly Gln Gly Thr Leu Val
            100                 105                 110

Thr Val Ser
        115
```

```
<210> SEQ ID NO 97
<211> LENGTH: 114
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Xaa Arg Xaa Xaa Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Xaa Asn Xaa Leu Asp Tyr Trp Gly Gln Gly Thr Thr Val Thr
                100                 105                 110

Val Ser
```

C-MET ANTIBODIES

This application claims the benefit under 35 U.S.C. §119 (e) of U.S. Provisional Application Ser. No. 61/116,825, filed Nov. 21, 2008 and U.S. Provisional Application Ser. No. 61/219,903, filed Jun. 24, 2009, both of which are expressly incorporated herein by reference in their entirety.

The present invention relates to antibodies that bind c-Met and their use in treating conditions and disorders in which pathogenesis is mediated by this receptor.

c-Met, a member of the tyrosine kinase superfamily, is the receptor for Hepatocyte Growth Factor (HGF). Binding of HGF to c-Met leads to receptor dimerization or multimerization, phosphorylation of multiple tyrosine residues in the intracellular region, catalytic activation, and downstream signaling. c-Met is also activated via ligand-independent mechanisms, including receptor over-expression, amplification, and mutation. c-Met activation enhances cellular proliferation, migration, morphogenesis, survival (including protection from apoptosis), and protease synthesis, characteristics that are associated with invasive cell phenotype and poor clinical outcomes and drug resistance in cancer patients. The c-Met signaling pathway is one of the most frequently dysregulated pathways in human cancers, and occurs in virtually all types of solid tumors.

PCT International Publication WO 09/007,427 discloses murine and CDR-grafted, humanized c-Met antibodies. Murine antibody 224G11 disclosed therein did not bind the c-Met Sema domain. Further functional properties of the humanized IgG1 derivative of this murine antibody, denoted h224G11 Mab, are reported in Abstracts nos. 835 (in vitro data) and 2792 (in vivo data) and their accompanying posters presented at the meeting of the American Association for Cancer Research (Denver, Colo.) in April, 2009. These abstracts and posters disclose that bivalent h224G11 Mab is devoid of intrinsic agonistic properties, behaves as a full antagonist of c-Met, and potently decreases c-Met dimerization. Murine 224G11 is reported to down-regulate c-Met and block c-Met phosphorylation in vivo. In the case of other receptors, dimerization is a prerequisite for receptor internalization and degradation. These abstracts and posters disclose no data relating to c-Met internalization. Furthermore, the epitope to which the humanized antibody binds within c-Met is not identified.

PCT International Publication WO 05/016382 also discloses c-Met antibodies but does not identify the epitope(s) to which the antibodies bind. An epitope mapping example is provided, however, the reported results merely indicate that six c-Met antibodies bind to a common epitope while a seventh c-Met antibody binds a distinct epitope. The particular epitopes to which these c-Met antibodies bind is not provided.

There exists a need for antagonist antibodies to human c-Met, binding of which to the α-chain of human c-Met facilitates internalization of the receptor from the cell surface, in the presence and/or absence of HGF. There is also a need for antagonist antibodies to human c-Met, which binding to the α-chain of human c-Met facilitates internalization of the receptor from the cell surface in cells comprising c-Met variants containing gain of function mutations. There is also a need for antagonist antibodies to human c-Met which induce c-Met degradation and reduction of phosphorylated c-Met. Such antagonist activities could decrease the number of available binding sites for HGF on tumor cell surfaces, and terminate the pathway activation caused by overexpression, amplification, or mutation of c-Met. At the same time, such antagonist antibodies should inhibit HGF binding to c-Met and HGF-induced c-Met activation, and induce little or no agonist activity themselves.

Antibody compounds of the present invention meet these needs. They bind to epitopes in the α-chain of the human c-Met Sema domain, inhibiting HGF-binding to c-Met and receptor activation, while inducing little or no agonist activity. The antibodies of the present invention also induce internalization of the receptor in the presence or absence of HGF and also in cells comprising c-Met variants containing gain of function mutations. They induce degradation of c-Met and induce reduction of phosphorylated human c-Met, and inhibit HGF-dependent and HGF-independent proliferation of tumor cells that express this receptor. In view of these properties, these antibody compounds should be therapeutically useful in treating cancers mediated by c-Met via a variety of different mechanisms.

In addition, the present antibody compounds possess a number of other desirable properties. They exhibit high affinity ($K_D$) to c-Met, block HGF-mediated c-Met phosphorylation and downstream signaling, cellular proliferation, and cellular migration; and induce only weak phosphorylation of c-Met while inducing little or no HGF-like biological agonist activities such as induction of tumor cell proliferation, motility, invasion, tubulogenesis, angiogenesis, or anti-apoptotic effects. They inhibit both ligand (HGF)-dependent and ligand-independent c-Met pathway activation. Additionally, antibody compounds of the present invention preferentially bind human c-Met extracellular domain (ECD) compared to the ECDs of the closely related receptors RON and PlexinA2, and do not cause "shedding" of the c-Met ECD.

Accordingly, the present invention provides:

A monoclonal antibody, or antigen-binding fragment thereof, that:
a) binds an epitope within the α-chain of human c-Met, and
b) induces internalization of cell surface human c-Met.

Any one of the foregoing antibodies or antigen-binding fragment thereof wherein the antibody or antigen-binding fragment thereof induces hepatocyte-growth factor-independent internalization of cell surface human c-Met. In a preferred embodiment, the monoclonal antibody or antigen-binding fragment thereof comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof that induces internalization of human c-Met in cells comprising a human c-Met variant containing a gain of function mutation. The gain of function mutation can be c-Met kinase domain mutation M1149T or juxtamembrane domain mutation R988c.

Any of the foregoing antibodies or antigen-binding fragments thereof wherein the antibody or antigen-binding fragment thereof induces at least 40% internalization of cell surface human c-Met in cells. Any of the foregoing antibodies or antigen-binding fragments thereof wherein the antibody or antigen-binding fragment thereof induces at least 45% internalization of cell surface human c-Met in cells. Any of the foregoing antibodies or antigen-binding fragments thereof wherein the antibody or antigen-binding fragment thereof induces at least 50% internalization of cell surface human c-Met in cells. Any of the foregoing antibodies or antigen-binding fragments thereof wherein the antibody or antigen-binding fragment thereof induces at least 55% internalization of cell surface human c-Met in cells. Any of the foregoing antibodies or antigen-binding fragments thereof wherein the antibody or antigen-binding fragment thereof induces at least 60% internalization of cell surface human c-Met in cells. Any of the foregoing antibodies or antigen-binding fragments thereof wherein the antibody or antigen-binding fragment thereof induces at least 65% internalization of human c-Met in cells. Any of the foregoing antibodies or antigen-binding fragments thereof wherein the antibody or antigen-binding fragment thereof induces at least 70% internalization of cell surface human c-Met in cells.

Any one of the foregoing monoclonal antibodies or antigen-binding fragments thereof, which induces reduction of total c-Met in hepatocyte growth factor-independent tumor cells. In a preferred embodiment, the monoclonal antibody or antigen-binding fragment thereof which induces reduction of total c-Met in hepatocyte growth factor-independent tumor cells comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof which induces reduction of total c-Met in hepatocyte growth factor-independent tumor cells comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof, which induces reduction of phosphorylated c-Met in hepatocyte growth factor-independent tumor cells.

Any one of the foregoing monoclonal antibodies or antigen-binding fragments thereof, which binds the α-chain of human c-Met at substantially the same epitope as an antibody comprising a light chain having the amino acid sequence shown in SEQ ID NO:28 and a heavy chain having the amino sequence shown in SEQ ID NO:40, or which binds the α-chain of human c-Met at substantially the same epitope as an antibody comprising a light chain having the amino acid sequence shown in SEQ ID NO:29 and a heavy chain having the amino sequence shown in SEQ ID NO:41.

Any one of the foregoing monoclonal antibodies or antigen-binding fragments thereof, excluding those comprising a light chain having the amino acid sequence shown in SEQ ID NO:26 and a heavy chain having the amino sequence shown in SEQ ID NO:38, wherein the epitope comprises one or more amino acid residues within $_{144}$HVFPHNHTADIQS$_{156}$ (SEQ ID NO: 82) inclusive.

Any one of the foregoing antibodies or antigen-binding fragments, wherein the epitope further comprises one or more amino acid residues within $_{123}$DTYYDD$_{128}$ (SEQ ID NO:81) inclusive.

Any one of the foregoing antibodies or antigen-binding fragments, wherein the epitope further comprises one or more amino acid residues within $_{192}$FINF$_{195}$ (SEQ ID NO:83) inclusive.

Any one of the foregoing antibodies or antigen-binding fragments, wherein the epitope further comprises one or more amino acid residues within $_{220}$KETKDGFM$_{227}$ (SEQ ID NO:84) inclusive.

Any one of the foregoing antibodies or antigen-binding fragments thereof, wherein the antibody binds within an amino acid sequence selected from the group consisting of:

a)
$_{121}$VVDTYYDDQL$_{130}$,  (SEQ ID NO: 77)

b)
$_{131}$ISCGSVNRGTCQRHVFPHNHTADIQS$_{156}$,  (SEQ ID NO: 78)

c)
$_{179}$ALGAKVLSSVKDRFINF$_{195}$,  (SEQ ID NO: 79)
and d)
$_{216}$VRRLKETKDGFM$_{227}$,  (SEQ ID NO: 80)
inclusive.

Any one of the foregoing antibodies or antigen-binding fragments thereof, wherein the antibody binds within an amino acid sequence selected from the group consisting of:

a)  $_{123}$DTYYDD$_{128}$,  (SEQ ID NO: 81)

b)  $_{144}$HVFPHNHTADIQS$_{156}$,  (SEQ ID NO: 82)

c)  $_{192}$FINF$_{195}$,  (SEQ ID NO: 83)
and d)  $_{220}$KETKDGFM$_{227}$,  (SEQ ID NO: 84)
inclusive.

Any one of the foregoing monoclonal antibodies or antigen-binding fragments thereof which bind to an amino acid sequence within the epitope characterized by $_{121}$VVDTYYDDQL$_{130}$ (SEQ ID NO:77), $_{131}$ISCGSVNRGTCQRHVFPHNHTADIQS$_{156}$ (SEQ ID NO:78), $_{179}$ALGAKVLSSVKDRFINF$_{195}$ (SEQ ID NO:79), and $_{216}$VRRLKETKDGFM$_{227}$ (SEQ ID NO:80), inclusive.

Any one of the foregoing monoclonal antibodies or antigen-binding fragments thereof which bind to an amino acid sequence within the epitope characterized by $_{123}$DTYYDD$_{128}$ (SEQ ID NO:81), $_{144}$HVFPHNHTADIQS$_{156}$ (SEQ ID NO: 82), $_{192}$FINF$_{195}$ (SEQ ID NO:83), and $_{220}$KETKDGFM$_{227}$ (SEQ ID NO:84) inclusive.

Any one of the foregoing antibodies or antigen-binding fragments thereof, wherein the antibody binds within an amino acid sequence of $_{95}$CFPCQDCSSKA$_{105}$ (SEQ ID NO: 86) inclusive.

Any one of the foregoing monoclonal antibodies or antigen-binding fragments thereof, excluding those comprising a light chain having the amino acid sequence shown in SEQ ID NO:29 and a heavy chain having the amino sequence shown in SEQ ID NO:41, wherein the epitope comprises one or more amino acid residues within $_{95}$CFPCQDCSSKA$_{105}$ (SEQ ID NO: 86) inclusive.

Any one of the foregoing monoclonal antibodies, or antigen-binding fragments thereof, that binds human c-Met, which comprises three light chain complementarity determining regions (LCDRs) and three heavy chain complementarity determining regions (HCDRs),
  wherein said three LCDRs and said three HCDRs are selected from the group consisting of:
    a) LCDR1 comprising the amino acid sequence SVSSSISSTNLH (SEQ ID NO:49);
      LCDR2 comprising the amino acid sequence GTSX$_1$LX$_2$S (SEQ ID NO:87), wherein X$_1$ is Y or R, and X$_2$ is A or R;
      LCDR3 comprising the amino acid sequence QQWSSYPYS (SEQ ID NO:51);
      HCDR1 comprising the amino acid sequence GYTFTSRYIH (SEQ ID NO:59);

HCDR2 comprising the amino acid sequence WIYPVTGDTYYX$_7$EX$_8$FKG (SEQ ID NO:90), wherein X$_7$ is N, I, or R, and X$_8$ is K or P; and HCDR3 comprising the amino acid sequence GYGAFX$_9$Y (SEQ ID NO:91), wherein X$_9$ is Y or F; and b) LCDR1 comprising the amino acid sequence SVSSSVX$_3$SIYLH (SEQ ID NO:88), wherein X$_3$ is S or R;

LCDR2 comprising the amino acid sequence STSNLAS (SEQ ID NO:54); LCDR3 comprising the amino acid sequence X$_4$X$_5$YX$_6$GYPLT (SEQ ID NO:89), wherein X$_4$ is I or Q, X$_5$ is Q or V, and X$_6$ is S or R;

HCDR1 comprising the amino acid sequence GYTFTDYYMH (SEQ ID NO:65);

HCDR2 comprising the amino acid sequence RVNPX$_{10}$RX$_{11}$X$_{12}$TTYNQKFEG (SEQ ID NO:92), wherein X$_{10}$ is N or Y, X$_{11}$ is G or R, and X$_{12}$ is G or S; and HCDR3 comprising the amino acid sequence X$_{13}$NX$_{14}$LDY (SEQ ID NO:93), wherein X$_{13}$ is T or A, and X$_{14}$ is W or I;

wherein said monoclonal antibody or antigen-binding fragment thereof binds an epitope within the α-chain of said human c-Met and induces internalization of cell surface human c-Met.

Any one of the foregoing monoclonal antibodies, or antigen-binding fragments thereof, that binds human c-Met, which comprises three light chain complementarity determining regions (LCDRs) and three heavy chain complementarity determining regions (HCDRs), wherein the antibody comprises three light chain complementarity determining regions (LCDRs) and three heavy chain complementarity determining regions (HCDRs), wherein LCDR1 comprises the amino acid sequence SVSSSISSTNLH (SEQ ID NO:49);

LCDR2 comprises the amino acid sequence GTSX$_1$LX$_2$S (SEQ ID NO:87), wherein X$_1$ is Y or R, and X$_2$ is A or R;

LCDR3 comprises the amino acid sequence QQWSSYPYS (SEQ ID NO:51);

HCDR1 comprises the amino acid sequence GYTFTSRYIH (SEQ ID NO:59);

HCDR2 comprises the amino acid sequence WIYPVTGDTYYX$_7$EX$_8$FKG (SEQ ID NO:90), wherein X$_7$ is N, I, or R, and X$_8$ is K or P; and HCDR3 comprises the amino acid sequence GYGAFX$_9$Y (SEQ ID NO:91), wherein X$_9$ is Y or F.

Any one of the foregoing monoclonal antibodies, or antigen-binding fragments thereof, that binds human c-Met, which comprises three light chain complementarity determining regions (LCDRs) and three heavy chain complementarity determining regions (HCDRs), wherein LCDR1 comprises the amino acid sequence SVSSSVX$_3$SIYLH (SEQ ID NO:88); wherein X$_3$ is S or R;
LCDR2 comprises the amino acid sequence STSNLAS (SEQ ID NO:54);
LCDR3 comprises the amino acid sequence X$_4$X$_5$YX$_6$GYPLT (SEQ ID NO:89), wherein
X$_4$ is I or Q, X$_5$ is Q or V, and X$_6$ is S or R;
HCDR1 comprises the amino acid sequence GYTFTDYYMH (SEQ ID NO:65);
HCDR2 comprises the amino acid sequence RVNPX$_{10}$RX$_{11}$X$_{12}$TTYNQKFEG (SEQ ID NO:92), wherein X$_{10}$ is N or Y, X$_{11}$ is G or R, and X$_{12}$ is G or S; and
HCDR3 comprises the amino acid sequence X$_{13}$NX$_{14}$LDY (SEQ ID NO:93), wherein X$_{13}$ is T or A, and X$_{14}$ is W or I.

Any one of the foregoing monoclonal antibodies, or antigen-binding fragments thereof, that binds human c-Met, which comprises three light chain complementarity determining regions (LCDRs) and three heavy chain complementarity determining regions (HCDRs), and
wherein said three LCDRs and said three HCDRs are selected from the group consisting of:
 a) LCDR1 comprising the amino acid sequence SVSSSISSTNLH (SEQ ID NO:49);
   LCDR2 comprising the amino acid sequence GTSYLAS (SEQ ID NO:50);
   LCDR3 comprising the amino acid sequence QQWSSYPYS (SEQ ID NO:51);
   HCDR1 comprising the amino acid sequence GYTFTSRYIH (SEQ ID NO:59);
   HCDR2 comprising the amino acid sequence WIYPVTGDTYYNEKFKG (SEQ ID NO:60); and
   HCDR3 comprising the amino acid sequence GYGAFYY (SEQ ID NO:61);
 b) LCDR1 comprising the amino acid sequence SVSSSISSTNLH (SEQ ID NO:49);
   LCDR2 comprising the amino acid sequence GTSYLAS (SEQ ID NO:50);
   LCDR3 comprising the amino acid sequence QQWSSYPYS (SEQ ID NO:51);
   HCDR1 comprising the amino acid sequence GYTFTSRYIH (SEQ ID NO:59);
   HCDR2 comprising the amino acid sequence WIYPVTGDTYYIEKFKG (SEQ ID NO:62); and
   HCDR3 comprising the amino acid sequence GYGAFFY (SEQ ID NO:63);
 c) LCDR1 comprising the amino acid sequence SVSSSISSTNLH (SEQ ID NO:49);
   LCDR2 comprising the amino acid sequence GTSRLRS (SEQ ID NO:52);
   LCDR3 comprising the amino acid sequence QQWSSYPYS (SEQ ID NO:51);
   HCDR1 comprising the amino acid sequence GYTFTSRYIH (SEQ ID NO:59);
   HCDR2 comprising the amino acid sequence WIYPVTGDTYYREPFKG (SEQ ID NO:64), and
   HCDR3 comprising the amino acid sequence GYGAFYY (SEQ ID NO:61);
 d) LCDR1 comprising the amino acid sequence SVSSSVSSIYLH (SEQ ID NO:53); LCDR2 comprising the amino acid sequence STSNLAS (SEQ ID NO:54);
   LCDR3 comprising the amino acid sequence IQYSGYPLT (SEQ ID NO:55);
   HCDR1 comprising the amino acid sequence GYTFTDYYMH (SEQ ID NO:65);
   HCDR2 comprising the amino acid sequence RVNPNRGGTTYNQKFEG (SEQ ID NO:66), and
   HCDR3 comprising the amino acid sequence TNWLDY (SEQ ID NO:67);
 e) LCDR1 comprising the amino acid sequence SVSSSVSSIYLH (SEQ ID NO:53);
   LCDR2 comprising the amino acid sequence STSNLAS (SEQ ID NO:54);
   LCDR3 comprising the amino acid sequence QVYSGYPLT (SEQ ID NO:56);
   HCDR1 comprising the amino acid sequence GYTFTDYYMH (SEQ ID NO:65);
   HCDR2 comprising the amino acid sequence RVNPNRRGTTYNQKFEG (SEQ ID NO:68); and
   HCDR3 comprising the amino acid sequence ANWLDY (SEQ ID NO:69); and f) LCDR1 comprising the amino acid sequence SVSSSVRSIYLH (SEQ ID NO:57);
   LCDR2 comprising the amino acid sequence STSNLAS (SEQ ID NO:54);
   LCDR3 comprising the amino acid sequence QVYRGYPLT (SEQ ID NO:58);
   HCDR1 comprising the amino acid sequence GYTFTDYYMH (SEQ ID NO:65);
   HCDR2 comprising the amino acid sequence RVNPYRGSTTYNQKFEG (SEQ ID NO:70); and
   HCDR3 comprising the amino acid sequence ANILDY (SEQ ID NO:71); and
   wherein said monoclonal antibody or antigen-binding fragment thereof binds an epitope within the α-chain of said human c-Met and induces internalization of cell surface human c-Met.

Any one of the foregoing monoclonal antibodies or antigen-binding fragments thereof comprising three light chain complementarity determining regions (LCDRs) and three heavy chain complementarity determining regions (HCDRs), wherein said three LCDRs and said three HCDRs are selected from the group consisting of:
   a) LCDR1 comprising the amino acid sequence SVSSSISSTNLH (SEQ ID NO:49);
      LCDR2 comprising the amino acid sequence GTSYLAS (SEQ ID NO:50);
      LCDR3 comprising the amino acid sequence QQWSSYPYS (SEQ ID NO:51);
      HCDR1 comprising the amino acid sequence GYTFTSRYIH (SEQ ID NO:59);
      HCDR2 comprising the amino acid sequence WIYPVTGDTYYNEKFKG (SEQ ID NO:60); and
      HCDR3 comprising the amino acid sequence GYGAFYY (SEQ ID NO:61);
   b) LCDR1 comprising the amino acid sequence SVSSSISSTNLH (SEQ ID NO:49);
      LCDR2 comprising the amino acid sequence GTSYLAS (SEQ ID NO:50);
      LCDR3 comprising the amino acid sequence QQWSSYPYS (SEQ ID NO:51);
      HCDR1 comprising the amino acid sequence GYTFTSRYIH (SEQ ID NO:59);
      HCDR2 comprising the amino acid sequence WIYPVTGDTYYIEKFKG (SEQ ID NO:62); and
      HCDR3 comprising the amino acid sequence GYGAFFY (SEQ ID NO:63);
   c) LCDR1 comprising the amino acid sequence SVSSSISSTNLH (SEQ ID NO:49);
      LCDR2 comprising the amino acid sequence GTSRLRS (SEQ ID NO:52);
      LCDR3 comprising the amino acid sequence QQWSSYPYS (SEQ ID NO:51);
      HCDR1 comprising the amino acid sequence GYTFTSRYIH (SEQ ID NO:59);
      HCDR2 comprising the amino acid sequence WIYPVTGDTYYREPFKG (SEQ ID NO:64); and
      HCDR3 comprising the amino acid sequence GYGAFYY (SEQ ID NO:61).

Any one of the foregoing monoclonal antibodies or antigen-binding fragments thereof comprising three light chain complementarity determining regions (LCDRs) and three heavy chain complementarity determining regions (HCDRs), wherein said three LCDRs and said three HCDRs are selected from the group consisting of:
   a) LCDR1 comprising the amino acid sequence SVSSSVSSIYLH (SEQ ID NO:53);
      LCDR2 comprising the amino acid sequence STSNLAS (SEQ ID NO:54);
      LCDR3 comprising the amino acid sequence IQYSGYPLT (SEQ ID NO:55);
      HCDR1 comprising the amino acid sequence GYTFTDYYMH (SEQ ID NO:65);
      HCDR2 comprising the amino acid sequence RVNPNRGGTTYNQKFEG (SEQ ID NO:66); and
      HCDR3 comprising the amino acid sequence TNWLDY (SEQ ID NO:67);
   b) LCDR1 comprising the amino acid sequence SVSSSVSSIYLH (SEQ ID NO:53);
      LCDR2 comprising the amino acid sequence STSNLAS (SEQ ID NO:54);
      LCDR3 comprising the amino acid sequence QVYSGYPLT (SEQ ID NO:56);
      HCDR1 comprising the amino acid sequence GYTFTDYYMH (SEQ ID NO:65);
      HCDR2 comprising the amino acid sequence RVNPNRRGTTYNQKFEG (SEQ ID NO:68); and
      HCDR3 comprising the amino acid sequence ANWLDY (SEQ ID NO:69); and
   c) LCDR1 comprising the amino acid sequence SVSSSVRSIYLH (SEQ ID NO:57);
      LCDR2 comprising the amino acid sequence STSNLAS (SEQ ID NO:54);
      LCDR3 comprising the amino acid sequence QVYRGYPLT (SEQ ID NO:58);
      HCDR1 comprising the amino acid sequence GYTFTDYYMH (SEQ ID NO:65); HCDR2 comprising the amino acid sequence RVNPYRGSTTYNQKFEG (SEQ ID NO:70); and
      HCDR3 comprising the amino acid sequence ANILDY (SEQ ID NO:71).

Any one of the foregoing monoclonal antibodies, or antigen-binding fragments thereof comprising three light chain complementarity determining regions (LCDRs) and three heavy chain complementarity determining regions (HCDRs), wherein:
   LCDR1 comprising the amino acid sequence SVSSSVSSIYLH (SEQ ID NO:53);
   LCDR2 comprising the amino acid sequence STSNLAS (SEQ ID NO:54);
   LCDR3 comprising the amino acid sequence IQYSGYPLT (SEQ ID NO:55);
   HCDR1 comprising the amino acid sequence GYTFTDYYMH (SEQ ID NO:65);
   HCDR2 comprising the amino acid sequence RVNPNRGGTTYNQKFEG (SEQ ID NO:66); and
   HCDR3 comprising the amino acid sequence TNWLDY (SEQ ID NO:67);

Any one of the foregoing monoclonal antibodies, or antigen-binding fragments thereof comprising three light chain complementarity determining regions (LCDRs) and three heavy chain complementarity determining regions (HCDRs), wherein:
   LCDR1 comprises the amino acid sequence SVSSSVSSIYLH (SEQ ID NO:53);
   LCDR2 comprises the amino acid sequence STSNLAS (SEQ ID NO:54);
   LCDR3 comprises the amino acid sequence QVYSGYPLT (SEQ ID NO:56);
   HCDR1 comprises the amino acid sequence GYTFTDYYMH (SEQ ID NO:65);
   HCDR2 comprises the amino acid sequence RVNPNRRGTTYNQKFEG (SEQ ID NO:68); and HCDR3 comprises the amino acid sequence ANWLDY (SEQ ID NO:69).

Any one of the foregoing monoclonal antibodies, or antigen-binding fragments thereof, comprising a light chain variable region (LCVR) and a heavy chain variable region (HCVR), wherein said LCVR and said HCVR, respectively, comprise amino acid sequences selected from the group consisting of:
 a) SEQ ID NO:94 and SEQ ID NO:96; and
 b) SEQ ID NO:95 and SEQ ID NO:97,
 wherein said monoclonal antibody or antigen-binding fragment thereof binds an epitope within the α-chain of said human c-Met and induces internalization of cell surface human c-Met.

Any one of the foregoing monoclonal antibodies, or antigen-binding fragments thereof comprising a light chain variable region (LCVR) and a heavy chain variable region (HCVR), wherein said LCVR comprises SEQ ID NO:94 and said HCVR comprises SEQ ID NO:96.

Any one of the foregoing monoclonal antibodies, or antigen-binding fragments thereof comprising a light chain variable region (LCVR) and a heavy chain variable region (HCVR), wherein said LCVR comprises SEQ ID NO:95 and said HCVR comprises SEQ ID NO:97.

Any one of the foregoing monoclonal antibodies or antigen-binding fragments thereof, wherein said LCVR and said HCVR comprise amino acid sequences which are selected from the group consisting of:
 a) LCVR is SEQ ID NO:1 and HCVR is SEQ ID NO:13;
 b) LCVR is SEQ ID NO:2 and HCVR is SEQ ID NO:14;
 c) LCVR is SEQ ID NO:3 and HCVR is SEQ ID NO:15;
 d) LCVR is SEQ ID NO:4 and HCVR is SEQ ID NO:16;
 e) LCVR is SEQ ID NO:5 and HCVR is SEQ ID NO:17; and
 f) LCVR is SEQ ID NO:6 and HCVR is SEQ ID NO:18.

Any one of the foregoing monoclonal antibodies or antigen-binding fragments thereof, wherein said LCVR and said HCVR, respectively, comprise amino acid sequences selected from the group consisting of:
 a) LCVR is SEQ ID NO:1 and HCVR is SEQ ID NO:13;
 b) LCVR is SEQ ID NO:2 and HCVR is SEQ ID NO:14; and
 c) LCVR is SEQ ID NO:3 and HCVR is SEQ ID NO:15.

Any one of the foregoing monoclonal antibodies or antigen-binding fragments thereof, wherein said LCVR and said HCVR, respectively, comprise amino acid sequences selected from the group consisting of:
 a) LCVR is SEQ ID NO:4 and HCVR is SEQ ID NO:16;
 b) LCVR is SEQ ID NO:5 and HCVR is SEQ ID NO:17; and
 c) LCVR is SEQ ID NO:6 and HCVR is SEQ ID NO:18.

Any one of the foregoing monoclonal antibodies or antigen-binding fragments thereof, wherein said LCVR comprises the amino acid sequence of SEQ ID NO: 4 and said HCVR comprises the amino acid sequence of SEQ ID NO: 16.

Any one of the foregoing monoclonal antibodies or antigen-binding fragments thereof, wherein said LCVR comprises the amino acid sequence of SEQ ID NO: 5 and said HCVR comprises the amino acid sequence of SEQ ID NO: 17.

Any one of the foregoing monoclonal antibodies wherein said antibody comprises a light chain and a heavy chain wherein the light chain and the heavy chain comprise amino acid sequences which are selected from the group consisting of:
 a) light chain is SEQ ID NO:25 and heavy chain is SEQ ID NO:37;
 b) light chain is SEQ ID NO:26 and heavy chain is SEQ ID NO:38;
 c) light chain is SEQ ID NO:27 and heavy chain is SEQ ID NO:39;
 d) light chain is SEQ ID NO:28 and heavy chain is SEQ ID NO:40;
 e) light chain is SEQ ID NO:29 and heavy chain is SEQ ID NO:41; and
 f) light chain is SEQ ID NO:30 and heavy chain is SEQ ID NO:42.

Any one of the foregoing monoclonal antibodies wherein said antibody comprises a light chain and a heavy chain wherein the light chain and the heavy chain comprise amino acid sequences which are selected from the group consisting of
 a) light chain is SEQ ID NO:25 and heavy chain is SEQ ID NO:37;
 b) light chain is SEQ ID NO:26 and heavy chain is SEQ ID NO:38; and
 c) light chain is SEQ ID NO:27 and heavy chain is SEQ ID NO:39.

Any one of the foregoing monoclonal antibodies wherein said antibody comprises a light chain and a heavy chain wherein the light chain and the heavy chain comprise amino acid sequences which are selected from the group consisting of:
 a) light chain is SEQ ID NO:28 and heavy chain is SEQ ID NO:40;
 b) light chain is SEQ ID NO:29 and heavy chain is SEQ ID NO:41; and
 c) light chain is SEQ ID NO:30 and heavy chain is SEQ ID NO:42.

Any one of the foregoing monoclonal antibodies wherein said light chain comprises the amino acid sequence of SEQ ID NO: 28 and said heavy chain comprises the amino acid sequence of SEQ ID NO: 40.

Any one of the foregoing monoclonal antibodies wherein said light chain comprises the amino acid sequence of SEQ ID NO: 29 and said heavy chain comprises the amino acid sequence of SEQ ID NO: 41.

Any one of the foregoing monoclonal antibodies wherein said antibody comprises two light chains and two heavy chains, wherein each light chain comprises the amino acid sequence of SEQ ID NO: 28 and each heavy chain comprises the amino acid sequence of SEQ ID NO: 40.

Any one of the foregoing monoclonal antibodies wherein said antibody comprises two light chains and two heavy chains, wherein each light chain comprises the amino acid sequence of SEQ ID NO: 29 and each heavy chain comprises the amino acid sequence of SEQ ID NO: 41.

A monoclonal antibody or antigen-binding fragment thereof that competes with any of the foregoing c-Met monoclonal antibodies or antigen-binding fragments thereof for binding to c-Met. Such competing monoclonal antibody or antigen-binding fragment thereof can bind to the same epitope of c-Met as any one of the foregoing c-Met monoclonal antibodies or antigen-binding fragments thereof. In a preferred embodiment, the monoclonal antibody or antigen-binding fragment thereof competes with an antibody which comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof competes with an antibody which comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof, which induces reduction of total human c-Met and phosphorylated human c-Met in hepatocyte growth factor-independent tumor cells that constitutively overexpress said human c-Met. In a preferred embodiment, the monoclonal antibody or antigen-binding fragment thereof which induces reduction of total human c-Met and phosphorylated human c-Met in hepatocyte growth factor-independent tumor cells that constitutively overexpress said human c-Met, comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof which induces reduction of total human c-Met and phosphorylated human c-Met in hepatocyte growth factor-independent tumor cells that constitutively overexpress said human c-Met, comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof, which induces reduction of total human c-Met and phosphorylated human c-Met in hepatocyte growth factor-independent tumor cells that constitutively phosphorylate said human c-Met. In a preferred embodiment, the monoclonal antibody or antigen-binding fragment thereof which induces reduction of total human c-Met and phosphorylated human c-Met in hepatocyte growth factor-independent tumor cells that constitutively phosphorylate said human c-Met, comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof which induces reduction of total human c-Met and phosphorylated human c-Met in hepatocyte growth factor-independent tumor cells that constitutively phosphorylate said human c-Met, comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof, which induces reduction of total human c-Met and phosphorylated human c-Met in hepatocyte growth factor-independent tumor cells that are hepatocyte growth factor-responsive.

Any one of the foregoing monoclonal antibodies or antigen-binding fragments thereof, which preferentially binds human c-Met extracellular domain compared to human RON extracellular domain or human PlexinA2 extracellular domain.

Any one of the foregoing monoclonal antibodies or antigen-binding fragments thereof, which does not induce shedding of human c-Met extracellular domain. In a preferred embodiment, the monoclonal antibody or antigen-binding fragment thereof which does not induce shedding of human c-Met extracellular domain, comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof which does not induce shedding of human c-Met extracellular domain, comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof, which does not protect tumor cells expressing human c-Met from staurosporine-induced apoptosis. In a preferred embodiment, the monoclonal antibody or antigen-binding fragment thereof which does not protect tumor cells expressing human c-Met from staurosporine-induced apoptosis, comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof which does not protect tumor cells expressing human c-Met from staurosporine-induced apoptosis, comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof, which inhibits hepatocyte growth factor-dependent and hepatocyte growth factor-independent proliferation of tumor cells that express human c-Met.

Any one of the foregoing monoclonal antibodies or antigen-binding fragments thereof, which inhibits binding of human hepatocyte growth factor to human c-Met.

Any one of the foregoing monoclonal antibodies or antigen-binding fragments thereof which does not induce HGF-like biological agonist activities. HGF-like biological agonist activities include tumor cell proliferation, tumor cell motility, tumor cell invasion, tubulogenesis, angiogenesis, and anti-apoptotic effects. In a preferred embodiment, the monoclonal antibody or antigen-binding fragment thereof which does not induce HGF-like biological agonist activities, comprises a light chain and a heavy chain, wherein the light chain comprises the amino acid sequence of SEQ ID NO: 29 and the heavy chain comprises the amino acid sequence of SEQ ID NO: 41.

A pharmaceutical composition, comprising any one of the foregoing monoclonal antibodies or antigen-binding fragments thereof, and a pharmaceutically acceptable carrier, diluent, or excipient.

Any one of the foregoing monoclonal antibodies or antigen-binding fragments thereof for use in therapy. In a preferred embodiment, the monoclonal antibody or antigen-binding fragment thereof for use in therapy comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof for use in therapy comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof for use in treating a cancer in a human. In a preferred embodiment, the monoclonal antibody or antigen-binding fragment thereof for use in treating a cancer in a human comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof for use in treating a cancer in a human comprises a light chain and a heavy chain, wherein the light chain comprises the amino acid sequence of SEQ ID NO: 29 and the heavy chain comprises the amino acid sequence of SEQ ID NO: 41.

Any one of the foregoing monoclonal antibodies or antigen-binding fragments thereof for use in treating a cancer in a human in combination with another therapeutic agent. In a preferred embodiment, the monoclonal antibody or antigen-binding fragment thereof for use in treating a cancer in a human in combination with another therapeutic comprises a light chain and a heavy chain, wherein the light chain comprises the amino acid sequence of SEQ ID NO: 28 and the heavy chain comprises the amino acid sequence of SEQ ID NO: 40. In another preferred embodiment, the monoclonal antibody or antigen-binding fragment thereof for use in treating a cancer in a human in combination with another therapeutic comprises a light chain and a heavy chain, wherein the light chain comprises the amino acid sequence of SEQ ID NO: 29 and the heavy chain comprises the amino acid sequence of SEQ ID NO: 41.

A pharmaceutical composition comprising any one of the foregoing monoclonal antibodies or antigen-binding fragments thereof and a pharmaceutically acceptable carrier, diluent, or excipient.

Use of any one of the foregoing monoclonal antibodies or antigen-binding fragments thereof for the manufacture of a medicament for treating a cancer in a human.

A method of treating a cancer, comprising administering to a human patient in need thereof an effective amount of any one of the foregoing monoclonal antibodies or antigen-binding fragments thereof.

DEFINITIONS

A full-length antibody as it exists naturally is an immunoglobulin molecule comprising 2 heavy (H) chains and 2 light (L) chains interconnected by disulfide bonds. The amino terminal portion of each chain includes a variable region of about 100-110 or more amino acids primarily responsible for antigen recognition via the complementarity determining regions (CDRs) contained therein. The carboxy-terminal portion of each chain defines a constant region primarily responsible for effector function.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions are in accordance with the well-known Kabat numbering convention.

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is characterized by a particular constant region with a sequence well known in the art.

As used herein, the term "monoclonal antibody" (Mab) as applied to the present antibody compounds refers to an antibody that is derived from a single copy or clone including, for example, any eukaryotic, prokaryotic, or phage clone, and not the method by which it is produced. Mabs of the present invention preferably exist in a homogeneous or substantially homogeneous population. Complete Mabs contain 2 heavy chains and 2 light chains. "Antigen-binding fragments" of such monoclonal antibodies include, for example, Fab fragments, Fab' fragments, F(ab')$_2$ fragments, single chain Fv fragments, and one-armed antibodies comprising a light chain and a heavy chain. Monoclonal antibodies and antigen-binding fragments thereof of the present invention can be produced, for example, by recombinant technologies, phage display technologies, synthetic technologies, e.g., CDR-grafting, or combinations of such technologies, or other technologies known in the art.

"Antibody compounds" refers to Mabs and Fabs disclosed herein. Additional antibody compounds exhibiting similar functional properties according to the present invention can be generated by conventional methods. For example, mice can be immunized with human c-Met or fragments thereof, the resulting antibodies can be recovered and purified, and determination of whether they possess binding and functional properties similar to or the same as the antibody compounds disclosed herein can be assessed by the methods disclosed in Examples 2-19, below. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

The phrase "human engineered antibodies" refers to monoclonal antibodies and antigen-binding fragments in addition to the antibody compounds disclosed herein that have binding and functional properties according to the invention similar to those disclosed herein, and that have framework regions that are substantially human or fully human surrounding CDRs derived from a non-human antibody. "Framework region" or "framework sequence" refers to any one of framework regions 1 to 4. Human engineered antibodies and antigen-binding fragments encompassed by the present invention include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, about 90%, about 95%, or about 99% sequence identity to a known human germline framework sequence.

Fully human frameworks are those that are identical to a known human germline framework sequence. Human framework germline sequences can be obtained from ImMunoGeneTics (IMGT) via their website or from *The Immunoglobulin FactsBook* by Marie-Paule Lefranc and Gerard Lefranc, Academic Press, 2001, ISBN 012441351. For example, germline light chain frameworks can be selected from the group consisting of: A11, A17, A18, A19, A20, A27, A30, LI, L1I, L12, L2, L5, L15, L6, L8, O12, O2, and O8, and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-5I.

Human engineered antibodies in addition to those disclosed herein exhibiting similar functional properties according to the present invention can be generated using several different methods. In one approach, the parent antibody compound CDRs are grafted into a human framework that has a high sequence identity with the parent antibody compound framework. The sequence identity of the new framework will generally be at least about 80%, at least about 85%, at least about 90%, at least about 95%, or at least about 99% identical to the sequence of the corresponding framework in the parent antibody compound. In the case of frameworks having fewer than 100 amino acid residues, one, two, or three amino acid residues can be changed. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful in humanizing mouse antibodies include U.S. Pat. Nos. 4,816,397; 5,225,539, and 5,693,761; computer programs ABMOD and ENCAD as described in Levitt (1983) *J. Mol. Biol.* 168:595-620; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as follows.

When an amino acid falls under the following category, the framework amino acid of the human germ-line sequence that is being used (the "acceptor framework") is replaced by a framework amino acid from a framework of the parent antibody compound (the "donor framework"):

(a) the amino acid in the human framework region of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating human engineered antibodies exhibiting similar functional properties to the antibody compounds disclosed herein involves randomly mutating amino acids within the grafted CDRs without changing the framework, and screening the resultant molecules for binding affinity and other functional properties that are as good as or better than those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu et al. (1999) *J. Mol. Biol.* 294:151-162.

Applying the teachings of the present invention, a person skilled in the art can use common techniques, e.g., site-directed mutagenesis, to substitute amino acids within the presently disclosed CDR and framework sequences and thereby generate further variable region amino acid sequences derived from the present sequences. Up to all naturally occurring amino acids can be introduced at a specific substitution site. The methods disclosed herein can then be used to screen these additional variable region amino acid sequences to identify sequences having the indicated in vivo functions. In this way, further sequences suitable for preparing human engineered antibodies and antigen-binding portions thereof in accordance with the present invention can be identified. Preferably, amino acid substitution within the frameworks is restricted to one, two, or three positions within any one or more of the 4 light chain and/or heavy chain framework regions disclosed herein. Preferably, amino acid substitution within the CDRs is restricted to one, two, or three positions within any one or more of the 3 light chain and/or heavy chain CDRs. Combinations of the various changes within these framework regions and CDRs described above are also possible.

That the functional properties of the antibody compounds generated by introducing the amino acid modifications discussed above conform to those exhibited by the specific molecules disclosed herein can be confirmed by the methods disclosed below in Examples 2-19.

The term "epitope" refers to a specific arrangement of amino acids located on a peptide or protein to which an antibody or antibody fragment binds. Epitopes often consist of a chemically active surface grouping of molecules such as amino acids or sugar side chains, and have specific three dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous. The epitopes disclosed herein can consist of, consist essentially of, or comprise the amino acid sequences disclosed in Example 3.

Monoclonal antibodies or antigen-binding fragments thereof that "compete" with the molecules disclosed herein are those that bind human c-Met at site(s) that are identical to, or overlapping with, the site(s) at which the present molecules bind. Competing monoclonal antibodies or antigen-binding fragments thereof can be identified, for example, via an antibody competition assay. For example, a sample of purified or partially purified human c-Met can be bound to a solid support. Then, an antibody compound or antigen binding fragment thereof of the present invention and a monoclonal antibody or antigen-binding fragment thereof suspected of being able to compete with such invention antibody compound are added. One of the two molecules is labeled. If the labeled compound and the unlabeled compound bind to separate and discrete sites on c-Met, the labeled compound will bind to the same level whether or not the suspected competing compound is present. However, if the sites of interaction are identical or overlapping, the unlabeled compound will compete, and the amount of labeled compound bound to the antigen will be lowered. If the unlabeled compound is present in excess, very little, if any, labeled compound will bind. For purposes of the present invention, competing monoclonal antibodies or antigen-binding fragments thereof are those that decrease the binding of the present antibody compounds to c-Met by about 50%, about 60%, about 70%, about 80%, about 85%, about 90%, about 95%, or about 99%. Details of procedures for carrying out such competition assays are well known in the art and can be found, for example, in Harlow and Lane (1988) *Antibodies, A Laboratory Manual*, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared. Whether monoclonal antibodies or antigen-binding fragments thereof that compete with antibody compounds of the present invention in such competition assays possess the same or similar functional properties of the present antibody compounds can be determined via the methods disclosed in Examples 2-19 herein.

Monoclonal antibodies or antigen-binding fragments thereof that bind substantially the same epitope(s) of c-Met as the monoclonal antibodies or antigen-binding fragments disclosed herein are those that bind human c-Met at site(s) that are overlapping with the site(s) at which the present molecules bind. Methods that facilitate identification of monoclonal antibodies or antigen-binding fragments thereof that bind substantially the same epitope of c-Met as the c-Met monoclonal antibodies or antigen-binding fragments disclosed herein are well known in the art and are described, for example, in PCT International Publication WO 00/64946. Whether such monoclonal antibodies or antigen-binding fragments thereof that bind substantially the same c-Met epitope(s) as those disclosed herein possess the same or similar functional properties of the present antibody compounds can be determined via the methods disclosed in Examples 2-19 herein.

"c-Met" or "human c-Met" refers to any human c-Met, as well as functionally active, mutated forms thereof. The structure of the c-Met is depicted schematically as:

SEMA: Sema domain
PSI: Plexin, Semaphorins, and Integrins domain
IPT: 4 Immunoglobulins, Plexins, and Transcription factor domains
TM: Transmembrane region
JM: Juxtamembrane domain
KD: Kinase domain In the human c-Met ECD (SEQ ID NO:75), amino acids 1-24 comprise the signal sequence. The mature protein begins at amino acid 25 (E). The Sema domain consists of approximately 500 amino acid residues at the N-terminus of c-Met, and contains the α-chain (amino acid residues 25-307) and part of the β-chain (amino acid residues 308-519).

The term "inhibit" means the ability to substantially antagonize, prohibit, prevent, restrain, slow, disrupt, eliminate, stop, reduce, or reverse the biological effects of c-Met.

The term "treating" (or "treat" or "treatment") means slowing, interrupting, arresting, controlling, stopping, reducing, or reversing the progression or severity of a symptom, disorder, condition, or disease, but does not necessarily involve a total elimination of all disease-related symptoms, conditions, or disorders.

Acute events and chronic conditions may be treated. In an acute event, an antibody or antigen-binding fragment thereof is administered at the onset of a symptom, disorder, condition, or disease, and is discontinued when the acute event ends. In contrast, a chronic symptom, disorder, condition, or disease is treated over a more protracted time frame.

The term "effective amount" refers to the amount or dose of an antibody compound of the present invention which, upon single or multiple dose administration to a patient, provides the desired treatment or prevention. Therapeutically effective amounts of the present antibody compounds can comprise an amount in the range of from about 0.1 mg/kg to about 20 mg/kg per single dose. A therapeutically effective amount for any individual patient can be determined by the health care provider by monitoring the effect of the antibody compounds on a biomarker, such as cell surface c-Met in tumor or non-tumor tissues, tumor regression, etc. Analysis of the data obtained by these methods permits modification of the treatment regimen during therapy so that optimal amounts of antibody compounds, whether employed alone or in combination with one another therapeutic agent, are administered, and so that the duration of treatment can be determined as well. In this way, the dosing/treatment regimen can be modified over the course of therapy so that the lowest amounts of antibody compounds used alone or in combination that exhibit satisfactory tumor reducing effectiveness are administered, and so that administration of such compounds is continued only so long as is necessary to successfully treat the patient.

The antibody compounds of the present invention can be used as medicaments in human medicine, administered by a variety of routes. Most preferably, such compositions are for parenteral administration. Such pharmaceutical compositions can be prepared by methods well known in the art. See, e.g., *Remington: The Science and Practice of Pharmacy*, 19$^{th}$ ed. (1995), A. Gennaro et al., Mack Publishing Co., and comprise one or more antibody compounds disclosed herein, and a pharmaceutically acceptable carrier, diluent, or excipient.

The term "tumor" refers to all neoplastic cell growth and proliferation, whether malignant or benign, and all pre-cancerous and cancerous cells and tissues. The terms "cancer", "cancerous", and "tumor" are not mutually exclusive as used herein.

The terms "cancer" and "cancerous" refer to or describe the physiological condition in mammals that is typically characterized by aberrant cell growth/proliferation. Examples of cancers include, but are not limited to, carcinomas, lymphomas, blastomas, sarcomas, and leukemias.

c-Met and Cancer

Deregulated c-Met pathways can be induced by transcriptional up regulation, c-Met gene amplification, specific genetic alterations, or ligand-dependent autocrine or paracrine mechanisms. The most frequent cause of constitutive c-Met activation in human tumors is increased protein expression as a consequence of transcriptional upregulation, in the absence of gene amplification. In addition, amplification of the MET gene, with consequent protein overexpression and constitutive kinase activation, has been reported in a number of human primary tumors, including gastric and oesophageal carcinomas, non-small-cell lung (NSCL) carcinomas, and medulloblastomas. Tumors of mesenchymal origin, such as osteosarcomas and rhabdomyosarcomas, often utilize autocrine mechanisms by producing HGF. Elevated HGF levels and overexpression of c-Met are often associated with poor clinical outcomes that include more aggressive disease, increased tumor metastasis, and shortened patient survival. Further, high levels of HGF and/or c-Met proteins in tumors confer resistance to chemotherapy and radiotherapy. In addition to abnormal HGF and c-Met expression, the c-Met pathway can be activated through genetic alternations such as c-Met mutations, gene amplification, and gene rearrangement. Missense c-MET mutations are found in all individuals with well-characterized hereditary papillary renal cell carcinomas (PRCC) and in a small subset (13%) of sporadic PRCC samples. Some of the mutations possess oncogenic potential due to increased kinase activity. Trisomy of chromosome 7, where both HGF and c-MET genes reside, occurs frequently in PRCC, and results in non-random duplication of the mutant c-MET allele. In addition, somatic c-MET mutations have been identified in other human cancers, including gastric, head and neck, liver, ovarian, non-small cell lung and thyroid cancers, as well as in metastases of some of these cancers. Unlike PRCC, where mutations are typically confined to the kinase domain, these mutations are often located in other regions of the receptor, for example, the juxtamembrane domain. In addition to mutation, the c-MET gene is often amplified in breast, liver, brain, colorectal, gastric, lung and stomach cancers, which is correlated to disease progression in some patients.

Therapeutic Indications

Aberrant HGF/c-MET signaling has been documented in a wide range of human malignancies, including bladder, breast, cervical, colorectal, endometrial, esophageal, gastric, head and neck, kidney, liver, lung, nasopharyngeal, ovarian, pancreatic, prostate and thyroid cancers, as well as cholangiocarcinoma, osteosarcoma, rhabdomyosarcoma, synovial sarcoma, Kaposi's sarcoma, leiomyosarcomas, and MFH/fibrosarcoma. In addition, abnormal HGF and/or c-Met expression has also been reported in hematological malignancies such as acute myelogenous leukemia, adult T-cell leukemia, chronic myeloid leukemia, lymphomas and multiple myeloma, as well as other tumors such as melanoma, mesothelioma, Wilms' tumor, glioblastomata, and astrocytomas (summarized in Liu et al. (2008) *Expert Opin. Investig. Drugs* 17(7):997-1011). The c-Met antibodies of the present invention can inhibit both HGF-dependent and HGF-independent tumors.

The following non-limiting examples illustrate various aspects of the present invention.

In the examples below, the humanized IgG2 and IgG4 and murine IgG (also sometimes referred to as mIgG1) control antibodies are isotype control antibodies unrelated to the present c-Met antibodies. Antibodies C8, D11, and optD11 are murine antibodies. In all cases, human HGF is obtained from R&D Systems (#294).

EXAMPLE 1 c-Met Antibodies

The amino acid sequences of the light chain and heavy chain variable regions, the complete light and heavy chains, and the respective encoding nucleotide sequences of the foregoing, of the present human engineered antibodies are listed below in the section entitled "Amino Acid and Nucleotide Sequences." The light chain and heavy chain CDR amino acid sequences are shown in Tables 1 and 2, respectively.

TABLE 1

Light Chain CDRs

| Antibody | CDR 1 | CDR 2 | CDR 3 |
|---|---|---|---|
| D11-S17Y | SVSSSISSTNLH (SEQ ID NO: 49) | GTSYLAS (SEQ ID NO: 50) | QQWSSYPYS (SEQ ID NO: 51) |
| D11-8B8 | SVSSSISSTNLH (SEQ ID NO: 49) | GTSYLAS (SEQ ID NO: 50) | QQWSSYPYS (SEQ ID NO: 51) |
| D11-C27G3 | SVSSSISSTNLH (SEQ ID NO: 49) | GTSRLRS (SEQ ID NO: 52) | QQWSSYPYS (SEQ ID NO: 51) |
| D11 Consensus Sequence | — | GTSX$_1$LX$_2$S (SEQ ID NO: 87) | — |
| C8-6 | SVSSSVSSIYLH (SEQ ID NO: 53) | STSNLAS (SEQ ID NO: 54) | IQYSGYPLT (SEQ ID NO: 55) |
| C8-H241 | SVSSSVSSIYLH (SEQ ID NO: 53) | STSNLAS (SEQ ID NO: 54) | QVYSGYPLT (SEQ ID NO: 56) |
| C8-co-16 | SVSSSVRSIYLH (SEQ ID NO: 57) | STSNLAS (SEQ ID NO: 54) | QVYRGYPLT (SEQ ID NO: 58) |
| C8 Consensus Sequence | SVSSSVX$_3$SIYLH (SEQ ID NO: 88) | — | X$_4$X$_5$YX$_6$GYPLT (SEQ ID NO: 89) |

$X_1$ is Y or R, and $X_2$ is A or R;
$X_3$ is S or R;
$X_4$ is I or Q, $X_5$ is Q or V, and $X_6$ is S or R;

TABLE 2

Heavy Chain CDRs

| Antibody | CDR 1 | CDR 2 | CDR 3 |
|---|---|---|---|
| D11-S17Y | GYTFTSRYIH (SEQ ID NO: 59) | WIYPVTGDTYYNEKFKG (SEQ ID NO: 60) | GYGAFYY (SEQ ID NO: 61) |
| D11-8B8 | GYTFTSRYIH (SEQ ID NO: 59) | WIYPVTGDTYYIEKFKG (SEQ ID NO: 62) | GYGAFFY (SEQ ID NO: 63) |
| D11-C27G3 | GYTFTSRYIH (SEQ ID NO: 59) | WIYPVTGDTYYREPFKG (SEQ ID NO: 64) | GYGAFYY (SEQ ID NO: 61) |
| D11 Consensus Sequence | — | WIYPVTGDTYYX$_7$EX$_8$FKG (SEQ ID NO: 90) | GYGAFX$_9$Y (SEQ ID NO: 91) |
| C8-6 | GYTFTDYYMH (SEQ ID NO: 65) | RVNPNRGGTTYNQKFEG (SEQ ID NO: 66) | TNWLDY (SEQ ID NO: 67) |
| C8-H241 | GYTFTDYYMH (SEQ ID NO: 65) | RVNPNRRGTTYNQKFEG (SEQ ID NO: 68) | ANWLDY (SEQ ID NO: 69) |
| C8-co-16 | GYTFTDYYMH (SEQ ID NO: 65) | RVNPYRGSTTYNQKFEG (SEQ ID NO: 70) | ANILDY (SEQ ID NO: 71) |
| C8 Consensus Sequence | — | RVNPX$_{10}$RX$_{11}$X$_{12}$TTYNQKFEG (SEQ ID NO: 92) | X$_{13}$NX$_{14}$LDY (SEQ ID NO: 93) |

$X_7$ is N, I, or R, and $X_8$ is K or P;
$X_9$ is Y or F;
$X_{10}$ is N or Y, $X_{11}$ is G or R, and $X_{12}$ is G or S;
$X_{13}$ is T or A, and $X_{14}$ is W or I;

Consensus sequences for D11- and C8-antibody light and heavy chain variable regions are:

D11- Antibody Light Chain Variable Region Consensus Sequence
(SEQ ID NO: 94)
EIVLTQSPGTLSLSPGERATLSCSVSSSISSTNLHWYQQKPGQAPRLLIY

GTSX$_1$LX$_2$SGIPDRFSGSGSGTDFTLTISRLEPEDFAVYYCQQWSSYPYS

FGQGTKLEIK wherein $X_1$ is Y or R, and $X_2$ is A or R;

C8- Antibody Light Chain Variable Region Consensus Sequence
(SEQ ID NO: 95)
DIQMTQSPSSLSASVGDRVTITCSVSSSVX$_3$SIYLHWYQQKPGKAPKLLI

YSTSNLASGVPSRFSGSGSGTDFTLTISSLQPEDFATYYCX$_4$X$_5$YX$_6$GYP

LTFGGGTKVEIK wherein $X_3$ is S or R, $X_4$ is I or Q, $X_5$ is Q, or V, and $X_6$ is S or R;

D11- Antibody Heavy Chain Variable Region Consensus Sequence
(SEQ ID NO: 96)
QVQLVQSGAEVKKPGSSVKVSCKASGYTFTSRYIHWVRQAPGQGLEWMGW

IYPVTGDTYYX$_7$EX$_8$FKGRVTITADKSTSTAYMELSSLRSEDTAVYYCAR

GYGAFX$_9$YWGQGTLVTVS wherein $X_7$ is N, I, or R, $X_8$ is K or P, and $X_9$ is Y or F;

C8- Antibody Heavy Chain Variable Region Consensus Sequence
(SEQ ID NO: 97)
QVQLVQSGAEVKKPGASVKVSCKASGYTFTDYYMHWVRQAPGQGLEWMGR

VNPX$_{10}$RX$_{11}$X$_{12}$TTYNQKFEGRVTMTTDTSTSTAYMELRSLRSDDTAVY

YCARX$_{13}$NX$_{14}$LDYWGQGTTVTVS wherein $X_{10}$ is Y or N, $X_{11}$ is G or R, $X_{12}$ is S or G, $X_{13}$ is A or T, and $X_{14}$ is I or W.

Antibodies are transiently expressed in HEK293 EBNA cells (Edge BioSystems, #90500130) using standard transfection procedures. Transfected cells are cultured in standard serum-free medium containing geneticin (G418) and tobramycin for 48 to 120 hours at 37° C. after transfection. Antibodies are purified on a 60 mL rProtein A Sepharose column (Amersham Biosciences, #17-1279-04) by following the manufacturer's instructions, and further concentrated and purified by size exclusion chromatography (XK50/60 Superdex200, Pharmacia) with phosphate buffered saline (PBS), pH 7.4, as the mobile phase. Antibodies are then filtered using Millev-GV, PVDF membranes, 0.22 μm, 33 mm, (Millipore, # SLGV033RS), and stored at 4 to 8° C.

Murine IgG1 c-Met antibody 5D5 (U.S. Pat. No. 5,686, 292), discussed in many of the examples below, is isolated and purified from hybridoma HB-11895 obtained from the American Type Culture Collection, Manassas, Va., as described above.

EXAMPLE 2

Binding Kinetics of c-Met Antibodies to Various c-Met Extracellular Domains

The extracellular domains (ECDs) of human, cynomolgus monkey, and rat c-Met sequences are expressed as Fc fusion proteins with a flag- and His-tag (Flis-tag) at the C-terminus of the Fc (SEQ ID NOs:72-74). These c-Met ECD Fc fusion proteins are separately transiently expressed in HEK293 EBNA cells and purified as described in Example 1.

A Biacore® 2000 instrument is used to measure the binding kinetics of c-Met antibodies to human, cynomolgus monkey, and rat c-Met ECDs. Measurements are performed at 25° C. Samples are dissolved in HBS-EP buffer (150 mM sodium chloride, 3 mM EDTA, 0.005% (w/v) surfactant P-20, and 10 mM N-2-hydroxyethylpiperazine-N'-2-ethanesulfonic acid (HEPES) at pH 7.4; #BR-1001-88). F(ab')$_2$ fragment of goat anti human IgG, F(ab')$_2$ fragment specific (Jackson Immunoresearch Inc, #109-006-097) is immobilized on flow cells 1 to 4 of a CM5 sensor chip at a level of 4000 response units (RUs) using amine coupling chemistry to capture anti-c-Met antibodies.

Binding is evaluated using multiple cycles. Each cycle is performed at a flow rate of 50 μL/min., and consists of the following steps: injection of about 10 μL of a c-Met antibody at 10 μg/mL aiming at a capture of 40-100 RUs, injection of 250 μL of human, cynomolgus, or rat c-Met-Flis-Fc ECD (starting at 100 nM and using two-fold serial dilutions for each cycle) followed by 20 min. for dissociation, and regeneration using about 30 μL of 10 mM glycine hydrochloride, pH 1.5. Association and dissociation rates for each cycle are evaluated using a "1:1 (Langmuir) binding" model in the BIAevaluation software, version 4.1. For binding of antibody D11-S17Y to rat c-Met-Flis-Fc ECD, a heterogeneous ligand model is used to fit the data adequately; therefore, two binding affinities are obtained.

The results are shown in Tables 3-5 below.

TABLE 3

Binding Kinetics and Affinity of c-Met Antibodies to Human c-Met-Flis-Fc ECD

| Antibody | $k_{on}$ (1/Ms) | $k_{off}$ (1/s) | $K_D$ (nM) |
|---|---|---|---|
| D11-8B8 | $1.0 \pm 0.1 \times 10^5$ | $0.5 \pm 0.2 \times 10^{-4}$ | $0.5 \pm 0.2$ |
| D11-C27G3 | $6.4 \pm 0.2 \times 10^4$ | $0.9 \pm 0.2 \times 10^{-4}$ | $1.4 \pm 0.3$ |
| D11-S17Y | $0.7 \pm 0.1 \times 10^5$ | $2.8 \pm 0.1 \times 10^{-4}$ | $4.2 \pm 0.9$ |
| C8-H241 | $1.1 \pm 0.3 \times 10^5$ | $<10^{-5}$ | $<0.1$ |
| C8-6 | $1.6 \pm 0.4 \times 10^5$ | $3 \pm 2 \times 10^{-4}$ | $4 \pm 1$ |
| C8-co16 | $1.1 \pm 0.2 \times 10^5$ | $0.3 \pm 0.2 \times 10^{-4}$ | $0.3 \pm 0.1$ |

TABLE 4

Binding Kinetics and Affinity of c-Met Antibodies to Cynomolgus Monkey c-Met-Flis-Fc ECD

| Antibody | $k_{on}$ (1/Ms) | $k_{off}$ (1/s) | $K_D$ (nM) |
|---|---|---|---|
| D11-8B8 | $0.78 \pm 0.02 \times 10^5$ | $2.23 \pm 0.07 \times 10^{-4}$ | $2.9 \pm 0.2$ |
| D11-C27G3 | $0.5 \pm 0.1 \times 10^5$ | $3.2 \pm 0.4 \times 10^{-4}$ | $6.5 \pm 0.7$ |
| D11-S17Y | $0.70 \pm 0.08 \times 10^5$ | $3.6 \pm 0.5 \times 10^{-4}$ | $5.1 \pm 0.2$ |
| C8-H241 | $0.80 \pm 0.06 \times 10^5$ | $<10^{-5}$ | $<0.2$ |
| C8-6 | $1.4 \pm 0.5 \times 10^5$ | $4.5 \pm 0.2 \times 10^{-4}$ | $3.6 \pm 1.1$ |
| C8-co16 | $1.03 \pm 0.02 \times 10^5$ | $<10^{-5}$ | $<0.1$ |

TABLE 5

Binding Kinetics and Affinity of c-Met Antibodies to Rat c-Met-Flis-Fc ECD

| Antibody | $k_{on}$ (1/Ms) | $k_{off}$ (1/s) | $K_D$ (pM) | $k_{on}$ (1/Ms) | $k_{off}$ (1/s) | $K_D$ (nM) |
|---|---|---|---|---|---|---|
| D11-8B8 | $2.1 \pm 0.2 \times 10^5$ | $1.9 \pm 0.3 \times 10^{-4}$ | $0.89 \pm 0.04$ | | | |
| D11-C27G3 | $1.3 \pm 0.1 \times 10^5$ | $3.4 \pm 0.5 \times 10^{-4}$ | $2.7 \pm 0.2$ | | | |
| D11-S17Y | $0.66 \times 10^5$ | $189 \times 10^{-4}$ | $286$ | $2.5 \times 10^5$ | $3.0 \times 10^{-4}$ | $1.2$ |

These data demonstrate that antibodies C8-H241, C8-6, and C8-co16 bind both human and cynomolgus monkey c-Met ECDs with similar affinity, but not rat c-Met ECD. Additional data (not shown) indicate that these antibodies do not bind mouse c-Met ECD at up to 100 nM of antibody with 1 μg/mL ECD coated on ELISA plates. Antibodies D11-8B8, D11-C27G3, and D11-S17Y, however, bind human, cynomolgus monkey, and rat c-Met ECDs.

EXAMPLE 3

Epitope Mapping

The epitopes of the present c-Met antibodies are mapped by a combination of hydrogen-deuterium exchange mass spectrometry (HDXMS) (Yamada et al. (2002) *Rapid Commun. Mass Spectrom.* 16(4):293-299) and diethyl pyrocarbonate (DEPC) labeling (Mendoza et al. (2008) *Analy. Chem.* 80(8):2895-2904). Hydrogen-deuterium exchange reaction of human c-Met Sema domain is carried out in the presence or absence of c-Met antibodies. Sema domain regions that gain less deuterium in the presence of an antibody than in its absence are identified as the epitope(s) for the antibody. DEPC can react with amino groups of surface-exposed lysine or histidine residues in the Sema domain, forming ethyl carbamate lysine or histidine. If these amino acids are located in the epitope region, they will be protected, and will not react with DEPC upon antibody binding. This helps to further localize and/or confirm the epitope regions determined by HDXMS.

Expression and Purification of c-Met Sema Domain. The Sema domain of human c-Met is expressed with a Flis tag at the C-terminus (SEQ ID NO:76) in HEK293 EBNA cells and purified as described in Examples 1 and 2. The purified protein is then stored at 4° C. in PBS at pH 7.4. This domain binds to the c-Met antibodies of the present invention with affinity similar to that of full length human c-Met ECD, indicating that the epitopes for these antibodies are located in this region of human c-Met.

Deglycosylation and Desialylation of the c-Met Sema Domain. 100 µL of 1.2 mg/mL human c-Met Sema domain solution are treated with 1 µL of PNGase F solution (Prozyme, GKE-5006B) at 37° C. overnight for de-N-glycosylation. LC/MS analysis demonstrates that most of the protein is deglycosylated after this treatment. Separately, 100 µL of 1.2 mg/mL human c-Met Sema domain solution are treated with 2 µL of 10 U/mL neuraminidase solution (Roche, Cat. #10 269 611 001) at 37° C. for 1 hour to desialylate the Sema domain.

Formation of c-Met Sema Domain/Antibody Complexes. 10 µL of deglycosylated c-Met Sema domain solution (1.2 mg/mL) are mixed with an aliquot containing 29 µg protein of antibody solution (2.07 µL of C8-H241, 2.01 µL of D11-8B8, or 3.87 µL of an unrelated control Mab), and then diluted with 1×PBS solution to a final volume of 40 µL. Separately, 5 µL of desialylated human c-Met Sema domain solution (1.2 mg/mL) are mixed with an aliquot containing 14 µg protein of antibody solution (1.04 µL of C8-H241, 1.01 µL of D11-8B8, or 1.94 µL of the unrelated control Mab), and then diluted with 1×PBS solution to a final volume of 15 µL. Each of the mixed solutions of each antibody is then subjected to HDXMS analysis.

HDXMS Assays. 4 µL of deglycosylated or desialylated c-Met Sema domain/antibody mixture are mixed with 16 µL of 100% D$_2$O (Acros, Code 166310500; 80% D during exchange), and incubated at ambient temperature for 90 seconds. The exchange is then quenched with 50 µL of 0.5% (v/v) formic acid in water at 0° C. The quenched solution is immediately treated with 2 µL of 5 mg/mL (v/v) pepsin solution (Sigma, Cat. # P6887) at 0° C. for 3.5 or 4 min. The digested solution is immediately manually injected onto an RP-HPLC column (Polymer Laboratories, Part #1912-1802; 2.1×50 mm, 1000 Å pore size, 8 µM particle size). The HPLC buffer stream from the HPLC pump (Waters, 2795 HPLC) passes through a metal tube (approximately 1 mL) to a manual injector. The column eluate is then passed to a Micromass LCT Premier or SYNAPT mass spectrometer. The metal tube, injector loop, and column are submerged in an ice water bath.

The column is equilibrated with 99% A (0.05% (v/v) aqueous TFA (trifluoroacetic acid) and 1% B (0.04% (v/v) TFA in acetonitrile) at a flow rate of 0.2 mL/min. An isocratic gradient elution is performed for 1 min., from 1 to 10% B over 1 min., to 40% B over 12 min., to 90% B over 4 min. with a 3 min. hold, and then rapidly returned to the initial conditions. The mass spectrometry is performed on a Micromass LCT Premier Mass Spectrometer with a positive spray, W mode, and the following settings: a capillary voltage of 1.5 kV, a cone voltage of 100 V, Aperture 1 of 25 V, a mass range of 200 to 2000, a desolvation temperature of 150° C., and a desolvation gas flow of 500 L/h. The mass spectrum of each peptic peptide of c-Met is obtained after D/H exchange with or without c-Met antibody. The average mass of each peptide is calculated according to the isotopic distribution of the most intense ion peak.

DEPC Labeling of c-Met/Antibody Complexes. 8.3 µL of 1.2 mg/mL human c-Met Sema domain solution are mixed with an antibody solution (24 µg protein: 1.71 µL of C8-H241, 1.67 µL of D11-8B8, or 3.2 µL of unrelated control Mab), and 1×PBS solution to a final volume of 76 µL. Each c-Met/antibody mixture is treated with 4 µL of 10 mg/mL (w/v) DEPC in isopropanol at ambient temperature for 5 min. and then quenched with 10 µL of 20 mg/mL histidine in 0.1 M Tris-HCl buffer, pH 8, and 10 µL of 0.2 mg/mL lysine in 0.1 M Tris-HCl buffer, pH 8. Each solution is mixed with 5 µL of 0.2 mg/mL (w/v) porcine trypsin solution (Promega, Cat. # V528A), and half of the mixture is mixed with 0.5 µL of 50 mg/mL (w/v) dithiothreitol solution. Each sample solution is incubated at 37° C. for 5 hours and then treated with 0.5 µL of PNGase F solution for an additional hour. Each digested solution is acidified with 2 µL of 10% (v/v) acetic acid solution. 2 µL of 100 mg/mL TCEP (tris(2-carboxyethyl) phosphine hydrochloride (Sigma, Cat. # C4702-2G) solution are added to the unreduced digest without added dithiothreitol. Each of the solutions is subjected to LC/MS analysis using a Waters Acquity HPLC and Waters SYNAPT Mass spectrometer. The HPLC uses a Waters Acquity HPLC BEH C8 column (2.1×50 mm, 1.7 µm, Waters, part #186002877) at 60° C., and peptides are eluted with an acetonitrile gradient in a water/acetonitrile/TFA HPLC mobile phase system. A 45 min. run time is used for the digests. The column is equilibrated with 99% A (0.05% (v/v) TFA aqueous solution) and 1% B (0.04% (v/v) TFA in acetonitrile) at a flow rate of 0.2 mL/min. A gradient elution is performed in isocratic state for 2 min., from 1 to 25% B over 25 min., to 45% B over 10 min., to 90% B over 1 min., with 1.5 min. hold (at the same period of time, flow rate of 0.3 mL/min.), and then rapidly returned to 1% B.

Results. Mab C8-H241 appears to bind a conformational epitope comprising four regions of the c-Met Sema domain, located in the α-chain of the human c-Met extracellular domain (amino acid residues 25-307 of SEQ ID NO:75):

| | |
|---|---|
| $_{121}$VVDTYYDDQL$_{130}$, | (SEQ ID NO: 77) |
| $_{131}$ISCGSVNRGTCQRHVFPHNHTADIQS$_{156}$, | (SEQ ID NO: 78) |
| $_{179}$ALGAKVLSSVKDRFINFF$_{196}$, and | (SEQ ID NO: 79) |
| $_{216}$VRRLKETKDGFM$_{227}$. | (SEQ ID NO: 80) |

More particularly, Mab C8-H241 binds c-Met by interacting with one or more amino acid residues within:

| | |
|---|---|
| $_{123}$DTYYDD$_{128}$ | (SEQ ID NO: 81) inclusive, |
| $_{144}$HVFPHNHTADIQS$_{156}$ | (SEQ ID NO: 82) inclusive, |
| $_{192}$FINF$_{195}$ | (SEQ ID NO: 83) inclusive, and |
| $_{220}$KETKDGFM$_{227}$ | (SEQ ID NO:84) inclusive. |

Binding of Mab C8-H241 to the region $_{144}$HVFPHNHTADIQS$_{156}$ (SEQ ID NO: 82) renders it capable of binding both human (SEQ ID NO:75) and cynomolgus monkey (amino acids 25 to 932 of SEQ ID NO:73) c-Met extracellular domain with comparable affinity, but not rat or mouse c-Met, up to 100 nM of antibody in binding assays.

Mab D11-8B8 binding to the α-chain of the c-Met Sema domain appears to be localized to one region, i.e., amino acid residues within a linear epitope within the amino acid sequence $_{84}$YKTGPVLEHPDCFPCQDCSSKANL$_{107}$ (SEQ ID NO:85) inclusive, more particularly the region $_{95}$CFPCQDCSSKA$_{105}$ (SEQ ID NO:86) inclusive. The epitope for Mab D11-8B8 is further confirmed by epitope extraction experiments (Dhungana et al. (2009) *Methods Mol. Biol.* 524:87-101). c-Met Sema domain is digested with porcine trypsin (Promega) and the digest is then mixed with biotinylated Mab D11-8B8, using the EZ-Link™ Sulfo-NHS-LC- Biotin kit (Pierce, Prod. #1754210), to bind the c-Met peptides. Biotinylated D11-8B8 with or without bound c-Met peptides is captured by high capacity Streptavidin agarose resin (Thermo Scientific, Prod. #20359). The bound peptides are released by 0.15% formic acid (v/v) in $H_2O$, and then identified by LC/MS.

EXAMPLE 4

Preferential Binding of Antibodies to c-Met Vs. Ron and Plexina2 ECDs

The human proteins with the greatest sequence identity to c-Met are RON and PlexinA2. This experiment compares the specificity of c-Met antibody binding to c-Met, RON, and PlexinA2 ECDs.

Wells of 96-well EIA/RIA high binding plates (Costar, #2592) are coated with 100 μL of 1 μg/mL human c-Met extracellular domain (ECD)-Fc-Flis fusion (SEQ ID NO:72), RON-ECD-Fc (R&D Systems, #1947-MS), or PlexinA2-ECD-Fc (Abnova, Taipei, Taiwan #H00005362-P01) in coating buffer (BioFX Labs, # COAT-1000-01) overnight at 4° C. The wells are aspirated and non-specific binding sites are blocked by adding 200 μL of blocking buffer (Tris-buffered saline, pH 8.0, with 0.05% (v/v) polysorbate 20 (Tween-20) (TBS-T) (BioFX Labs, # WSHW-1000-01) plus 1% (w/v) bovine serum albumin (BSA) (Jackson Immuno, #001-000-162) and incubating for 1 hour at room temperature. After the plates are washed three times with wash buffer (TBS-T), 100 μL/well of 1:6 serial dilutions of c-Met antibodies in blocking buffer (starting from 100 μg/mL) are added and incubated at room temperature for 2 hours. The plates are washed and incubated with 100 μL/well of HRP-conjugated goat anti-human F(ab)$_2$ IgG (Jackson ImmunoResearch Labs #109-036-097) in blocking buffer for 90 min. After the plates are washed, 100 μL/well of substrate solution (BioFx, #TMBW-1000-01) are added and the plates are incubated for 10 min. at room temperature. 100 μL/well of stop solution (BioFx, # LSTP-1000-01) are added to stop the reaction. The colorimetric signals are developed and read at 450 nm using a SpectraMax 190 plate reader (Molecular Devices, Sunnyvale, Calif.). c-Met antibody binding to c-Met, RON and PlexinA2 ECDs is proportional to color signal production.

As shown in Table 6, both C8 and D11 c-Met antibodies of the present invention preferentially bind to human c-Met ECD compared to RON ECD or PlexinA2 ECDs.

TABLE 6

Preferential Binding of c-Met Antibodies to Human c-Met ECD vs. RON and PlexinA2 ECDs

| | Average A450 nm | | | | | | | | |
|---|---|---|---|---|---|---|---|---|---|
| Antibody | C8-H241 | | | C8-6 | | | C8-co16 | | |
| dose (ng/mL) | c-Met ECD | RON ECD | Plexin A2 | c-Met ECD | RON ECD | Plexin A2 | c-Met ECD | RON ECD | Plexin A2 |
| 0.000 | 0.300 | 0.098 | 0.092 | 0.322 | 0.110 | 0.109 | 0.335 | 0.106 | 0.104 |
| 0.002 | 0.317 | 0.088 | 0.082 | 0.326 | 0.106 | 0.099 | 0.369 | 0.100 | 0.094 |
| 0.010 | 0.317 | 0.081 | 0.090 | 0.335 | 0.097 | 0.095 | 0.374 | 0.096 | 0.078 |
| 0.060 | 0.484 | 0.104 | 0.099 | 0.551 | 0.087 | 0.096 | 0.446 | 0.089 | 0.082 |
| 0.357 | 0.902 | 0.091 | 0.097 | 0.813 | 0.080 | 0.107 | 0.907 | 0.083 | 0.095 |
| 2.143 | 2.861 | 0.101 | 0.103 | 2.415 | 0.098 | 0.106 | 2.888 | 0.114 | 0.092 |
| 12.860 | 4.000 | 0.079 | 0.083 | 4.000 | 0.087 | 0.085 | 4.000 | 0.102 | 0.069 |
| 77.160 | 4.000 | 0.085 | 0.079 | 4.000 | 0.090 | 0.078 | 4.000 | 0.084 | 0.096 |
| 462.963 | 4.000 | 0.090 | 0.104 | 4.000 | 0.088 | 0.086 | 4.000 | 0.103 | 0.092 |
| 2777.778 | 4.000 | 0.085 | 0.092 | 4.000 | 0.088 | 0.094 | 4.000 | 0.095 | 0.114 |
| 16666.667 | 4.000 | 0.117 | 0.125 | 4.000 | 0.124 | 0.118 | 4.000 | 0.198 | 0.284 |
| 100000.000 | 4.000 | 0.267 | 0.310 | 4.000 | 0.170 | 0.171 | 4.000 | 0.421 | 0.983 |
| | Standard Error | | | | | | | | |
| 0.000 | 0.006 | 0.015 | 0.007 | 0.011 | 0.000 | 0.004 | 0.003 | 0.005 | 0.011 |
| 0.002 | 0.003 | 0.006 | 0.002 | 0.012 | 0.005 | 0.006 | 0.023 | 0.000 | 0.006 |
| 0.010 | 0.002 | 0.000 | 0.005 | 0.001 | 0.004 | 0.009 | 0.015 | 0.012 | 0.002 |
| 0.060 | 0.055 | 0.001 | 0.002 | 0.144 | 0.004 | 0.005 | 0.029 | 0.003 | 0.002 |
| 0.357 | 0.004 | 0.004 | 0.002 | 0.022 | 0.005 | 0.003 | 0.005 | 0.007 | 0.000 |
| 2.143 | 0.032 | 0.004 | 0.005 | 0.041 | 0.004 | 0.003 | 0.128 | 0.002 | 0.007 |
| 12.860 | 0.000 | 0.001 | 0.012 | 0.000 | 0.000 | 0.007 | 0.000 | 0.004 | 0.004 |
| 77.160 | 0.000 | 0.002 | 0.014 | 0.000 | 0.008 | 0.007 | 0.000 | 0.003 | 0.001 |
| 462.963 | 0.000 | 0.004 | 0.003 | 0.000 | 0.006 | 0.001 | 0.000 | 0.013 | 0.001 |
| 2777.778 | 0.000 | 0.004 | 0.002 | 0.000 | 0.004 | 0.001 | 0.000 | 0.007 | 0.000 |
| 16666.667 | 0.000 | 0.005 | 0.004 | 0.000 | 0.004 | 0.003 | 0.000 | 0.003 | 0.002 |
| 100000.000 | 0.000 | 0.008 | 0.012 | 0.000 | 0.002 | 0.003 | 0.000 | 0.011 | 0.093 |

| Antibody | D11-8B8 | | | D11-C27G3 | | | D11-S17Y | | |
|---|---|---|---|---|---|---|---|---|---|
| dose (ng/mL) | c-Met ECD | RON ECD | Plexin A2 | c-Met ECD | RON ECD | Plexin A2 | c-Met ECD | RON ECD | Plexin A2 |
| 0.000 | 0.297 | 0.097 | 0.081 | 0.2844 | 0.0791 | 0.0771 | 0.31475 | 0.1129 | 0.10795 |
| 0.002 | 0.299 | 0.082 | 0.078 | 0.2708 | 0.07065 | 0.07965 | 0.3091 | 0.09705 | 0.09345 |
| 0.010 | 0.304 | 0.074 | 0.078 | 0.2904 | 0.0715 | 0.0763 | 0.31405 | 0.0868 | 0.0986 |
| 0.060 | 0.445 | 0.094 | 0.073 | 0.45965 | 0.0695 | 0.06605 | 0.37355 | 0.0857 | 0.09455 |
| 0.357 | 1.314 | 0.073 | 0.074 | 1.43965 | 0.07085 | 0.0792 | 0.78915 | 0.08475 | 0.0924 |
| 2.143 | 2.416 | 0.069 | 0.073 | 2.5266 | 0.0655 | 0.0742 | 2.1432 | 0.1085 | 0.08235 |
| 12.860 | 3.931 | 0.079 | 0.075 | 4 | 0.07835 | 0.0641 | 4 | 0.0825 | 0.0768 |
| 77.160 | 4.000 | 0.079 | 0.066 | 4 | 0.06725 | 0.076 | 4 | 0.08195 | 0.07575 |

TABLE 6-continued

Preferential Binding of c-Met Antibodies to Human c-Met ECD vs. RON and PlexinA2 ECDs

| | | | | | | | | | | |
|---|---|---|---|---|---|---|---|---|---|---|
| 462.963 | 4.000 | 0.071 | 0.077 | 4 | 0.0981 | 0.1045 | 4 | | 0.08185 | 0.0783 |
| 2777.778 | 4.000 | 0.088 | 0.093 | 4 | 0.20445 | 0.30325 | 4 | | 0.09255 | 0.0955 |
| 16666.667 | 4.000 | 0.165 | 0.181 | 4 | 0.67565 | 1.33475 | 4 | | 0.1274 | 0.1491 |
| 100000.000 | 4.000 | 0.544 | 0.498 | 3.9211 | 2.30295 | 3.37085 | 4 | | 0.23775 | 0.3146 |
| Standard Error | | | | | | | | | | |
| 0.000 | 0.006 | 0.003 | 0.003 | 0.0087 | 0.0017 | 0.0106 | 0.00515 | 0.0012 | 0.00035 |
| 0.002 | 0.011 | 0.002 | 0.002 | 0.0194 | 0.00595 | 0.00185 | 0.0228 | 0.00065 | 0.01725 |
| 0.010 | 0.012 | 0.002 | 0.001 | 0.0051 | 0.0018 | 0.0017 | 0.01195 | 0.0058 | 0.0079 |
| 0.060 | 0.007 | 0.017 | 0.003 | 0.01495 | 0.0006 | 0.00335 | 0.00375 | 0.0013 | 0.00035 |
| 0.357 | 0.092 | 0.007 | 0.004 | 0.02935 | 0.00695 | 0.0017 | 0.04195 | 0.00075 | 0.0039 |
| 2.143 | 0.044 | 0.002 | 0.001 | 0.2742 | 0.0002 | 0.0015 | 0.0841 | 0.0054 | 0.00015 |
| 12.860 | 0.069 | 0.005 | 0.002 | 0 | 0.01505 | 0.0043 | 0 | 0.0029 | 0.0061 |
| 77.160 | 0.000 | 0.007 | 0.000 | 0 | 0.00275 | 0.0066 | 0 | 0.00445 | 0.00455 |
| 462.963 | 0.000 | 0.005 | 0.004 | 0 | 0.0063 | 0.0032 | 0 | 0.00485 | 0.0089 |
| 2777.778 | 0.000 | 0.003 | 0.005 | 0 | 0.00975 | 0.00535 | 0 | 0.00705 | 0.0055 |
| 16666.667 | 0.000 | 0.007 | 0.004 | 0 | 0.03125 | 0.03495 | 0 | 0.0007 | 0.0035 |
| 100000.000 | 0.000 | 0.016 | 0.006 | 0.0789 | 0.07335 | 0.14345 | 0 | 0.00865 | 0.004 |

EXAMPLE 5 c-Met Antibodies Block HGF/c-Met Binding

In vitro binding assays are used to determine inhibition of HGF binding to c-Met by the present c-Met antibodies.

Wells of 96-well EIA/RIA high binding plates (Costar, #2592) are coated with 100 μL of human c-Met ECD-Fc-Flis (SEQ ID NO:72) (2 μg/mL) in Dulbecco's phosphate buffered saline (DPBS) overnight at room temperature; washed four times with wash buffer (Tris-buffered saline, pH 8.0, with 0.05% (v/v) polysorbate 20 (TWEEN®-20) (TBS-T) (BioFX Labs, # WSHW-1000-01) in a plate washer; blocked by adding 300 μL of blocking buffer (TBS-T plus 1% (w/v) bovine serum albumin (BSA) (Jackson Immuno, #001-000-162); and incubating for 60 min. at 37° C. Blocking buffer is then removed from the wells and 50 μL of antibodies in blocking buffer at final concentrations as indicated in Table 7 are added into each well, respectively. Blocking buffer is added to the HGF-only control wells. The plates with c-Met antibodies are incubated for 90 min. at 37° C. 50 μL of human hepatocyte growth factor (HGF) (R&D Systems, #294) in blocking buffer at a final concentration of 10 ng/mL are then added to each well except the antibody-only control wells. The plates containing the c-Met antibody/HGF mixture are incubated on a plate shaker for two hours at room temperature. The wells are then washed four times with TBS-T in a plate washer. Next, 100 μL of biotinylated anti-HGF antibody (R&D Systems, # BAF294) in blocking buffer at a final concentration of 100 ng/mL are added into each well. The plates are incubated for 90 min. at room temperature. The wells are again washed four times with TBS-T in a plate washer. 100 μL of a 1:200 dilution of streptavidin-horseradish peroxidase (HRP) (R&D Systems, DY998) in blocking buffer are added to each well. The plates are incubated for 30 min. at room temperature. The wells are washed four times with TBS-T in a plate washer. 100 μL/well of substrate solution (BioFx, #TMBW-1000-01) are then added, and the plates are incubated for 10 min. at room temperature. To stop the reaction, 100 μL/well of stop solution (BioFx, # LSTP-1000-01) are added. The samples are read at a wavelength of 450-570 nm on a microplate reader (Spectra, MAX 190) and no background is subtracted.

As shown in Table 7, both C8 and D11 c-Met antibodies of the present invention block human HGF/c-Met binding.

TABLE 7

Inhibition of Human HGF Binding to Human c-Met by C8- and D11- Antibodies

| Antibody dose (ng/mL) | hIgG2 | D11-8B8 | D11-27G3 | D11-S17Y | hIgG4 | C8-6 | C8-H241 | C8-co16 |
|---|---|---|---|---|---|---|---|---|
| AVG A450 nm | | | | | | | | |
| 0.00 | 2.43 | 2.43 | 2.43 | 2.43 | 2.61 | 2.61 | 2.61 | 2.61 |
| 0.48 | 2.46 | 2.51 | 2.37 | 2.15 | 2.41 | 2.56 | 2.45 | 2.05 |
| 1.91 | 2.87 | 2.48 | 2.31 | 1.98 | 2.49 | 2.59 | 2.46 | 2.18 |
| 7.63 | 2.70 | 2.41 | 2.27 | 2.08 | 2.88 | 2.64 | 2.53 | 2.20 |
| 30.52 | 2.41 | 2.32 | 2.38 | 2.07 | 2.63 | 2.42 | 2.42 | 2.08 |
| 122.07 | 2.52 | 1.92 | 1.60 | 1.69 | 2.44 | 2.00 | 1.77 | 1.30 |
| 488.28 | 2.53 | 1.30 | 0.94 | 1.29 | 2.44 | 1.33 | 0.73 | 0.70 |
| 1953.13 | 2.43 | 1.43 | 0.97 | 1.23 | 2.27 | 1.08 | 0.68 | 0.60 |
| 7812.50 | 2.50 | 1.24 | 0.91 | 1.12 | 2.49 | 0.95 | 0.70 | 0.57 |
| 31250.00 | 2.50 | 1.31 | 0.94 | 1.17 | 2.67 | 0.98 | 0.77 | 0.56 |
| 125000.00 | 2.43 | 1.38 | 0.89 | 1.35 | 3.00 | 1.32 | 0.69 | 0.38 |
| STDErr | | | | | | | | |
| 0.00 | 0.06 | 0.06 | 0.06 | 0.06 | 0.10 | 0.10 | 0.10 | 0.10 |
| 0.48 | 0.02 | 0.13 | 0.01 | 0.09 | 0.24 | 0.02 | 0.14 | 0.15 |
| 1.91 | 0.27 | 0.08 | 0.08 | 0.03 | 0.00 | 0.03 | 0.16 | 0.12 |
| 7.63 | 0.14 | 0.01 | 0.21 | 0.08 | 0.14 | 0.03 | 0.06 | 0.09 |
| 30.52 | 0.09 | 0.02 | 0.31 | 0.09 | 0.16 | 0.01 | 0.03 | 0.01 |
| 122.07 | 0.09 | 0.07 | 0.03 | 0.02 | 0.08 | 0.10 | 0.02 | 0.03 |
| 488.28 | 0.00 | 0.04 | 0.04 | 0.02 | 0.01 | 0.02 | 0.00 | 0.01 |
| 1953.13 | 0.13 | 0.16 | 0.02 | 0.05 | 0.00 | 0.01 | 0.01 | 0.01 |
| 7812.50 | 0.04 | 0.01 | 0.01 | 0.02 | 0.25 | 0.07 | 0.01 | 0.02 |
| 31250.00 | 0.06 | 0.02 | 0.02 | 0.04 | 0.03 | 0.03 | 0.03 | 0.03 |
| 125000.00 | 0.07 | 0.03 | 0.01 | 0.08 | 0.13 | 0.47 | 0.01 | 0.00 |

Abbreviations:
AVG = average;
STDErr = Standard Error

EXAMPLE 6 c-Met Antibodies Induce Weak c-Met Phosphorylation Compared to Hepatocyte Growth Factor and Agonist Mab 5D5

Upon stimulation with HGF, the A549 lung carcinoma cell line exhibits increased c-Met phosphorylation at tyrosine residue 1349. A phosphorylated c-Met (p-Met) ELISA assay is used to measure the agonistic activity of various c-Met antibodies in the absence of HGF, as well as of Mab 5D5 and HGF itself.

A549 cells (ATCC, #CCL-185) are cultured in Ham's F12K+2 mM glutamine (Invitrogen, #21127-022)+10% FBS medium (Invitrogen, #10082). Cells are plated at $6\times10^4$ cells/well in the full serum medium as above in 96-well plates and incubated overnight at 37° C. under 5% (v/v) $CO_2$. The medium is removed from the wells and the cells are starved in 100 µL of Ham's F12K+2 mM glutamine medium+0.5% FBS for six hours at 37° C. under 5% (v/v) $CO_2$. Antibodies or HGF are diluted in the starvation culture medium, added at final concentrations as indicated in Table 8, and incubated for 15 min. at 37° C. The medium is aspirated and cells are lysed in 50 µL lysis buffer (10 mM Tris (Invitrogen, #15567-027), 150 mM NaCl, 2 mM ethylenediaminetetraacetic acid (EDTA) (Invitrogen, #15575-038), 50 mM NaF (Sigma, #S1504), 1% (v/v) octylphenoxy polyethoxy ethanol (TRITON®-X 100; Sigma, #T8787), 2 mM sodium orthovanadate (EMD Chemicals, Gibbstown, N.J., #567540), protease inhibitor (Sigma, St. Louis, Mo.; #P8340), phosphatase inhibitor cocktail I (Sigma #P2850), and phosphatase inhibitor cocktail II (Sigma #P5726)) per well and incubated on ice for 15-20 min. Cell lysates are used in the ELISA assay described below to determine the phosphorylation of c-Met at residue Y1349.

c-Met capture antibody is diluted in Bup H coating buffer (Thermo Fisher Scientific, Waltham, Mass., #28382) to 2 µg/mL, added to ELISA plates (Greiner Bio-One, Monroe, N.C., #655081) and incubated overnight at 4° C. The wells are aspirated, washed three times with TBS-T (BioFX, Owings Mills, Md., WSH-1000-01), and then blocked with 200 µL of blocking buffer (TBS-T plus 2% (w/v) BSA) for 1 hour at room temperature. The plates are washed three times with TBS-T. Next, 25 µL of cell lysates plus 75 µL blocking buffer are added, and the plates are incubated overnight at 4° C. The plates are then washed three times with TBS-T. 100 µl of 0.5 µg/mL of pY1349 c-Met polyclonal antibody (Cell Signaling Technology, Danvers, Mass., #3133) in blocking buffer are added to each well, and incubated for 2 hours at room temperature. The plates are then washed three times with TBS-T. 100 µL of 1/10,000 diluted peroxidase-conjugated goat anti-rabbit IgG polyclonal antibody (Jackson ImmunoResearch Laboratories, West Grove, Pa., #111-035-144) in blocking buffer are added to each well and incubated 1 hour at room temperature. The plates are then washed three times with TBS-T. 100 µL of 3,3',5,5'-tetramethylbenzidine solution (BioFX, #TMBW-1000-01) are added to each well, followed by the addition of 100 µl stop solution (BioFX, #LSTP-1000-01). The plates are read at 450 nm on a SpectraMax M5 plate reader (Molecular Devices, Sunnyvale, Calif.) and sample values are determined using SOFTmax Pro 4.8 software (Molecular Devices).

The results are shown in Table 8.

TABLE 8

Effect of c-Met Antibodies, HGF, and Agonist Mab 5D5 on c-Met Phosphorylation in A549 Cells

| Ab Conc. (µg/mL) | p-Met signal C8-H241 | p-Met signal C8-6 | p-Met signal hIgG4 |
|---|---|---|---|
| 30 | 0.333 | 0.272 | 0.061 |
| 10 | 0.418 | 0.334 | 0.077 |
| 3.333 | 0.450 | 0.328 | 0.068 |
| 1.113 | 0.465 | 0.365 | 0.087 |
| 0.370 | 0.340 | 0.211 | 0.082 |
| 0.123 | 0.304 | 0.127 | 0.067 |
| 0.041 | 0.130 | 0.125 | 0.268 |
| 0.014 | 0.078 | 0.105 | 0.074 |
| 0.005 | 0.074 | 0.070 | 0.074 |
| 0.002 | 0.070 | 0.081 | 0.117 |

| HGF Conc. (ng/mL) | p-Met signal | Ab Conc. (ng/mL) | p-Met signal Mab 5D5 |
|---|---|---|---|
| 300 | 10.615 | 5 | 3.290 |
| 100 | 6.129 | | |
| 33.33333 | 2.267 | | |
| 11.11111 | 1.0667 | | |
| 3.703704 | 0.461 | | |
| 1.234568 | 0.211 | | |
| 0.411523 | 0.142 | | |
| 0.137174 | 0.128 | | |
| 0.045725 | 0.100 | | |
| 0.015242 | 0.148 | | |

The data demonstrate that HGF and agonist c-Met Mab 5D5 strongly stimulate c-Met phosphorylation, while present c-Met Mabs C8-H241 and C8-6 weakly stimulate c-Met phosphorylation. Similar results are obtained in HCT 116, H460, and MDA-MB-231 cell lines.

Mab D11-8B8 yields similar results.

EXAMPLE 7 c-Met Antibodies Inhibit HGF-Induced c-Met Phosphorylation

Binding of HGF to c-Met results in tyrosine phosphorylation of c-Met molecules and activation of the c-Met signaling pathway. In this example, human colon cancer cell line HCT116, which is responsive to HGF, is used to assess the inhibition of HGF-induced phosphorylation at tyrosine residues 1230, 1234, and 1235 of c-Met by the present c-Met antibodies.

HCT116 cells (ATCC, Manassas, Va., #CCL-247) are resuspended to 150,000 cells/mL in McCoy's 5A medium (Invitrogen, Carlsbad, Calif., #16600-082) plus penicillin/streptomycin (Invitrogen, #15140-122) with 10% (v/v) fetal bovine serum (FBS) (Invitrogen, #10082-147). 0.2 mL of the resuspended HCT116 cells are added to 96-well microtiter plates (Corning, Lowell, Mass., #3596) at 30,000 cells/well, and the cells are then incubated for 48 hours at 37° C. under 5% (v/v) $CO_2$. The culture medium is then aspirated and the cells are starved in 100 µL of McCoy's 5A medium plus penicillin/streptomycin with 0.1% (w/v) BSA for 24 hours at 37° C. under 5% (v/v) $CO_2$. 25 µL of sodium azide (final concentration of 0.01% (w/v)) (Sigma, #S2002) are added, followed immediately by adding 25 µL of 8×c-Met antibody dilutions to McCoy's 5A medium plus penicillin/streptomycin with 0.1% (w/v) BSA, and the cells are incubated for 30 min. at 37° C. under 5% (v/v) $CO_2$. 50 µL of HGF at a final concentration of 200 ng/mL are added to each well and the cells are incubated for an additional 15 min. at 37° C. under 5% (v/v) $CO_2$ The medium is then aspirated and 50 µL of cell lysis buffer are added (10 mM Tris (Invitrogen, #15567-027), 150 mM NaCl, 2 mM ethylenediaminetetraacetic acid (EDTA) (Invitrogen, #15575-038), 50 mM NaF (Sigma, #S1504), 1% (v/v) octylphenoxy polyethoxy ethanol (TRITON®-X 100; Sigma, #T8787), 2 mM sodium orthovanadate (EMD Chemicals, Gibbstown, N.J., #567540), and complete protease inhibitor, EDTA free (Roche, Basel, Switzerland,

11836170001). Cells are incubated in the lysis buffer at room temperature for 15-30 min. Cell lysates are assayed for c-Met tyrosine phosphorylation by ELISA as follows.

c-Met capture antibody is diluted in coating buffer (BioFX, Glendora, Calif., COAT-1000-01) to 2 µg/mL. 110 µL of the diluted antibody are added per well to ELISA plates (Greiner Bio-One, Monroe, N.C., #655081) and the plates are incubated overnight at 4° C. The wells are aspirated, washed twice with TBS-T, and then blocked with 200 µL of blocking buffer (TBS-T plus 2% (w/v) BSA) for 1 hour. The plates are washed twice with TBS-T. Next, 25 µL of cell lysates plus 75 µL blocking buffer or 100 µL of MKN45 cell lysate dilutions (diluted with blocking buffer, as a standard) are added, and the plates are incubated for 2 hours at room temperature. The plates are then washed four times with TBS-T. 100 µL of 0.5 µg/mL of pYpYpY1230/1234/1235 c-Met polyclonal antibody (Invitrogen, #44-888G) in blocking buffer are then added to each well, and the plates are incubated for 2 hours at room temperature. Next, the plates are washed four times with TBS-T. 100 µL of 1/12,000 diluted peroxidase-conjugated goat anti-rabbit IgG polyclonal antibody (Jackson ImmunoResearch Laboratories, West Grove, Pa., #111-035-144) in blocking buffer are then added, and the mixture is incubated for 1 hour at room temperature. The plates are then washed six times with TBS-T. 100 µL of 3,3',5,5'-tetramethylbenzidine solution (BioFX, #TMBW-1000-01) are added to each well, followed by the addition of 100 µL stop solution (BioFX, #LSTP-1000-01). The plates are read at 450 nm with a 570 nm correction using a SpectraMax 190 plate reader (Molecular Devices, Sunnyvale, Calif.). The standard curve is established using 4-para-meter analysis, and sample values are determined using SOFTmax Pro 3.1.2 software (Molecular Devices).

The percentage of inhibition of c-Met tyrosine phosphorylation is set at the average of HGF treatment without c-Met antibody addition (0% inhibition), and 100% inhibition is set at the average of sodium azide treatment (no HGF or c-Met antibody treatment).

Table 9 shows the average of triplicate treatments per experiment for three experiments with standard errors. The data demonstrate that five of six c-Met antibodies of the present invention significantly inhibit HGF-induced tyrosine phosphorylation of c-Met compared to that of the human IgG2 and IgG4 isotype controls.

TABLE 9

Percent Inhibition of HGF-Induced c-Met Tyrosine Phosphorylation By C8- and D11- Antibodies

| Ab treatment | isotype | 10 µg/mL average | sterr | 2 µg/mL average | sterr | 0.4 µg/mL average | sterr | 0.08 µg/mL average | sterr | 0.016 µg/mL average | sterr | 0.0032 µg/mL average | sterr |
|---|---|---|---|---|---|---|---|---|---|---|---|---|---|
| D11-8B8 | IgG2 | 19.56 | 4.68 | 40.74 | 8.24 | 35.04 | 6.43 | 10.52 | 7.41 | −6.68 | 9.48 | −10.37 | 6.79 |
| D11-C27G3 | IgG2 | 1.25 | 7.55 | 31.78 | 7.71 | 38.10 | 4.97 | 20.79 | 5.72 | 5.73 | 8.95 | 9.72 | 7.09 |
| D11-S17Y | IgG2 | 16.73 | 8.72 | 31.39 | 6.43 | 15.91 | 6.05 | −3.24 | 10.54 | 2.53 | 8.52 | 9.48 | 8.51 |
| C8-H241 | IgG4 | 60.08 | 5.27 | 62.20 | 2.10 | 59.09 | 3.05 | 22.09 | 4.92 | 14.68 | 12.40 | −12.33 | 10.18 |
| C8-co-16 | IgG4 | 65.40 | 3.94 | 58.96 | 3.37 | 45.08 | 3.44 | 9.77 | 9.14 | −2.89 | 10.95 | −10.72 | 5.41 |
| C8-6 | IgG4 | 14.88 | 10.78 | 27.94 | 3.80 | 16.83 | 4.36 | 7.79 | 7.68 | −6.06 | 8.84 | −11.34 | 8.65 |
| 5D5 | mIgG1 | 64.12 | 3.31 | 63.75 | 4.44 | 42.55 | 4.27 | 11.87 | 7.73 | −3.50 | 9.70 | −6.07 | 5.68 |
| hIgG2 | isotype control | 6.24 | 5.31 | 17.53 | 5.74 | 9.31 | 6.56 | −1.58 | 8.16 | 9.49 | 6.77 | −10.21 | 6.78 |
| hIgG4 | isotype control | −1.47 | 5.76 | −6.62 | 9.07 | −16.07 | 7.01 | −21.70 | 9.09 | −7.96 | 10.97 | −14.40 | 7.37 |
| mIgG1 | isotype control | 5.46 | 6.31 | 9.76 | 9.27 | 13.43 | 8.18 | −10.59 | 10.31 | −5.42 | 10.53 | −9.76 | 8.42 |

| | | ave | sterr |
|---|---|---|---|
| untreated | | 100.00 | 0.98 |
| HGF | 200 ng/mL | 0.00 | 2.76 |

% inhibition of HGF stimulated phospho-Met as measured by ELISA

EXAMPLE 8

Induction of c-Met Internalization by c-Met Antibodies

The experiments described in this example employ fluorescence-activated cell sorting (FACS) analysis to demonstrate that the present c-Met antibodies bind to cell surface c-Met molecules and induce c-Met internalization. The MKN45 cells employed constitutively express high levels of total c-Met, and exhibit HGF-independent phosphorylation of c-Met as a result of MET gene amplification. c-Met internalization appears to induce c-Met degradation (see Examples 10 and 19), resulting in inhibition of the c-Met signaling pathway.

Wells of 6-well tissue culture plates (Costar, #3598) are seeded with $1.5 \times 10^5$ human gastric tumor MKN45 cells (Japan Health Sciences Foundation, Health Science Research Resource Bank, #JCRB0254) in 2 mL of culture medium (RPMI-1640 (Invitrogen, #11835); 10% (v/v) FBS (Invitrogen, #10082); 2 mM L-glutamine (Invitrogen, #25030); 100 U/500 mL penicillin G, and 100 μg/500 mL streptomycin (Invitrogen, #15140)). The plates are incubated for 24 hours at 37° C. under 95% relative humidity and 5% (v/v) $CO_2$. Antibodies are then added to the wells at a final concentration of 5 μg/mL. After overnight treatment, the culture medium is removed from the wells and replaced with 1 mL of enzyme-free cell dissociation solution (Chemicon, #S-0,4-B). The cells are collected into centrifuge tubes after being incubated for 5 min. at room temperature, and washed once in culture medium followed by one more wash in binding buffer (DPBS with 1% (w/v) BSA and 0.01% (w/v) sodium azide). Before staining cells, a c-Met antibody that recognizes a different epitope from the present c-Met antibodies is labeled by using an Alexa Fluor 488 Monoclonal Antibody Labeling Kit (Molecular Probes, Eugene, Oreg., #A-20181) according to the supplier's instructions. 100 μL of binding buffer containing 2 μg/mL of the Alexa Fluor 488-labeled antibody are added to the cells, which are then incubated for 60 min. on ice. The cells are then washed once with binding buffer and resuspended in DPBS containing 2 μg/mL propidium iodide (to stain the dead cells). The amount of c-Met molecules remaining on the cell surface is analyzed by FACS analysis, and 10,000 events are acquired for each sample.

The mean fluorescence intensity on the cell surface reflects the quantity of c-Met molecules that remain on the cell surface after treatment with c-Met antibodies.

The data from one representative experiment are shown in Table 10.

Complementary internalization results are obtained by confocal microscopy using fluorescently labeled murine C8 antibody in MKN45 and Caki-1 cells.

Using C8-H241, C8-6, C8-co-16, and murine D11 antibodies, similar internalization results are obtained in cynomolgous monkey NIH3T3 cells transfected with nucleic acid encoding cynomolgus monkey c-Met.

C8-H241, C8-6, C8-co-16, and optD11 antibodies also induce internalization of c-Met in NIH3T3 cells transfected with nucleic acid encoding human c-Met kinase domain mutation M1149T. Antibodies C8-H241, C8-6, C8-co-16, and murine D11 also induce internalization of c-Met in non-small cell lung cancer H1437 cells containing c-Met juxtamembrane domain mutation R988c. Both mutations cause gain-of-function constitutive activation of the c-Met.

EXAMPLE 9

Antibody Inhibition of Ligand-Independent Tumor Cell Proliferation In Vitro

The inhibition of tumor cell growth in vitro by c-Met antibodies in HGF-independent MKN45 cells in the absence of HGF ligand is examined in this assay.

c-Met and isotype control antibodies are diluted with culture medium (RPMI-1640 (Invitrogen, #11835), 10% (v/v) FBS, 2 mM L-glutamine (Invitrogen, #25030), 100 U/500 mL penicillin G, and 100 ng/500 mL streptomycin (Invitrogen, #15140)) to achieve 2× the final concentrations indicated in Table 11, and 50 μL of the 2× antibody solutions are added to each well of 96-well tissue culture plates (Perki-

TABLE 10

Effect of C8- and D11- Antibodies on
c-Met Internalization as Determined by FACS Analysis
Mean Fluorescence

| Antibody (ug/mL) | hIgG2 | D11-8B8 | D11-C27G3 | D11-S17Y | hIgG4 | C8-6 | C8-H241 | C8-co16 | mIgG | 5D5 |
|---|---|---|---|---|---|---|---|---|---|---|
| 5.00 | 130.25 | 44.66 | 51.09 | 56.35 | 135.03 | 67.88 | 57.63 | 56.16 | 136.47 | 92.87 |

The data demonstrate that the mean fluorescence intensity on the surface of cells treated with the present c-Met antibodies is lower than that in cells treated with a corresponding IgG isotype control antibody or mIgG antibody, indicating that the present c-Met antibodies induce c-Met internalization. Moreover, the mean fluorescence intensity on the surface of the cells treated with the present c-Met antibodies is lower than that in cells treated with control agonist c-Met antibody 5D5. % internalization may be calculated as follows % internalization=[1−(mean fluorescence of test antibody divided by mean fluorescence of isotype antibody control)]multiplied by 100].

The internalization data suggest that the present antibodies induce dimerization of human c-Met. The data in Examples 9 and 19 demonstrate that C8- and D11-antibodies also induce degradation, and reduce phosphorylation, of c-Met.

nElmer#1450-517). MKN45 cells (Japan Health Sciences Foundation, Health Science Research Resource Bank, #JCRB0254) are maintained in the medium indicated above, and are resuspended to $1 \times 10^5$ cells/mL in the same medium. 50 μL of this MKN45 resuspension are added to each well to achieve $5 \times 10^3$ cells/well. The plates are then incubated for 48 hours at 37° C. under 95% relative humidity and 5% (v/v) $CO_2$. For the last six hours of the culture, the cells are pulsed with $^3$H-thymidine (MP Biomedicals, Solon, Ohio #24066) at 1 uci/well at 37° C., 95% relative humidity, 5% (v/v) $CO_2$. The medium is then removed and the cells are washed once with DPBS. After this, 200 μL of Optiphase Supermix (PerkinElmer, #1200-439) are added to each well. The plates are sealed and incubated for at least one hour at room temperature. $^3$H-thymidine incorporated in the cells is counted for one min. using a scintillation counter.

The data from one representative experiment are shown in Table 11.

TABLE 11

Inhibition of $^3$H-Thymidine Incorporation in MKN45 Cells by Various C8- and D11- Antibodies

| Antibody dose (ng/mL) | hIgG2 | D11-8B8 | D11-27G3 | D11-S17Y | hIgG4 | C8-co16 | C8-H241 | C8-6 | mIgG | 5D5 |
|---|---|---|---|---|---|---|---|---|---|---|
| AVG CPM | | | | | | | | | | |
| 20000.0 | 45054 | 11239 | 18407 | 19752 | 50628 | 11738 | 11425 | 16387 | 52448 | 35086 |
| 3333.3 | 49384 | 11441 | 16920 | 21239 | 54026 | 12956 | 12063 | 18216 | 53670 | 38195 |
| 555.6 | 51720 | 11925 | 15987 | 20936 | 54204 | 13476 | 13217 | 18334 | 54655 | 39496 |
| 92.6 | 47562 | 11094 | 14550 | 21911 | 54264 | 12419 | 11962 | 23041 | 52241 | 39607 |
| 15.4 | 50488 | 24402 | 28685 | 39695 | 53806 | 22528 | 23150 | 44771 | 51329 | 49766 |
| 2.6 | 48491 | 44741 | 47034 | 49868 | 54765 | 53465 | 48761 | 54598 | 55463 | 54967 |
| 0.4 | 46468 | 43334 | 43998 | 45304 | 55330 | 47485 | 46645 | 53389 | 51549 | 49563 |
| 0.1 | 44822 | 41578 | 41515 | 44566 | 53856 | 45725 | 44418 | 51668 | 47709 | 51883 |
| 0.0 | 50427 | 50427 | 44213 | 44213 | 48708 | 51478 | 51478 | 48708 | 50300 | 50300 |
| STDErr | | | | | | | | | | |
| 20000.0 | 2927 | 114 | 1265 | 1206 | 2491 | 262 | 654 | 282 | 1845 | 764 |
| 3333.3 | 2462 | 732 | 641 | 689 | 1421 | 388 | 386 | 314 | 1310 | 1491 |
| 555.6 | 2166 | 605 | 578 | 267 | 4364 | 281 | 341 | 1116 | 1192 | 534 |
| 92.6 | 1835 | 22 | 150 | 564 | 1733 | 352 | 636 | 475 | 1036 | 370 |
| 15.4 | 2144 | 2024 | 941 | 463 | 1376 | 207 | 1771 | 422 | 1281 | 968 |
| 2.6 | 2587 | 1914 | 1133 | 1910 | 1978 | 2164 | 1945 | 444 | 919 | 2577 |
| 0.4 | 2041 | 650 | 1177 | 2551 | 1501 | 378 | 2392 | 162 | 438 | 1943 |
| 0.1 | 1628 | 1734 | 1817 | 2402 | 678 | 1340 | 2442 | 1589 | 2092 | 3143 |
| 0.0 | 1203 | 1203 | 841 | 841 | 1377 | 886 | 886 | 1377 | 777 | 777 |

Abbreviations:
AVG = average;
CPM = count per minute;
STDErr = Standard Error

These data demonstrate that various C8- and D11-c-Met antibodies of the present invention inhibit HGF-independent MKN45 cell proliferation as evidenced by a reduction in $^3$H-thymidine incorporation. Similar results are obtained in SNU5 and NUGC-4 tumor cells, which each exhibit constitutive overexpression and phosphorylation of c-Met.

EXAMPLE 10

Reduction of Phosphorylated and Total c-Met, and Lack of Shedding of c-Met Extracellular Domain, in Response to c-Met Antibodies This example investigates whether treatment of MKN45 cells with c-Met antibodies of the present invention results in reduction of phosphorylated c-Met (p-Met) and total c-Met. In addition, this assay is used to determine if c-Met antibody treatment induces the shedding of c-Met ECD into MKN45-conditioned medium.

c-Met and isotype control antibodies are diluted with culture medium (RPMI-1640 (Invitrogen, #11835), 10% (v/v) FBS (Invitrogen, #10082), 2 mM L-glutamine (Invitrogen, #25030), 100 U/500 mL penicillin G, and 100 µg/500 mL streptomycin (Invitrogen, #15140)) to achieve 2× the final concentrations indicated in Table 12, and 50 µL of the 2× antibody solutions are added to each well of 96-well tissue culture plates (Costar, #3596). MKN45 cells (Japan Health Sciences Foundation, Health Science Research Resource Bank, #JCRB0254) are maintained in the medium indicated above and are resuspended to 1×10$^5$ cells/mL in the same medium. 50 µL of this MKN45 resuspension are added to each well to achieve 5×10$^3$ cells/well. The plates are then incubated for 24 hours at 37° C. under 95% relative humidity and 5% (v/v) CO$_2$, and cell lysates are prepared as described in Example 7. In addition, the conditioned medium from each treatment is collected for c-Met-ECD quantitation. p-Met and total c-Met levels in the cell lysates are determined by ELISA, and normalized to lysate protein concentration (as determined by BCA, Pierce #23225).

Phosphorylated c-Met

Phosphorylation of c-Met at tyrosine residues 1230, 1234, and 1235 is determined as described in Example 7.

Total c-Met and c-Met ECD Shedding

For the total c-Met and c-Met ECD ELISAs, a c-Met capture antibody is diluted in coating buffer (BioFX, Glendora, Calif., COAT-1000-01) to 2 µg/mL. 110 µL of the diluted antibody are added per well to ELISA plates (Greiner Bio-One, Monroe, N.C., #655081) and the plates are incubated overnight at 4° C. The wells are aspirated, washed twice with TBS-T, and then blocked with 200 µL of blocking buffer (TBS-T plus 2% (w/v) BSA) for 1 hour at room temperature. The plates are then washed twice with TBS-T. Next, MKN45 cell lysates, MKN45 conditioned medium, or c-Met extracellular domain (ECD) (SEQ ID NO:75) (as a standard), are added, and the plates are incubated for 2 hours at room temperature. The plates are then washed four times with TBS-T. 100 µl of 0.5 µg/mL of a biotinylated second c-Met antibody (Mab 5D5) that binds a different c-Met epitope from the capture antibody diluted in blocking buffer are then added to each well, and the plates are incubated for 2 hours at room temperature. Next, the plates are washed four times with TBS-T. 100 µL of 1/12,000 diluted peroxidase-conjugated streptavidin (Jackson ImmunoResearch Laboratories, West Grove, Pa., #016-030-084) in blocking buffer are then added, and the mixture is incubated for 1 hour at room temperature. The plates are then washed six times with TBS-T. 100 µL of 3,3',5,5'-tetramethylbenzidine solution (BioFX, #TMBW-1000-01) are added to each well, followed by the addition of 100 µL stop solution (BioFX, #LSTP-1000-01). The plates are read at 450 nm with a 570 nm correction using a Spectra-Max 190 plate reader (Molecular Devices, Sunnyvale, Calif.). The standard curve is established using 4-para-meter analysis, and sample values are determined using SOFTmax Pro 3.1.2 software (Molecular Devices).

As shown in Table 12, the p-Met and total c-Met ELISA data reveal that Mab C8-H241 treatment maximally reduces p-Met by 77% and total c-Met by approximately 67%. D11-8B8 treatment maximally reduces p-Met by approximately 75% and total c-Met by 63%.

As noted in Example 8, these data demonstrate that C8- and D11-antibodies induce c-Met degradation and reduce phosphorylation of c-Met.

The data in Table 12 also indicate that treatment with C8-H241 and D11-8B8 c-Met antibodies does not induce cleavage and shedding of the c-Met ECD.

TABLE 12

Effect of C8- and D11- Antibodies on Phosphorylated c-Met, Total c-Met, and Shedding of c-Met Extracellular Domain in MKN45 Cell Lysates and Conditioned Medium

| Mab Dose | C8-H241 | | hIgG4 | | D11-8B8 | | hIgG2 | |
|---|---|---|---|---|---|---|---|---|
| (ng/mL) | ave | stdev | ave | stdev | ave | stdev | ave | stdev |
| Percent Inhibition of MKN45 Phosphorylated c-Met | | | | | | | | |
| 10000 | 77.0 | 2.4 | −2.1 | 10.9 | 74.8 | 3.4 | 14.0 | 7.1 |
| 1000 | 74.1 | 1.3 | 11.1 | 9.7 | 72.8 | 2.0 | −4.6 | 10.9 |
| 100 | 71.7 | 2.5 | 13.4 | 13.3 | 69.1 | 3.7 | −7.6 | 24.4 |
| 10 | 42.3 | 3.0 | 5.8 | 11.3 | 37.6 | 5.5 | 6.1 | 11.0 |
| untreated | 0.0 | 8.0 | | | | | | |
| Percent Inhibition of MKN45 Total c-Met | | | | | | | | |
| 10000 | 63.1 | 1.6 | −23.7 | 4.1 | 63.0 | 7.0 | 14.1 | 9.1 |
| 1000 | 66.7 | 4.3 | 10.4 | 16.0 | 62.7 | 0.6 | −2.4 | 22.4 |
| 100 | 61.5 | 3.4 | −3.7 | 14.4 | 62.9 | 2.5 | 7.3 | 9.1 |
| 10 | 32.3 | 4.9 | −3.4 | 13.5 | 34.5 | 8.4 | 15.1 | 7.0 |
| untreated | 0.0 | 25.9 | | | | | | |
| Level of c-Met ECD in MKN45-Conditioned Medium (ng/mL) | | | | | | | | |
| 10000 | 5.1 | 0.5 | 7.4 | 0.7 | 6.2 | 0.2 | 7.0 | 0.1 |
| 1000 | 6.1 | 0.8 | 7.6 | 0.4 | 7.2 | 0.5 | 7.2 | 0.5 |
| 100 | 5.4 | 0.4 | 7.6 | 0.8 | 6.9 | 1.6 | 7.2 | 0.6 |
| 10 | 6.6 | 0.2 | 8.4 | 1.1 | 6.2 | 0.4 | 7.2 | 0.1 |
| untreated | 8.3 | 1.0 | | | | | | |

EXAMPLE 11

Agonist Activity of Antibodies in Caki-1 Tumor Cells in the Absence of HGF

Caki-1 renal carcinoma cells proliferate in response to HGF. The activation of c-Met in Caki-1 cells by c-Met antibodies in the absence of HGF is examined in this example to assess the agonist activity of c-Met antibodies of the present invention.

Wells of 96-well tissue culture plates are seeded with 5,000 human kidney clear cell carcinoma Caki-1 cells (ATCC, #HTB-46) in McCoy's 5A culture medium (Invitrogen, #16600) supplemented with 10% (v/v) FBS, 2 mM L-glutamine (Invitrogen, #25030), 100 U/500 mL penicillin G and 100 mg/500 mL streptomycin (Invitrogen, #15140). After culture for 24 hours, cells are starved in low serum medium (0.5% (v/v) FBS) for another 24 hours. The cells are then cultured in the presence of anti-c-Met and control antibodies in low serum medium at final concentrations as indicated in Table 13 for 24 hours at 37° C., 95% relative humidity, 5% (v/v) $CO_2$. For the last six hours of the culture, the cells are pulsed with $^3$H-thymidine (MP Biomedicals, Solon, Ohio #24066) at 1 μci/well at 37° C., 95% relative humidity, 5% (v/v) $CO_2$. Next, the medium is removed and the cells are washed once with DPBS. After this, 200 μL of Optiphase Supermix (PerkinElmer, #1200-439) are added to each well. The plates are then sealed and incubated for at least one hour at room temperature. $^3$H-thymidine incorporated in the cells is counted for one min. using a scintillation counter.

The data from one representative experiment are shown in Table 13.

TABLE 13

Effect of C8- and D11- Antibodies on $^3$H-Thymidine Incorporation in Caki-1 Cells in the Absence of HGF

| Antibody dose (ng/mL) | hIgG2 | D11-8B8 | D11-27G3 | D11-S17Y | hIgG4 | C8-co16 | C8-H241 | C8-6 | mIgG | 5D5 |
|---|---|---|---|---|---|---|---|---|---|---|
| AVG CPM | | | | | | | | | | |
| 20000.0 | 14658 | 15866 | 16054 | 18616 | 13704 | 13112 | 12797 | 13194 | 14224 | 19893 |
| 3333.3 | 14034 | 15730 | 15765 | 17897 | 13023 | 13829 | 12702 | 13193 | 13469 | 19018 |
| 555.6 | 14048 | 13997 | 14536 | 16620 | 12393 | 11359 | 12116 | 13494 | 13200 | 20043 |
| 92.6 | 14113 | 13705 | 14718 | 15342 | 12934 | 11563 | 12142 | 12793 | 13761 | 15588 |
| 15.4 | 14473 | 13488 | 13836 | 14579 | 13271 | 12111 | 13020 | 13670 | 13638 | 11748 |
| 2.6 | 15517 | 14097 | 13325 | 14867 | 13858 | 13713 | 14407 | 14126 | 13766 | 12520 |
| 0.4 | 14341 | 14411 | 13596 | 14618 | 13412 | 14080 | 14142 | 14601 | 14357 | 12896 |
| 0.1 | 16947 | 15319 | 17690 | 15899 | 13547 | 15567 | 15530 | 16121 | 13797 | 14383 |
| 0.0 | 14992 | 14992 | 15237 | 15237 | 14622 | 13889 | 14622 | 13889 | 14531 | 14531 |
| STDErr | | | | | | | | | | |
| 20000.0 | 398 | 737 | 549 | 345 | 219 | 642 | 268 | 96 | 465 | 807 |
| 3333.3 | 358 | 959 | 538 | 466 | 84 | 1086 | 380 | 382 | 927 | 954 |
| 555.6 | 343 | 809 | 705 | 284 | 478 | 437 | 216 | 4 | 397 | 505 |
| 92.6 | 428 | 502 | 728 | 237 | 447 | 292 | 445 | 212 | 706 | 394 |
| 15.4 | 232 | 737 | 729 | 160 | 487 | 267 | 305 | 107 | 514 | 318 |
| 2.6 | 386 | 173 | 295 | 404 | 339 | 299 | 291 | 711 | 91 | 221 |
| 0.4 | 357 | 568 | 508 | 392 | 317 | 556 | 656 | 281 | 331 | 323 |

TABLE 13-continued

Effect of C8- and D11- Antibodies on $^3$H-Thymidine Incorporation in Caki-1 Cells in the Absence of HGF

| Antibody dose (ng/mL) | hIgG2 | D11-8B8 | D11-27G3 | D11-S17Y | hIgG4 | C8-co16 | C8-H241 | C8-6 | mIgG | 5D5 |
|---|---|---|---|---|---|---|---|---|---|---|
| 0.1 | 262 | 550 | 1108 | 326 | 381 | 601 | 583 | 536 | 229 | 145 |
| 0.0 | 310 | 310 | 394 | 394 | 364 | 554 | 364 | 554 | 238 | 238 |

Abbreviations:
AVG = average;
CPM = count per minute;
STDErr = Standard Error

These data demonstrate that c-Met antibodies C8-H241, C8-6, C8-co-16, and D11-8B8 do not significantly increase the uptake of thymidine-[methyl-3H] in Caki-1 cells compared to that of the IgG isotype controls. D11-C27G3 and D11-S17Y exhibit a low, variable, but statistically significant stimulation of thymidine-[methyl-3H] uptake in Caki-1 cells compared to that of the IgG isotype control. The control c-Met agonist antibody 5D5 induces stronger thymidine-[methyl-3H] uptake than that of the present c-Met antibodies in Caki-1 cells under the same experimental conditions.

EXAMPLE 12

Agonist Activity of Antibodies in Primary Human Hepatocytes in the Absence of HGF The agonist activity of the present c-Met antibodies is further assessed in primary human hepatocytes (PHH), which are HGF-responsive, in the absence of HGF.

Cryopreserved, plateable PHH cells (KQG Celsis, Chicago, Ill., RD#00002) are thawed at 37° C. and resuspended to 175,000 cells/mL in InVitroGRO CP medium (Celsis, #Z99029) with torpedo antibiotic mix (Celsis, #Z99000). 0.2 mL of resuspended PHH cells are added per well to collagen I coated 96-well microtiter plates (BD, Franklin Lakes, N.J., #354407) at 35,000 cells/well, and the cells are incubated for 24 hours at 37° C., 5% (v/v) $CO_2$. The culture medium is then aspirated and 150 μL of InVitroGRO HI medium (Celsis, #Z99009) with torpedo antibiotic mix plus 0.1% (w/v) BSA are added per well, plus 50 μL of c-Met and control antibodies in a final concentration range of 10 lag/mL to 0.0032 μg/mL, or HGF at a final concentration of 200 ng/mL, in InVitroGRO HI medium with torpedo antibiotic mix plus 0.1% (w/v) BSA. Cells are incubated for 48 hours at 37° C., 5% (v/v) $CO_2$, and 10 μL of 0.1 mCi thymidine-[methyl-3H]/mL (MP Biomedicals, Solon, Ohio, #24066) are added per well for the last 6 hours of incubation. Assay plates are frozen at −70° C., thawed at 37° C., and harvested onto UniFilter-96, GF/C plates (Perkin Elmer, Waltham, Mass., #6005174) using a Filtermate Harvester (Perkin Elmer). The UniFilter plates are dried, 20 μL of Microscint 0 scintillant (Perkin Elmer, #6013611) are added per well, and plates are counted on a 1450 Microbeta liquid scintillation counter (Perkin Elmer).

Table 14 shows the average of triplicate treatments with standard deviations, and is representative of three repeat experiments.

TABLE 14

Effect of Various C8- and D11- Antibodies on $^3$H-Thymidine Incorporation in Primary Human Hepatocytes in the Absence of HGF

| | | Doses: | | | | | | | | | | | |
|---|---|---|---|---|---|---|---|---|---|---|---|---|---|
| | | 10 μg/mL | | 2 μg/mL | | 0.4 μg/mL | | 0.08 μg/mL | | 0.016 μg/mL | | 0.0032 μg/mL | |
| Ab treatment | isotype | average | stdev | average | stdev | average | stdev | average | stdev | average | stdev | average | stdev |
| D11-8B8 | IgG2 | 1703.7 | 140.1 | 1427.0 | 120.3 | 1231.0 | 232.4 | 1122.7 | 188.3 | 715.3 | 25.8 | 611.0 | 61.5 |
| D11-C27G3 | IgG2 | 2145.7 | 171.0 | 1874.0 | 443.4 | 1753.0 | 199.8 | 1283.3 | 131.6 | 892.0 | 109.3 | 692.7 | 23.0 |
| D11-S17Y | IgG2 | 3155.0 | 594.2 | 2566.0 | 173.1 | 1911.0 | 348.3 | 1458.7 | 132.7 | 919.7 | 47.5 | 726.3 | 131.7 |
| C8-H241 | IgG4 | 671.0 | 61.0 | 710.3 | 81.8 | 681.3 | 13.7 | 669.3 | 77.0 | 630.0 | 37.2 | 625.0 | 65.5 |
| C8-co-16 | IgG4 | 952.0 | 36.0 | 822.0 | 88.4 | 670.0 | 23.3 | 767.3 | 12.6 | 715.7 | 12.5 | 828.7 | 85.2 |
| C8-6 | IgG4 | 1042.3 | 91.3 | 892.3 | 107.0 | 801.7 | 77.4 | 792.3 | 48.4 | 769.7 | 109.9 | 736.3 | 43.1 |
| 5D5 | mIgG1 | 4978.0 | 59.9 | 4912.3 | 287.7 | 3763.7 | 292.1 | 3320.7 | 40.1 | 1716.3 | 324.1 | 821.7 | 175.3 |
| hIgG2 | isotype control | 650.0 | 39.4 | 643.7 | 11.7 | 711.7 | 16.6 | 836.0 | 61.0 | 748.3 | 57.7 | 799.7 | 80.3 |
| hIgG4 | isotype control | 647.3 | 77.1 | 735.0 | 33.8 | 717.3 | 19.4 | 819.0 | 44.2 | 848.3 | 75.1 | 806.7 | 79.7 |
| mIgG1 | isotype control | 616.7 | 24.8 | 581.0 | 81.8 | 601.0 | 82.0 | 596.0 | 78.6 | 588.7 | 43.0 | 675.0 | 73.0 |

| | | | ave | stdev |
|---|---|---|---|---|
| HGF | 200 ng/mL | | 6292.7 | 733.0 |
| untreated | | | 615.1 | 83.9 |

The data demonstrate that compared with the IgG isotype controls, present c-Met antibodies C8-H241 does not significantly increase thymidine-[methyl-3H] uptake in PHH cells; C8-6, C8-co-16, D11-8B8, D11-C27G3, and D11-S17Y exhibit a low, variable, but statistically significant stimulation of thymidine-[methyl-3H] uptake. However, the agonist activity of the present c-Met antibodies is significantly lower than that of the 5D5 control c-Met antibody. Agonist antibody 5D5 stimulates PHH proliferation in a dose-dependent manner, with a 5-fold increase at a concentration of 3 µg/mL. At 200 ng/mL, HGF stimulates a 5-fold increase in $^3$H-thymidine uptake. Mab C8-H241 does not induce proliferation even when used at 10 µg/mL.

Similar results are obtained in human renal epithelial HK2 cells, which also proliferate in response to HGF stimulation.

EXAMPLE 13

Effect of Antibodies on Tubular Morphogenesis in HepG2 Cells in the Absence of HGF HGF induces tubular morphogenic changes in HepG2 cells grown in Matrigel™ (Becton-Dickinson, #354234), an extracellular matrix material containing components of the basement membrane. In this experiment, the HGF-like agonist activity of antibodies of the present invention in inducing tubular morphologic changes in HepG2 cells is assessed.

HepG2 cells (ATCC, #HB-8065) are cultured in DMEM supplemented with 10% FBS. 100 µL of a Matrigel™ solution (Matrigel™, Becton-Dickinson) diluted in Opi-MEMI (Invitrogen, #31985) supplemented with 10% (v/v) FBS, 2 mM L-glutamine (Invitrogen, #25030), 100 U/500 mL penicillin G and 100 µg/500 mL streptomycin (Invitrogen, #15140) are plated in wells of 96-well tissue culture plates (Costar, #3596). After the Matigel™ solution solidifies, 2000 HepG2 cells in 50 µL of culture medium supplemented with 10% serum are added. Next, c-Met and control antibodies at a final concentration of 50 µg/mL, or HGF at a final concentration of 50 ng/mL, are added to the cells. The cells are grown for 4 days at 37° C. in a humidified atmosphere containing 5% (v/v) $CO_2$. After 4 days, the top medium is removed and replaced with 50 µL of 1 mg/mL p-Iodonitro-tetrazolium violet (Sigma, #18377) in PBS, and the cells are incubated for another 48 hours under the same conditions. Photographs are taken of the stained 32 mm area, and analyzed using Image-Pro Plus 6 (Media Cybernetics, Inc., MD).

The data from one representative experiment, for antibodies at 50 µg/mL, are shown in Table 15.

These data demonstrate that HGF and control agonist antibody 5D5 induce approximately 5-fold tubular morphogenic changes in HepG2 cells as compared to the isotype control. In contrast, present c-Met antibodies C8-H241 and C8-co16 do not induce significant tubular morphologic changes in HepG2 cells under the same conditions, while c-Met antibody C8-6 induces only a low level of stimulation.

Similar results are obtained with Mab D11-8-B8.

EXAMPLE 14

Effect of Antibodies on Cell Motility

DU145 Scatter Assay and H441 Cell Scratch Assay

Upon stimulation with HGF, DU145 prostate cancer cells dissociate from each other and H441 cells fill in a scratch made in a confluent cell layer. H441 cells exhibit a high level of c-Met expression and constitutive phosphorylation of this receptor, but are still HGF-responsive. The following experiments assess the agonist effect of antibodies of the present invention on cell motility in a scatter assay and a scratch assay.

DU145 Cell Scatter Assay

DU145 cells (ATCC, # HTB-81) grown in MEM medium (Invitrogen, #11095)+10% FBS (Invitrogen, #10082) at 37° C. under 5% (v/v) $CO_2$ are plated at $2\times10^3$ cells/well in 70 µL volume in black ViewPlate 96-well plates (Perkin Elmer, Waltham, Mass., #6005182) and incubated overnight at 37° C. under 5% (v/v) $CO_2$. c-Met and control antibodies are diluted in the cell culture medium and added at a final concentration of 20 µg/mL, and HGF is added at a final concentration of 20 ng/mL, each in 30 µL volume with twelve replicates, and incubated for 48 hours at 37° C. under 5% (v/v) $CO_2$. The medium is then aspirated and cells are fixed in 2% formaldehyde for 15 min. at room temperature. Wells are washed three times with PBS, and 50 µL of 5 U/mL Alexa Fluor 488 phalloidin (Invitrogen, #A12379) are added for 30 min. at room temperature. Wells are washed three times with PBS, and 50 µL of 15 µM propidium iodide (Invitrogen, #P3566) are added. The plate is subsequently read on an Acumen Explorer™ laser-scanning fluorescence microplate cytometer (TTP Labtech Ltd, Cambridge, Mass.) using Jockyss software in order to determine the percent of DU145 cells in colonies.

TABLE 15

Effect of C8- Antibodies on Tubular Morphogenesis in HepG2 Cells

| Antibody (50 ug/ml) | hIgG4 | C8-H241 | C8-co16 | C8-6 | mIgG | 5D5 | HGF (50 ng/ml) |
|---|---|---|---|---|---|---|---|
| Tubular Morphogenesis Agonist activity (fold stimulation) | no stimulation | no stimulation | no stimulation | 1.2 | 1.2 | 4.9 | 5.4 |

The results are shown in Table 16.

TABLE 16

Effect of C8- and D11- Antibodies on DU145 Cell Scattering

| | Percent of DU145 Cells in Colonies | | | | | | | | |
|---|---|---|---|---|---|---|---|---|---|
| | C8-H241 | C8-6 | C8-co-16 | hIgG4 | D11-8B8 | hIgG2 | 5D5 | HGF | Untreated |
| Average | 24.13 | 23.29 | 23.69 | 24.41 | 25.57 | 25.67 | 14.45 | 8.15 | 26.53 |
| Std. Dev. | 3.35 | 1.37 | 2.30 | 2.02 | 1.98 | 3.13 | 0.34 | 1.23 | 2.44 |

The data demonstrate that agonist c-Met Mab 5D5 and HGF, but not c-Met Mabs C8-H241, C8-co-16, C8-6, or D11-8B8, significantly stimulate DU145 cell scattering/motility.

H441 Cell Scratch Assay

For the H441 Scratch assay, H441 cells (ATCC, # HTB-174) are grown in RPMI-1640 (Invitrogen, #11835); 10% (v/v) FBS (Invitrogen, #10082); 2 mM L-glutamine (Invitrogen, #25030); 100 U/500 mL penicillin G, and 100 mg/500 mL streptomycin (Invitrogen, #15140)), and seeded at $1 \times 10^6$ cells/2 mL/well in wells of 6-well tissue culture plates (Costar, #3598) in the culture medium. The plates are incubated for 3 days under 95% relative humidity and 5% (v/v) $CO_2$. The medium is then aspirated, and the cells are starved in low serum medium (0.5% (v/v) FBS in RPMI medium) for 16 hours. The confluent cell layers on the bottom of the wells are scratched with 5 mL pipette tips in the middle of each well, and floating cells are aspirated. The remaining cells are washed 1× with low serum medium. Low serum medium is added, and the scratched areas are imaged using a bright field microscope with a 4× objective. These gaps are defined as Gaps at 0 hours.

The testing antibodies are added to the cells at a final concentration of 10 μg/mL, followed by incubation at 37° C. under 5% $CO_2$ (v/v) for 16 hours. HGF is tested at a final concentration of 200 ng/mL. Each treatment group is tested at least in duplicate wells. The scratched areas are imaged again using a bright field microscope at 16 hours. These gaps are defined as Gaps at 16 hours.

The effect of c-Met antibodies or HGF on the movement of H441 cells to fill the gaps are calculated as follows:

$$\text{Average percentage change} = \frac{\text{Treatment group (Gap at 0 hour} - \text{Gap at 16 hours)}}{\text{Average medium group (Gap at 0 hour} - \text{Gap at 16 hours)}} \times 100$$

The results are shown in Table 17.

TABLE 17

Effect of C8-antibodies in H441 Scratch Assay

| Antibody (10 μg/mL) | Avg. % | St. Dev. |
|---|---|---|
| Medium | 100 | 7 |
| hIgG4 | 98 | 9 |
| C8-H241 | 98 | 9 |
| C8-6 | 102 | 4 |
| mIgG1 | 98 | 18 |
| Mab 5D5 | 244 | 4 |
| HGF (200 ng/mL) | 364 | 9 |

The data demonstrate that agonist c-Met Mab 5D5 and HGF stimulate movement of H441 cells/filling in of the scratched areas. Under the same conditions, c-Met Mabs C8-H241 and C8-6 do not stimulate H441 cell motility.

EXAMPLE 15

Effect of c-Met Antibodies on HepG2 Cell Invasiveness

HGF and agonist c-Met antibodies stimulate invasion of c-Met bearing cells. This example examines the agonist activity of the present c-Met antibodies in a cell invasion assay employing HepG2 cells, which are HGF-responsive in an invasion assay.

HepG2 cells (ATCC, #HB-8065) are starved overnight in serum-free MEM medium (Invitrogen, #11095) and then $5 \times 10^4$ cells in a total volume of 500 μL are added to each well of the top chamber of a matrigel invasion chamber (BD, Franklin Lakes, N.J., #354483), with the bottom chamber containing antibodies in a total volume of 750 μL of serum-free medium at a concentration of 10 μg/mL, or HGF at 50 ng/mL in serum-free medium, followed by incubation for forty-eight hours at 37° C. under 5% (v/v) $CO_2$. Non-invading cells are removed from the top chamber with a swab, followed by membrane fixation with 95% ethanol and staining with 0.2% (w/v) crystal violet. After washing and drying, the number of invading cells is counted using Image-Pro Plus 6 Manual Tag (Media Cybernetics, Inc., MD) software analysis of photographs taken of stained cells with a 2.5× objective.

The results are summarized in Table 18.

TABLE 18

Effect of C8-, C8, and D11 Antibodies on HepG2 Cell Invasiveness

| Antibody Concentration (μg/mL) | C8-H241 | C8 | mIgG1 | optD11 | 5D5 | HGF (50 ng/mL) | Medium |
|---|---|---|---|---|---|---|---|
|  | hIgG4 | | | | | | |
| 10.00 | 5.5 | 3.5 | 4.3 | 5.5 | 19.8 | 85.0 | 509.5 | 3.5 |
|  | Std. Err. | | | | | | |
|  | 0.5 | 0.9 | 1.3 | 0.5 | 4.1 | 20.4 | 4.5 | 0.5 |

The data demonstrate that agonist c-Met Mab 5D5 and HGF, but not c-Met Mabs C8-H241 and (murine) C8, stimulate HepG2 invasion. Murine c-Met Mab optD11 weakly induces HepG2 cell invasion.

EXAMPLE 16

C8- and D11-Antibodies Do Not Protect Caki-1 Cells from Staurosporine-Induced Apoptosis HGF and agonist c-Met antibodies protect cells from staurosporine-induced cell death. This example examines the agonist activity of c-Met antibodies of the present invention in a staurosporine-induced apoptosis assay employing HGF-responsive Caki-1 cells.

Caki-1 cells (ATCC, #HTB-46) are grown as described in Example 11, seeded at $1 \times 10^4$ cells/well in 96 well plates (Costar, #3596) in culture medium, and pre-treated with antibodies (diluted from 30000 ng/mL to 3 ng/mL in the cell culture medium), or HGF (diluted from 225 ng/mL to 0.02 ng/mL), for one hour followed by treatment with 0.1 μM staurosporine (final concentration) for forty-eight hours at 37° C. The medium is aspirated and the cells are lysed for 30 min. with 0.2 mL of the lysis buffer component of the Cell Death Detection ELISA kit (Roche Applied Science, Indianapolis, Ind., #11774425001). This kit utilizes 20 μL of each lysate to measure cell death by detection of cytoplasmic histone-associated DNA fragments as determined by the absorption at 450 nm. A higher optical density at 450 nm indicates greater apoptosis.

The results shown in Table 19 demonstrate that HGF, but not c-Met Mabs C8-H241, C8-6, and D11-8B8, protects Caki-1 cells from staurosporine-induced apoptosis.

TABLE 19

Effect of c-Met Antibodies on Staurosporine-Induced Apoptosis in Caki-1 Cells

| Antibody dose (ng/mL) | Average A450 nm | | | | | | | |
|---|---|---|---|---|---|---|---|---|
| | C8-H241 | C8-6 | HGF | | hIgG2 | D11-8B8 | Medium | STS* |
| | hIgG4 | | | | | | | |
| 3 | 0.95 | 0.83 | 1.09 | 0.97 (0.02 ng/mL) | 0.95 | 1.02 | 0.24 | 0.87 |
| 30 | 0.98 | 0.84 | 1.02 | 0.93 (0.23 ng/mL) | 0.91 | 0.91 | | |
| 300 | 0.87 | 0.86 | 0.97 | 0.73 (2.25 ng/mL) | 0.95 | 0.81 | | |
| 3000 | 0.98 | 0.85 | 0.92 | 0.58 (22.5 ng/mL) | 0.95 | 0.91 | | |
| 30000 | 0.91 | 0.90 | 0.96 | 0.45 (225 ng/mL) | 0.94 | 0.87 | | |
| | STDErr | | | | | | | |
| 3 | 0.03 | 0.02 | 0.19 | 0.02 | 0.07 | 0.01 | 0.01 | 0.03 |
| 30 | 0.03 | 0.01 | 0.14 | 0.06 | 0.00 | 0.11 | | |
| 300 | 0.10 | 0.03 | 0.06 | 0.03 | 0.02 | 0.02 | | |
| 3000 | 0.04 | 0.01 | 0.12 | 0.01 | 0.06 | 0.02 | | |
| 30000 | 0.00 | 0.01 | 0.13 | 0.06 | 0.04 | 0.03 | | |

*STS: Staurosporine

EXAMPLE 17

Effect of C8-Antibodies on Angiogenesis

HGF and agonist c-Met antibodies stimulate angiogenesis. c-Met antibodies of the present invention are evaluated for this functional agonist property in the ADSC/ECFC co-culture tube formation assay. Adipose-derived stem cells (ADSC) express HGF; endothelial colony forming cells (ECFC) form tubes in response to stimulation by HGF.

ADCS (Lonza, Allendale, N.J., # PT-5006) are dissociated, resuspended in basal medium (MCDB-131 medium (Sigma, St. Louis, Mo. #M8537))+30 µg/mL L-ascorbic acid 2-phosphate (Sigma #A8960), 1 µM dexamethasone (Sigma #D4902), 50 µg/mL tobramycin (Sigma #T4014), 10 µg/mL Cell Prime r-transferrin AF (Millipore #9701)+10 µg/mL Nucellin (Lilly human recombinant insulin)), plated at $4\times10^4$ cells/well in 96-well plates, and incubated overnight at 37° C. under 5% (v/v) $CO_2$. The medium is aspirated and 500 µg/mL sodium heparin (Sigma, #H3393) are added in basal medium at 100 µL/well; the cells are then incubated for 1 hour at 37° C. The wells are aspirated, washed once with 100 µL basal medium, and ECFC are added as follows: ECFC (EndGenitor Technologies, Inc., Indianapolis, Ind. #EGT-ECFC100506) are dissociated, washed in basal medium, resuspended in basal medium, and added at $4\times10^3$ cells/well on top of ADSC in 96-well plates. After 4 hours incubation at 37° C., HGF and antibodies are diluted in the cell culture medium and added to separate wells at the following final concentrations: HGF:100 ng/mL; antibodies: 10 µg/mL. The HGF antibody (R&D Systems #AB-294-NA) is also added at 10 µg/mL final concentration. The cells are incubated for an additional 4 days at 37° C. The wells are aspirated, and 100 µL/well of 1% paraformaldehyde are added, followed by incubation for 20-30 min. Cells are washed three times with PBS-BSA (0.1% BSA, Invitrogen #15260-037) and treated with 50 µL of 1 µg/mL anti-human CD31 antibody (R&D Systems, #AF806) for 1 hour at 37° C. or overnight at 4° C. Cells are washed twice with PBS-BSA and treated with 50 µL of 4 µg/mL anti-sheep IgG AlexaFluor488 conjugate (Invitrogen, #A11015) for 1 hour at room temperature. Cells are washed twice with PBS-BSA and stained with 100 µL of Hoechst3342 dye and read on a Cellomics ArrayScan (Thermo Fisher Scientific, Waltham, Mass.). vHCS View Version 1.4.6 software is used to determine total tube areas, which are used to evaluate the effect of the various antibodies and HGF on stimulation of angiogenesis.

The results are shown in Table 20.

TABLE 20

Effect of C8- Antibodies on Tube Formation in ECFC Cells Total Tube Area

|  | Basal Medium | hIgG4 | C8-H241 | C8-6 | mIgG1 | 5D5 | HGF Ab | HGF |
|---|---|---|---|---|---|---|---|---|
| Avg. | 67753.3 | 90134.3 | 22979.7 | 65224.0 | 125538.3 | 147237.3 | 22824.3 | 212104.7 |
| Std. Dev. | 24221.6 | 17741.1 | 604.9 | 18275.9 | 34702.4 | 18748.1 | 6586.0 | 16588.5 |

The results demonstrate that C8-H241 and C8-6 do not stimulate tube formation compared to the medium or their corresponding isotype control antibodies, whereas HGF and agonist Mab 5D5 significantly stimulate tube formation.

EXAMPLE 18

Inhibition of HGF-Independent and HGF-Dependent Tumor Cell Growth in Xenograft Models The inhibition of HGF-independent and HGF-dependent tumor cell growth by c-Met antibodies of the present invention is examined in in vivo assays employing MKN45 cell and U87MG (human glioblastoma) cell mouse xenograft models, respectively. MKN45 cells constitutively express high levels of c-Met and c-Met phosphorylation in the absence of HGF. U87MG cells secrete HGF in an autocrine manner, and are HGF-responsive.

MKN45 cells (Japan Health Sciences Foundation, Health Science Research Resource, #JCRB0254) are expanded in culture as described in Example 8, trypsinized to single cells, harvested, and resuspended in PBS. Two million MKN45 cells in PBS are injected subcutaneously into the rear flank of athymic nude mice (Harlan, Indianapolis, Ind.). c-Met antibodies and corresponding IgG2 and IgG4 antibodies are diluted in PBS, pH 7.2, and administered on a weekly basis by intravenous injection starting from 3 or 7 days after tumor cell implantation at 1, 5, or 20 mg/mL Inhibition of tumor cell growth is determined by three dimensional caliper measurement of tumor volumes twice weekly during the course of treatment. Body weight is measured as a general measurement of toxicity.

U87MG cells (ATCC, #HTB-14) are grown in MEM (Invitrogen, #11095) at 37'C, expanded in culture, trypsinized to single cells, harvested, and resuspended in PBS (Invitrogen, #14190). Five million cells are injected subcutaneously into the rear flank of athymic nude mice (Harlan, Indianapolis, Ind.). c-Met antibodies are diluted in PBS, and administered on a weekly basis by intravenous injection at the doses indicated in Table 22 starting 7 days after tumor cell implantation. Control IgG4 antibody is administered at 10 mg/kg Inhibition of tumor cell growth is determined by three dimensional caliper measurement of tumor volumes twice weekly during the course of treatment. Body weight is measured as a general measurement of toxicity.

The anti-tumor efficacy of four antibodies, D11-8B8, C8-H241, C8-6, and C8-Co-16 in the MKN45 cell xenograft model is summarized in Table 21. "Maximum % Inhibition" represents the percent inhibition of tumor growth compared to treatment with corresponding control antibody (0% inhibition).

When dosed at 5 mg/kg or 20 mg/kg, all four c-Met antibodies produce significant inhibition of MKN45 tumor cell growth as compared to their corresponding IgG isotype controls.

TABLE 21

Effect of C8- and D11-Antibodies
On HGF-Independent MKN45 Tumor Growth In Vivo

| Antibody | Dose level (mg/kg) | Maximum % Inhibition | p value |
|---|---|---|---|
| D11-8B8 | 5 | 53 | p < 0.05 |
|  | 20 | 56 | p < 0.01 |
| C8-H241 | 1 | 39 | NS |
|  | 5 | 63 | p < 0.01 |
|  | 20 | 51 | p < 0.05 |
| C8-6 | 1 | 60 | p < 0.001 |
|  | 5 | 59 | p < 0.01 |
|  | 20 | 73 | p < 0.001 |
| C8-Co-16 | 1 | 36 | NS |
|  | 5 | 60 | p < 0.001 |
|  | 20 | 85 | p < 0.001 |

A dose-dependent inhibition of tumor cell growth by C8-H241 is also observed in the HGF-dependent U87MG cell xenograft model, as summarized in Table 22. "Maximum % Inhibition" represents the percent inhibition of tumor growth compared to treatment with corresponding IgG4 control antibody (0% inhibition).

TABLE 22

Effect of C8-H241 Antibody
On HGF-Depdendent U87MG Tumor Growth In Vivo

| Antibody | Dose level (mg/kg) | Maximum % Inhibition | p value |
|---|---|---|---|
| C8-H241 | 0.1 | 45.2 | NS |
| C8-H241 | 0.3 | 86.8 | p < 0.001 |
| C8-H241 | 1 | 91.9 | p < 0.001 |
| C8-H241 | 3 | 91 | p < 0.001 |
| C8-H241 | 10 | 94.8 | p < 0.001 |

At 5 and 20 mg/kg, C8-H241 antibody also inhibits H441 non-small cell lung cancer xenograft tumor growth 58% and 60%, respectively. H441 cells exhibit a high level of c-Met expression and constitutive phosphorylation of c-Met, but are still responsive to HGF.

EXAMPLE 19

Antibody Reduction of Total and Phosphorylated c-Met in MKN45 Xenograft Tumors

The in vivo activity of c-Met antibody C8-H241 on total c-Met and phosphorylated c-Met in mice bearing MKN45 (HGF-independent) xenograft tumors is investigated in this example. A dose-dependent reduction of both total c-Met and phosphorylated c-Met (at tyrosine 1349) is observed 24 hours after antibody administration.

MKN45 cells are expanded in culture as described in Example 8, trypsinized, and harvested. Two million MKN45 cells in PBS are injected subcutaneously into the rear flank of athymic nude mice (Harlan, Indianapolis, Ind.). c-Met antibody C8-H241 is diluted in PBS, pH 7.2, and administered by intravenous injection eight days after tumor cell implantation at 2.5, 5, 10, 20, and 40 mg/kg. Control antibody hIgG4 is administered at 40 mg/kg. After 24 hours of treatment, tumors are removed, flash frozen, stored temporarily at −80° C., and lysed in lysis buffer (5 mM ethylenediaminetetraacetic acid (EDTA), 5 mM ethyleneglycol-bis(b-aminoethyl)-N,N,N', N'-tetracetic acid (EGTA), 50 mM HEPES, 20 mM sodium pyrophosphate (ThermoFisherScientific, #S390-500), 150 mM NaCl, 20 mM NaF, 1% (v/v) octylphenoxy polyethoxy ethanol (TRITON®-X 100), complete protease inhibitor, EDTA free (Roche, Basel, Switzerland, #1836153) phosphatase inhibitor cocktail I (Sigma #P2850), and phosphatase inhibitor cocktail II (Sigma #P5726)).

Total c-Met ELISA

For the total c-Met ELISA, a c-Met capture antibody is diluted in Bup H coating buffer (Thermo Fisher Scientific, Waltham, Mass., #28382) to 2 µg/mL. 100 µL of the diluted antibody is added per well to ELISA plates (ThermoFisher-Scientific, Waltham, Mass. #439-454), and the plates are incubated overnight at 4° C. The wells are aspirated, washed twice with TBS-T, and then blocked with 200 µL of blocking buffer (TBS-T plus 2% (w/v) BSA) for 1 hour at room temperature. The plates are washed twice with TBS-T. Next, dilutions of tumor lysates or c-Met extracellular domain (amino acids 25-932 of SEQ ID NO:75) are added, and the plates are incubated overnight at 4° C. The plates are then washed three times with TBS-T. 100 µL of 0.5 µg/mL of biotinylated Mab 5D5 (as second c-Met antibody that binds a different c-Met epitope from the capture antibody) diluted in blocking buffer are then added to each well, and the plates are incubated for 2 hours at room temperature. Next, the plates are washed three times with TBS-T. 100 µL of 1/10,000 diluted peroxidase-conjugated streptavidin (Jackson ImmunoResearch Laboratories, West Grove, Pa., #016-030-084) in blocking buffer are then added, and the mixture is incubated for 1 hour at room temperature. The plates are then washed three times with TBS-T. 100 µL of 3,3',5,5'-tetramethylbenzidine solution (BioFX, #TMBW-1000-01) are added to each well, followed by the addition of 100 µL stop solution (BioFX, #LSTP-1000-01). The plates are read at 450 nm using a SpectraMax 250 plate reader (Molecular Devices, Sunnyvale, Calif.) with SOFTmax Pro 3.1.2 software (Molecular Devices).

Phosphorylated c-Met ELISA

For the phospho-c-Met ELISA, a c-Met capture antibody is diluted in Bup H coating buffer (Thermo Fisher Scientific, Waltham, Mass., #28382) to 2 µg/mL. 100 µL of the diluted antibody are added per well to ELISA plates (ThermoFisher-Scientific, Waltham, Mass. #439-454), and the plates are incubated overnight at 4° C. The wells are aspirated, washed twice with TBS-T, and then blocked with 200 µL of blocking buffer (TBS-T plus 2% (w/v) BSA) for 1 hour at room temperature. The plates are washed twice with TBS-T. Next, MKN45 cell lysates are added, and the plates are incubated overnight at room temperature. The plates are then washed three times with TBS-T. 100 µL of 0.5 µg/mL anti-pY1349 c-Met antibody (Cell Signaling Technology, Danvers, Mass., #3121) diluted in blocking buffer are then added to each well, and the plates are incubated for 2 hours at room temperature. Next, the plates are washed three times with TBS-T. 100 µL of 1/10,000 diluted peroxidase conjugated anti-rabbit IgG (Jackson ImmunoResearch Laboratories, West Grove, Pa., #111-035-144) in blocking buffer are then added, and the mixture is incubated for 1 hour at room temperature. The plates are then washed three times with TBS-T. 100 µL of 3,3',5,5'-tetramethylbenzidine solution (BioFX, #TMBW-1000-01) are added to each well, followed by the addition of 100 µL stop solution (BioFX, #LSTP-1000-01). The plates are read at 450 nm using a SpectraMax 250 plate reader (Molecular Devices, Sunnyvale, Calif.) with SOFTmax Pro 3.1.2 software (Molecular Devices).

The results are shown in Table 23.

The data demonstrate that in vivo treatment of MKN45 xenograft tumors with Mab C8-H241 for 24 hours maximally reduces total c-Met by approximately 43%, and phosphorylated c-Met by approximately 73%, under these conditions.

TABLE 23

Reduction of Total and Phosphorylated c-Met in MKN45 Xenograft Tumors After 24 Hour Treatment with c-Met antibody C8-H241 In Vivo

| % Inhibition | PBS | C8-H241 | | | | | hIgG4 |
| --- | --- | --- | --- | --- | --- | --- | --- |
| | | 2.5 mpk | 5 mpk | 10 mpk | 20 mpk | 40 mpk | 40 mpk |
| Reduction of Total c-Met | | | | | | | |
| average % inhibition | −88.51 | −8.43 | 4.26 | 25.07 | 42.85 | 30.62 | 0.00 |
| st. dev. % inhibition | 62.63 | −8.43 | 36.84 | 26.88 | 17.67 | 35.95 | 41.23 |
| Reduction of Phosphorylated c-Met | | | | | | | |
| average % inhibition | 12.16 | 22.89 | 17.56 | 53.21 | 67.04 | 73.42 | 0.00 |
| st. dev. % inhibition | 23.89 | 22.89 | 37.05 | 9.90 | 6.58 | 7.04 | 48.81 | mpk: mg/kg

Amino Acid and Nucleotide Sequences

Light Chain Variable Region Amino Acid Sequences

D11-S17Y
(SEQ ID NO: 1)
EIVLTQSPGTLSLSPGERATLSCSVSSSISSTNLHWYQQKPGQAPRLLIY
GTSYLASGIPDRFSGSGSGTDFTLTISRLEPEDFAVYYCQQWSSYPYSFG
QGTKLEIK

D11-8B8
(SEQ ID NO: 2)
EIVLTQSPGTLSLSPGERATLSCSVSSSISSTNLHWYQQKPGQAPRLLIY
GTSYLASGIPDRFSGSGSGTDFTLTISRLEPEDFAVYYCQQWSSYPYSFG
QGTKLEIK

D11-C27G3
(SEQ ID NO: 3)
EIVLTQSPGTLSLSPGERATLSCSVSSSISSTNLHWYQQKPGQAPRLLIY
GTSRLRSGIPDRFSGSGSGTDFTLTISRLEPEDFAVYYCQQWSSYPYSFG
QGTKLEIK

C8-6
(SEQ ID NO: 4)
DIQMTQSPSSLSASVGDRVTITCSVSSSVSSIYLHWYQQKPGKAPKLLIY
STSNLASGVPSRFSGSGSGTDFTLTISSLQPEDFATYYCIQYSGYPLTFG
GGTKVEIK

C8-H241
(SEQ ID NO: 5)
DIQMTQSPSSLSASVGDRVTITCSVSSSVSSIYLHWYQQKPGKAPKLLIY
STSNLASGVPSRFSGSGSGTDFTLTISSLQPEDFATYYCQVYSGYPLTFG
GGTKVEIK

C8-co-16
(SEQ ID NO: 6)
DIQMTQSPSSLSASVGDRVTITCSVSSSVRSIYLHWYQQKPGKAPKLLIY
STSNLASGVPSRFSGSGSGTDFTLTISSLQPEDFATYYCQVYRGYPLTFG
GGTKVEIK

Light Chain Variable Region Nucleic Acid Sequences

D11-S17Y
(SEQ ID NO: 7)
GAAATTGTGTTGACGCAGTCTCCAGGCACCCTGTCTTTGTCTCCAGGGGA
AAGAGCCACCCTCTCCTGCAGTGTCAGCTCAAGTATAAGTTCCACCAACT
TACACTGGTACCAGCAGAAACCTGGCCAGGCTCCCAGGCTCCTCATCTAT
GGCACATCCTATCTGGCTTCTGGCATCCCAGACAGGTTCAGTGGCAGTGG
GTCTGGGACAGACTTCACTCTCACCATCAGCAGACTGGAGCCTGAAGATT
TTGCAGTGTATTACTGTCAACAGTGGAGTAGTTACCCGTACAGTTTCGGC
CAAGGGACCAAGTTGGAGATCAAA

D11-8B8
(SEQ ID NO: 8)
GAAATTGTGTTGACGCAGTCTCCAGGCACCCTGTCTTTGTCTCCAGGGGA
AAGAGCCACCCTCTCCTGCAGTGTCAGCTCAAGTATAAGTTCCACCAACT
TACACTGGTACCAGCAGAAACCTGGCCAGGCTCCCAGGCTCCTCATCTAT
GGCACATCCTACCTGGCTTCTGGCATCCCAGACAGGTTCAGTGGCAGTGG
GTCTGGGACAGACTTCACTCTCACCATCAGCAGACTGGAGCCTGAAGATT
TTGCAGTGTATTACTGTCAACAGTGGAGTAGTTACCCGTACAGTTTCGGC
CAAGGGACCAAGTTGGAGATCAAA

D11-C27G3
(SEQ ID NO: 9)
GAAATTGTGTTGACGCAGTCTCCAGGCACCCTGTCTTTGTCTCCAGGGGA
AAGAGCCACCCTCTCCTGCAGTGTCAGCTCAAGTATAAGTTCCACCAACT
TACACTGGTACCAGCAGAAACCTGGCCAGGCTCCCAGGCTCCTCATCTAT
GGCACATCCAGACTGAGATCTGGCATCCCAGACAGGTTCAGTGGCAGTGG
GTCTGGGACAGACTTCACTCTCACCATCAGCAGACTGGAGCCTGAAGATT
TTGCAGTGTATTACTGTCAACAGTGGAGTAGTTACCCGTACAGTTTCGGC
CAAGGGACCAAGTTGGAGATCAAA

C8-6
(SEQ ID NO: 10)
GACATCCAGATGACCCAGTCTCCATCCTCCCTGTCTGCATCTGTAGGAGA
CAGAGTCACCATCACTTGCAGTGTCAGCTCAAGTGTAAGTTCCATTTACT
TGCACTGGTATCAGCAGAAACCAGGGAAAGCCCCTAAGCTCCTGATCTAT

```
AGCACATCCAACTTGGCTTCTGGAGTCCCATCAAGGTTCAGTGGCAGTGG

ATCTGGGACAGATTTCACTCTCACCATCAGCAGTCTGCAACCTGAAGATT

TTGCAACTTACTACTGTATTCAGTACAGTGGTTACCCGCTCACGTTCGGC

GGAGGGACCAAGGTGGAGATCAAA
```

C8-H241
(SEQ ID NO: 11)
```
GACATCCAGATGACCCAGTCTCCATCCTCCCTGTCTGCATCTGTAGGAGA

CAGAGTCACCATCACTTGCAGTGTCAGCTCAAGTGTAAGTTCCATTTACT

TGCACTGGTATCAGCAGAAACCAGGGAAAGCCCCTAAGCTCCTGATCTAT

AGCACATCCAACTTGGCTTCTGGAGTCCCATCAAGGTTCAGTGGCAGTGG

ATCTGGGACAGATTTCACTCTCACCATCAGCAGTCTGCAACCTGAAGATT

TTGCAACTTACTACTGTCAGGTGTACAGTGGTTACCCGCTCACGTTCGGC

GGAGGGACCAAGGTGGAGATCAAA
```

C8-co-16
(SEQ ID NO: 12)
```
GACATCCAGATGACCCAGTCTCCATCCTCCCTGTCTGCATCTGTAGGAGA

CAGAGTCACCATCACTTGCAGTGTCAGCTCAAGTGTACGTTCCATTTACT

TGCACTGGTATCAGCAGAAACCAGGGAAAGCCCCTAAGCTCCTGATCTAT

AGCACATCCAACTTGGCTTCTGGAGTCCCATCAAGGTTCAGTGGCAGTGG

ATCTGGGACAGATTTCACTCTCACCATCAGCAGTCTGCAACCTGAAGATT

TTGCAACTTACTACTGTCAGGTGTACAGGGGTTACCCGCTCACGTTCGGC

GGAGGGACCAAGGTGGAGATCAAA
```

Heavy Chain Variable Region Amino Acid Sequences

D11-S17Y
(SEQ ID NO: 13)
QVQLVQSGAEVKKPGSSVKVSCKASGYTFTSRYIHWVRQAPGQGLEWMGW
IYPVTGDTYYNEKFKGRVTITADKSTSTAYMELSSLRSEDTAVYYCARGY
GAFYYWGQGTLVTVS

D11-8B8
(SEQ ID NO: 14)
QVQLVQSGAEVKKPGSSVKVSCKASGYTFTSRYIHWVRQAPGQGLEWMGW
IYPVTGDTYYIEKFKGRVTITADKSTSTAYMELSSLRSEDTAVYYCARGY
GAFFYWGQGTLVTVS

D11-C27G3
(SEQ ID NO: 15)
QVQLVQSGAEVKKPGSSVKVSCKASGYTFTSRYIHWVRQAPGQGLEWMGW
IYPVTGDTYYREPFKGRVTITADKSTSTAYMELSSLRSEDTAVYYCARGY
GAFYYWGQGTLVTVS

C8-6
(SEQ ID NO: 16)
QVQLVQSGAEVKKPGASVKVSCKASGYTFTDYYMHWVRQAPGQGLEWMGR
VNPNRGGTTYNQKFEGRVTMTTDTSTSTAYMELRSLRSDDTAVYYCARTN
WLDYWGQGTTVTVS

C8-H241
(SEQ ID NO: 17)
QVQLVQSGAEVKKPGASVKVSCKASGYTFTDYYMHWVRQAPGQGLEWMGR
VNPNRRGTTYNQKFEGRVTMTTDTSTSTAYMELRSLRSDDTAVYYCARAN
WLDYWGQGTTVTVS

C8-co-16
(SEQ ID NO: 18)
QVQLVQSGAEVKKPGASVKVSCKASGYTFTDYYMHWVRQAPGQGLEWMGR
VNPYRGSTTYNQKFEGRVTMTTDTSTSTAYMELRSLRSDDTAVYYCARAN
ILDYWGQGTTVTVS

Heavy Chain Variable Region Nucleic Acid Sequences

D11-S17Y
(SEQ ID NO: 19)
```
CAGGTGCAGCTGGTGCAGTCTGGGGCTGAGGTGAAGAAGCCTGGGTCCTC

GGTGAAGGTCTCCTGCAAGGCTTCTGGCTACACCTTCACAAGTAGGTATA

TACACTGGGTGCGACAGGCCCCTGGACAAGGGCTTGAGTGGATGGGATGG

ATTTATCCTGTAACTGGTGATACTTACTACAACGAGAAGTTCAAGGGCAG

AGTCACGATTACCGCGGACAAATCCACGAGCACAGCCTACATGGAGCTGA

GCAGCCTGAGATCTGAGGACACGGCCGTGTATTACTGTGCGAGAGGCTAC

GGAGCTTTTTACTACTGGGGCCAGGGCACCCTGGTCACCGTCTCC
```

D11-8B8
(SEQ ID NO: 20)
```
CAGGTGCAGCTGGTGCAGTCTGGGGCTGAGGTGAAGAAGCCTGGGTCCTC

GGTGAAGGTCTCCTGCAAGGCTTCTGGCTACACCTTCACAAGTAGGTATA

TACACTGGGTGCGACAGGCCCCTGGACAAGGGCTTGAGTGGATGGGATGG

ATTTATCCTGTAACTGGTGATACTTACTACATCGAGAAGTTCAAGGGCAG

AGTCACGATTACCGCGGACAAATCCACGAGCACAGCCTACATGGAGCTGA

GCAGCCTGAGATCTGAGGACACGGCCGTGTATTACTGTGCGAGAGGCTAT

GGTGCTTTTTTCTACTGGGGCCAGGGCACCCTGGTCACCGTCTCC
```

D11-C27G3
(SEQ ID NO: 21)
```
CAGGTGCAGCTGGTGCAGTCTGGGGCTGAGGTGAAGAAGCCTGGGTCCTC

GGTGAAGGTCTCCTGCAAGGCTTCTGGCTACACCTTCACAAGTAGGTATA

TACACTGGGTGCGACAGGCCCCTGGACAAGGGCTTGAGTGGATGGGATGG

ATTTATCCTGTAACTGGTGATACTTACTACAGAGAGCCTTTCAAGGGCAG

AGTCACGATTACCGCGGACAAATCCACGAGCACAGCCTACATGGAGCTGA

GCAGCCTGAGATCTGAGGACACGGCCGTGTATTACTGTGCGAGAGGCTAT

GGGGCTTTTTACTACTGGGGCCAGGGCACCCTGGTCACCGTCTCC
```

C8-6
(SEQ ID NO: 22)
```
CAGGTTCAGCTGGTGCAGTCTGGTGCTGAGGTGAAGAAGCCTGGTGCCTC

AGTGAAGGTCTCCTGCAAGGCTTCTGGTTACACCTTTACCGACTACTACA

TGCACTGGGTGCGTCAGGCCCCTGGTCAAGGTCTTGAGTGGATGGGTCGT

GTTAATCCTAACCGGGGTGGTACTACCTACAACCAGAAATTCGAGGGCCG

TGTCACCATGACCACAGACACATCCACGAGCACAGCCTACATGGAGCTGC

GTAGCCTGCGTTCTGACGACACGGCCGTGTATTACTGTGCGCGTACGAAC

TGGCTTGACTACTGGGGCCAGGGCACCACCGTCACCGTCTCC
```

C8-H241
(SEQ ID NO: 23)
CAGGTTCAGCTGGTGCAGTCTGGTGCTGAGGTGAAGAAGCCTGGTGCCTC

AGTGAAGGTCTCCTGCAAGGCTTCTGGTTACACCTTTACCGACTACTACA

TGCACTGGGTGCGTCAGGCCCCTGGTCAAGGTCTTGAGTGGATGGGTCGT

GTTAATCCTAACCGGAGGGGTACTACCTACAACCAGAAATTCGAGGGCCG

TGTCACCATGACCACAGACACATCCACGAGCACAGCCTACATGGAGCTGC

GTAGCCTGCGTTCTGACGACACGGCCGTGTATTACTGTGCGCGTGCGAAC

TGGCTTGACTACTGGGGCCAGGGCACCACCGTCACCGTCTCC

C8-co-16
(SEQ ID NO: 24)
CAGGTTCAGCTGGTGCAGTCTGGTGCTGAGGTGAAGAAGCCTGGTGCCTC

AGTGAAGGTCTCCTGCAAGGCTTCTGGTTACACATTCACTGACTACTACA

TGCACTGGGTGCGTCAGGCCCCTGGTCAAGGTCTTGAGTGGATGGGTCGT

GTTAATCCTTATCGGGGTAGTACTACCTACAACCAGAAATTCGAGGGCCG

TGTCACCATGACCACAGACACATCCACGAGCACAGCCTACATGGAGCTGC

GTAGCCTGCGTTCTGACGACACGGCCGTGTATTACTGTGCGCGTGCGAAC

ATTCTTGACTACTGGGGCCAGGGCACCACCGTCACCGTCTCC

Complete Light Chain Amino Acid Sequences

D11-S17Y kappa
(SEQ ID NO: 25)
EIVLTQSPGTLSLSPGERATLSCSVSSSISSTNLHWYQQKPGQAPRLLIY

GTSYLASGIPDRFSGSGSGTDFTLTISRLEPEDFAVYYCQQWSSYPYSFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

D11-8B8 kappa
(SEQ ID NO: 26)
EIVLTQSPGTLSLSPGERATLSCSVSSSISSTNLHWYQQKPGQAPRLLIY

GTSYLASGIPDRFSGSGSGTDFTLTISRLEPEDFAVYYCQQWSSYPYSFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

D11-C27G3 kappa
(SEQ ID NO: 27)
EIVLTQSPGTLSLSPGERATLSCSVSSSISSTNLHWYQQKPGQAPRLLIY

GTSRLRSGIPDRFSGSGSGTDFTLTISRLEPEDFAVYYCQQWSSYPYSFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

C8-6 kappa
(SEQ ID NO: 28)
DIQMTQSPSSLSASVGDRVTITCSVSSSVSSIYLHWYQQKPGKAPKLLIY

STSNLASGVPSRFSGSGSGTDFTLTISSLQPEDFATYYCIQYSGYPLTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

C8-H241 kappa
(SEQ ID NO: 29)
DIQMTQSPSSLSASVGDRVTITCSVSSSVSSIYLHWYQQKPGKAPKLLIY

STSNLASGVPSRFSGSGSGTDFTLTISSLQPEDFATYYCQVYSGYPLTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

C8-co-16 kappa
(SEQ ID NO: 30)
DIQMTQSPSSLSASVGDRVTITCSVSSSVRSIYLHWYQQKPGKAPKLLIY

STSNLASGVPSRFSGSGSGTDFTLTISSLQPEDFATYYCQVYRGYPLTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Complete Light Chain Nucleic Acid Sequences

D11-S17Y IgG2 LC
(SEQ ID NO: 31)
GAAATTGTGTTGACGCAGTCTCCAGGCACCCTGTCTTTGTCTCCAGGGGA

AAGAGCCACCCTCTCCTGCAGTGTCAGCTCAAGTATAAGTTCCACCAACT

TACACTGGTACCAGCAGAAACCTGGCCAGGCTCCCAGGCTCCTCATCTAT

GGCACATCCTACCTGGCTTCTGGCATCCCAGACAGGTTCAGTGGCAGTGG

GTCTGGGACAGACTTCACTCTCACCATCAGCAGACTGGAGCCTGAAGATT

TTGCAGTGTATTACTGTCAACAGTGGAGTAGTTACCCGTACAGTTTCGGC

CAAGGGACCAAGTTGGAGATCAAACGAACTGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGC

D11-8B8 IgG2 LC
(SEQ ID NO: 32)
GAAATTGTGTTGACGCAGTCTCCAGGCACCCTGTCTTTGTCTCCAGGGGA

AAGAGCCACCCTCTCCTGCAGTGTCAGCTCAAGTATAAGTTCCACCAACT

TACACTGGTACCAGCAGAAACCTGGCCAGGCTCCCAGGCTCCTCATCTAT

GGCACATCCTACCTGGCTTCTGGCATCCCAGACAGGTTCAGTGGCAGTGG

GTCTGGGACAGACTTCACTCTCACCATCAGCAGACTGGAGCCTGAAGATT

TTGCAGTGTATTACTGTCAACAGTGGAGTAGTTACCCGTACAGTTTCGGC

CAAGGGACCAAGTTGGAGATCAAACGAACTGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

-continued
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGC D11-C27G3 IgG2 LC
(SEQ ID NO: 33)
GAAATTGTGTTGACGCAGTCTCCAGGCACCCTGTCTTTGTCTCCAGGGGA
AAGAGCCACCCTCTCCTGCAGTGTCAGCTCAAGTATAAGTTCCACCAACT
TACACTGGTACCAGCAGAAACCTGGCCAGGCTCCCAGGCTCCTCATCTAT
GGCACATCCAGACTGAGATCTGGCATCCCAGACAGGTTCAGTGGCAGTGG
GTCTGGGACAGACTTCACTCTCACCATCAGCAGACTGGAGCCTGAAGATT
TTGCAGTGTATTACTGTCAACAGTGGAGTAGTTACCCGTACAGTTTCGGC
CAAGGGACCAAGTTGGAGATCAAACGAACTGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGC C8-6 IgG4 LC
(SEQ ID NO: 34)
GACATCCAGATGACCCAGTCTCCATCCTCCCTGTCTGCATCTGTAGGAGA
CAGAGTCACCATCACTTGCAGTGTCAGCTCAAGTGTAAGTTCCATTTACT
TGCACTGGTATCAGCAGAAACCAGGGAAAGCCCCTAAGCTCCTGATCTAT
AGCACATCCAACTTGGCTTCTGGAGTCCCATCAAGGTTCAGTGGCAGTGG
ATCTGGGACAGATTTCACTCTCACCATCAGCAGTCTGCAACCTGAAGATT
TTGCAACTTACTACTGTATTCAGTACAGTGGTTACCCGCTCACGTTCGGC
GGAGGGACCAAGGTGGAGATCAAACGAACTGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGC C8-H241 IgG4 LC
(SEQ ID NO: 35)
GACATCCAGATGACCCAGTCTCCATCCTCCCTGTCTGCATCTGTAGGAGA
CAGAGTCACCATCACTTGCAGTGTCAGCTCAAGTGTATCCTCCATTTACT
TGCACTGGTATCAGCAGAAACCAGGGAAAGCCCCTAAGCTCCTGATCTAT
AGCACATCCAACTTGGCTTCTGGAGTCCCATCAAGGTTCAGTGGCAGTGG
ATCTGGGACAGATTTCACTCTCACCATCAGCAGTCTGCAACCTGAAGATT
TTGCAACTTACTACTGTCAAGTCTACAGTGGTTACCCGCTCACGTTCGGC
GGAGGGACCAAGGTGGAGATCAAACGAACTGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGC C8-co16 IgG4 LC
(SEQ ID NO: 36)
GACATCCAGATGACCCAGTCTCCATCCTCCCTGTCTGCATCTGTAGGAGA
CAGAGTCACCATCACTTGCAGTGTCAGCTCAAGTGTACGTTCCATTTACT
TGCACTGGTATCAGCAGAAACCAGGGAAAGCCCCTAAGCTCCTGATCTAT
AGCACATCCAACTTGGCTTCTGGAGTCCCATCAAGGTTCAGTGGCAGTGG
ATCTGGGACAGATTTCACTCTCACCATCAGCAGTCTGCAACCTGAAGATT
TTGCAACTTACTACTGTCAGGTGTACAGGGGTTACCCGCTCACGTTCGGC
GGAGGGACCAAGGTGGAGATCAAACGAACTGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGC Complete Heavy Chain Amino Acid Sequences D11-S17Y IgG2
(SEQ ID NO: 37)
QVQLVQSGAEVKKPGSSVKVSCKASGYTFTSRYIHWVRQAPGQGLEWMGW
IYPVTGDTYYNEKFKGRVTITADKSTSTAYMELSSLRSEDTAVYYCARGY
GAFYYWGQGTLVTVSSASTKGPSVFPLAPCSRSTSESTAALGCLVKDYFP
EPVTVSWNSGALTSGVHTFPAVLQSSGLYSLSSVVTVPSSNFGTQTYTCN
VDHKPSNTKVDKTVERKCCVECPPCPAPPVAGPSVFLFPPKPKDTLMISR
TPEVTCVVVDVSHEDPEVQFNWYVDGMEVHNAKTKPREEQFNSTFRVVSV
LTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFF
LYSKLTVDKSRWQQGNVFSCSVMHEALHNHYTQKSLSLSPG D11-8B8 IgG2
(SEQ ID NO: 38)
QVQLVQSGAEVKKPGSSVKVSCKASGYTFTSRYIHWVRQAPGQGLEWMGW
IYPVTGDTYYIEKFKGRVTITADKSTSTAYMELSSLRSEDTAVYYCARGY
GAFFYWGQGTLVTVSSASTKGPSVFPLAPCSRSTSESTAALGCLVKDYFP
EPVTVSWNSGALTSGVHTFPAVLQSSGLYSLSSVVTVPSSNFGTQTYTCN
VDHKPSNTKVDKTVERKCCVECPPCPAPPVAGPSVFLFPPKPKDTLMISR
TPEVTCVVVDVSHEDPEVQFNWYVDGMEVHNAKTKPREEQFNSTFRVVSV
LTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFF
LYSKLTVDKSRWQQGNVFSCSVMHEALHNHYTQKSLSLSPG -continued D11-C27G3 IgG2
(SEQ ID NO: 39)
QVQLVQSGAEVKKPGSSVKVSCKASGYTFTSRYIHWVRQAPGQGLEWMGW
IYPVTGDTYYREPFKGRVTITADKSTSTAYMELSSLRSEDTAVYYCARGY
GAFYYWGQGTLVTVSSASTKGPSVFPLAPCSRSTSESTAALGCLVKDYFP
EPVTVSWNSGALTSGVHTFPAVLQSSGLYSLSSVVTVPSSNFGTQTYTCN
VDHKPSNTKVDKTVERKCCVECPPCPAPPVAGPSVFLFPPKPKDTLMISR
TPEVTCVVVDVSHEDPEVQFNWYVDGMEVHNAKTKPREEQFNSTFRVVSV
LTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFF
LYSKLTVDKSRWQQGNVFSCSVMHEALHNHYTQKSLSLSPG C8-6 IgG2
(SEQ ID NO: 40)
QVQLVQSGAEVKKPGASVKVSCKASGYTFTDYYMHWVRQAPGQGLEWMGR
VNPNRGGTTYNQKFEGRVTMTTDTSTSTAYMELRSLRSDDTAVYYCARTN
WLDYWGQGTTVTVSSASTKGPSVFPLAPCSRSTSESTAALGCLVKDYFPE
PVTVSWNSGALTSGVHTFPAVLQSSGLYSLSSVVTVPSSNFGTQTYTCNV
DHKPSNTKVDKTVERKCCVECPPCPAPPVAGPSVFLFPPKPKDTLMISRT
PEVTCVVVDVSHEDPEVQFNWYVDGMEVHNAKTKPREEQFNSTFRVVSVL
TVVHQDWLNGKEYKCKVSNKGLPAPIEKTISKTKGQPREPQVYTLPPSRE
EMTKNQVSLTCLVKGFYPSDIAVEWESNGQPENNYKTTPPMLDSDGSFFL
YSKLTVDKSRWQQGNVFSCSVMHEALHNHYTQKSLSLSPG C8-H241 IgG2
(SEQ ID NO: 41)
QVQLVQSGAEVKKPGASVKVSCKASGYTFTDYYMHWVRQAPGQGLEWMGR
VNPNRRGTTYNQKFEGRVTMTTDTSTSTAYMELRSLRSDDTAVYYCARAN
WLDYWGQGTTVTVSSASTKGPSVFPLAPCSRSTSESTAALGCLVKDYFPE
PVTVSWNSGALTSGVHTFPAVLQSSGLYSLSSVVTVPSSNFGTQTYTCNV
DHKPSNTKVDKTVERKCCVECPPCPAPPVAGPSVFLFPPKPKDTLMISRT
PEVTCVVVDVSHEDPEVQFNWYVDGMEVHNAKTKPREEQFNSTFRVVSVL
TVVHQDWLNGKEYKCKVSNKGLPAPIEKTISKTKGQPREPQVYTLPPSRE
EMTKNQVSLTCLVKGFYPSDIAVEWESNGQPENNYKTTPPMLDSDGSFFL
YSKLTVDKSRWQQGNVFSCSVMHEALHNHYTQKSLSLSPG C8-co-16 IgG2
(SEQ ID NO: 42)
QVQLVQSGAEVKKPGASVKVSCKASGYTFTDYYMHWVRQAPGQGLEWMGR
VNPYRGSTTYNQKFEGRVTMTTDTSTSTAYMELRSLRSDDTAVYYCARAN
ILDYWGQGTTVTVSSASTKGPSVFPLAPCSRSTSESTAALGCLVKDYFPE
PVTVSWNSGALTSGVHTFPAVLQSSGLYSLSSVVTVPSSNFGTQTYTCNV
DHKPSNTKVDKTVERKCCVECPPCPAPPVAGPSVFLFPPKPKDTLMISRT
PEVTCVVVDVSHEDPEVQFNWYVDGMEVHNAKTKPREEQFNSTFRVVSVL
TVVHQDWLNGKEYKCKVSNKGLPAPIEKTISKTKGQPREPQVYTLPPSRE
EMTKNQVSLTCLVKGFYPSDIAVEWESNGQPENNYKTTPPMLDSDGSFFL
YSKLTVDKSRWQQGNVFSCSVMHEALHNHYTQKSLSLSPG Complete Heavy Chain Nucleic Acid Sequences D11-S17Y IgG2 HC
(SEQ ID NO: 43)
CAGGTGCAGCTGGTGCAGTCTGGGGCTGAGGTGAAGAAGCCTGGGTCCTC
GGTGAAGGTCTCCTGCAAGGCTTCTGGCTACACCTTCACAAGTAGGTATA
TACACTGGGTGCGACAGGCCCCTGGACAAGGGCTTGAGTGGATGGGATGG
ATTTATCCTGTAACTGGTGATACTTACTACAACGAGAAGTTCAAGGGCAG
AGTCACGATTACCGCGGACAAATCCACGAGCACAGCCTACATGGAGCTGA
GCAGCCTGAGATCTGAGGACACGGCCGTGTATTACTGTGCGAGAGGCTAT
GGGGCTTTTTACTACTGGGGCCAGGGCACCCTGGTCACCGTCTCCTCCGC
CTCCACCAAGGGCCCATCGGTCTTCCCGCTAGCGCCCTGCTCCAGGAGCA
CCTCCGAGAGCACAGCCGCCCTGGGCTGCCTGGTCAAGGACTACTTCCCC
GAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCG
TGGTGACCGTGCCCTCCAGCAACTTCGGCACCCAGACCTACACCTGCAAC
GTAGATCACAAGCCCAGCAACACCAAGGTGGACAAGACAGTTGAGCGCAA
ATGTTGTGTCGAGTGCCCACCGTGCCCAGCACCACCTGTGGCAGGACCGT
CAGTCTTCCTCTTCCCCCCAAAACCCAAGGACACCCTCATGATCTCCCGG
ACCCCTGAGGTCACGTGCGTGGTGGTGGACGTGAGCCACGAAGACCCCGA
GGTCCAGTTCAACTGGTACGTGGACGGCATGGAGGTGCATAATGCCAAGA
CAAAGCCACGGGAGGAGCAGTTCAACAGCACGTTCCGTGTGGTCAGCGTC
CTCACCGTCGTGCACCAGGACTGGCTGAACGGCAAGGAGTACAAGTGCAA
GGTCTCCAACAAAGGCCTCCCAGCCCCCATCGAGAAAACCATCTCCAAAA
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCTT
CTACCCCAGCGACATCGCCGTGGAGTGGGAGAGCAATGGGCAGCCGGAGA
ACAACTACAAGACCACACCTCCCATGCTGGACTCCGACGGCTCCTTCTTC
CTCTACAGCAAGCTCACCGTGGACAAGAGCAGGTGGCAGCAGGGGAACGT
CTTCTCATGCTCCGTGATGCATGAGGCTCTGCACAACCACTACACACAGA
AGAGCCTCTCCCTGTCTCCGGGT D11-8B8 IgG2 HC
(SEQ ID NO: 44)
CAGGTGCAGCTGGTGCAGTCTGGGGCTGAGGTGAAGAAGCCTGGGTCCTC
GGTGAAGGTCTCCTGCAAGGCTTCTGGCTACACCTTCACAAGTAGGTATA
TACACTGGGTGCGACAGGCCCCTGGACAAGGGCTTGAGTGGATGGGATGG
ATTTATCCTGTAACTGGTGATACTTACTACATCGAGAAGTTCAAGGGCAG
AGTCACGATTACCGCGGACAAATCCACGAGCACAGCCTACATGGAGCTGA
GCAGCCTGAGATCTGAGGACACGGCCGTGTATTACTGTGCGAGAGGCTAT
GGTGCTTTTTTCTACTGGGGCCAGGGCACCCTGGTCACCGTCTCCTCCGC
CTCCACCAAGGGCCCATCGGTCTTCCCGCTAGCGCCCTGCTCCAGGAGCA
CCTCCGAGAGCACAGCCGCCCTGGGCTGCCTGGTCAAGGACTACTTCCCC
GAACCGGTGACGGTGTCGTGGAACTCAGGCGCCCTGACCAGCGGCGTGCA -continued

```
CACCTTCCCGGCTGTCCTACAGTCCTCAGGACTCTACTCCCTCAGCAGCG
TGGTGACCGTGCCCTCCAGCAACTTCGGCACCCAGACCTACACCTGCAAC
GTAGATCACAAGCCCAGCAACACCAAGGTGGACAAGACAGTTGAGCGCAA
ATGTTGTGTCGAGTGCCCACCGTGCCCAGCACCACCTGTGGCAGGACCGT
CAGTCTTCCTCTTCCCCCCAAAACCCAAGGACACCCTCATGATCTCCGG
ACCCCTGAGGTCACGTGCGTGGTGGTGGACGTGAGCCACGAAGACCCCGA
GGTCCAGTTCAACTGGTACGTGGACGGCATGGAGGTGCATAATGCCAAGA
CAAAGCCACGGGAGGAGCAGTTCAACAGCACGTTCCGTGTGGTCAGCGTC
CTCACCGTCGTGCACCAGGACTGGCTGAACGGCAAGGAGTACAAGTGCAA
GGTCTCCAACAAAGGCCTCCCAGCCCCCATCGAGAAAACCATCTCCAAA
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCTT
CTACCCCAGCGACATCGCCGTGGAGTGGGAGAGCAATGGGCAGCCGGAGA
ACAACTACAAGACCACACCTCCCATGCTGGACTCCGACGGCTCCTTCTTC
CTCTACAGCAAGCTCACCGTGGACAAGAGCAGGTGGCAGCAGGGGAACGT
CTTCTCATGCTCCGTGATGCATGAGGCTCTGCACAACCACTACACACAGA
AGAGCCTCTCCCTGTCTCCGGGT
```

D11-C27G3 IgG2 HC (SEQ ID NO: 45)

```
CAGGTGCAGCTGGTGCAGTCTGGGGCTGAGGTGAAGAAGCCTGGGTCCTC
GGTGAAGGTCTCCTGCAAGGCTTCTGGCTACACCTTCACAAGTAGGTATA
TACACTGGGTGCGACAGGCCCCTGGACAAGGGCTTGAGTGGATGGGATGG
ATTTATCCTGTAACTGGTGATACTTACTACAGAGAGCCTTTCAAGGGCAG
AGTCACGATTACCGCGGACAAATCCACGAGCACAGCCTACATGGAGCTGA
GCAGCCTGAGATCTGAGGACACGGCCGTGTATTACTGTGCGAGAGGCTAC
GGAGCTTTTTACTACTGGGGCCAGGGCACCCTGGTCACCGTCTCCTCCGC
CTCCACCAAGGGCCCATCGGTCTTCCCGCTAGCGCCCTGCTCCAGGAGCA
CCTCCGAGAGCACAGCCGCCCTGGGCTGCCTGGTCAAGGACTACTTCCCC
GAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCG
TGGTGACCGTGCCCTCCAGCAACTTCGGCACCCAGACCTACACCTGCAAC
GTAGATCACAAGCCCAGCAACACCAAGGTGGACAAGACAGTTGAGCGCAA
ATGTTGTGTCGAGTGCCCACCGTGCCCAGCACCACCTGTGGCAGGACCGT
CAGTCTTCCTCTTCCCCCCAAAACCCAAGGACACCCTCATGATCTCCGG
ACCCCTGAGGTCACGTGCGTGGTGGTGGACGTGAGCCACGAAGACCCCGA
GGTCCAGTTCAACTGGTACGTGGACGGCATGGAGGTGCATAATGCCAAGA
CAAAGCCACGGGAGGAGCAGTTCAACAGCACGTTCCGTGTGGTCAGCGTC
CTCACCGTCGTGCACCAGGACTGGCTGAACGGCAAGGAGTACAAGTGCAA
GGTCTCCAACAAAGGCCTCCCAGCCCCCATCGAGAAAACCATCTCCAAA
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCTT
CTACCCCAGCGACATCGCCGTGGAGTGGGAGAGCAATGGGCAGCCGGAGA
ACAACTACAAGACCACACCTCCCATGCTGGACTCCGACGGCTCCTTCTTC
CTCTACAGCAAGCTCACCGTGGACAAGAGCAGGTGGCAGCAGGGGAACGT
CTTCTCATGCTCCGTGATGCATGAGGCTCTGCACAACCACTACACACAGA
AGAGCCTCTCCCTGTCTCCGGGT
```

C8-6 IgG4 HC (SEQ ID NO: 46)

```
CAGGTTCAGCTGGTGCAGTCTGGTGCTGAGGTGAAGAAGCCTGGTGCCTC
AGTGAAGGTCTCCTGCAAGGCTTCTGGTTACACCTTTACCGACTACTACA
TGCACTGGGTGCGTCAGGCCCCTGGTCAAGGTCTTGAGTGGATGGGTCGT
GTTAATCCTAACCGGGGTGGTACTACCTACAACCAGAAATTCGAGGGCCG
TGTCACCATGACCACAGACACATCCACGAGCACAGCCTACATGGAGCTGC
GTAGCCTGCGTTCTGACGACACGGCCGTGTATTACTGTGCGCGTACGAAC
TGGCTTGACTACTGGGGCCAGGGCACCACCGTCACCGTCTCCTCCGCCTC
CACCAAGGGCCCATCGGTCTTCCCGCTAGCGCCCTGCTCCAGGAGCACCT
CCGAGAGCACAGCCGCCCTGGGCTGCCTGGTCAAGGACTACTTCCCCGAA
CCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGG
TGACCGTGCCCTCCAGCAGCTTGGGCACGAAGACCTACACCTGCAACGTA
GATCACAAGCCCAGCAACACCAAGGTGGACAAGAGAGTTGAGTCCAAATA
TGGTCCCCCATGCCCACCCTGCCCAGCACCTGAGGCCGCCGGGGGACCAT
CAGTCTTCCTGTTCCCCCCAAAACCCAAGGACACTCTCATGATCTCCGG
ACCCCTGAGGTCACGTGCGTGGTGGTGGACGTGAGCCAGGAAGACCCCGA
GGTCCAGTTCAACTGGTACGTGGATGGCGTGGAGGTGCATAATGCCAAGA
CAAAGCCGCGGGAGGAGCAGTTCAACAGCACGTACCGTGTGGTCAGCGTC
CTCACCGTCCTGCACCAGGACTGGCTGAACGGCAAGGAGTACAAGTGCAA
GGTCTCCAACAAAGGCCTCCCGTCCTCCATCGAGAAAACCATCTCCAAAG
CCAAAGGGCAGCCCCGAGAGCCACAGGTGTACACCCTGCCCCCATCCCAG
GAGGAGATGACCAAGAACCAGGTCAGCCTGACCTGCCTGGTCAAAGGCTT
CTACCCCAGCGACATCGCCGTGGAGTGGGAAAGCAATGGGCAGCCGGAGA
ACAACTACAAGACCACGCCTCCCGTGCTGGACTCCGACGGCTCCTTCTTC
CTCTACAGCAGGCTAACCGTGGACAAGAGCAGGTGGCAGGAGGGGAATGT
CTTCTCATGCTCCGTGATGCATGAGGCTCTGCACAACCACTACACACAGA
AGAGCCTCTCCCTGTCTCTGGGT
```

C8-H241 IgG4 HC (SEQ ID NO: 47)

```
CAGGTTCAGCTGGTGCAGTCTGGTGCTGAGGTGAAGAAGCCTGGTGCCTC
AGTGAAGGTCTCCTGCAAGGCTTCTGGTTACACATTCACTGACTACTACA
TGCACTGGGTGCGTCAGGCCCCTGGTCAAGGTCTTGAGTGGATGGGTCGT
GTTAATCCTAACCGGAGGGGTACTACCTACAACCAGAAATTCGAGGGCCG
TGTCACCATGACCACAGACACATCCACGAGCACAGCCTACATGGAGCTGC
GTAGCCTGCGTTCTGACGACACGGCCGTGTATTACTGTGCGCGTGCGAAC
TGGCTTGACTACTGGGGCCAGGGCACCACCGTCACCGTCTCCTCCGCCTC
```

```
CACCAAGGGCCCATCGGTCTTCCCGCTAGCGCCCTGCTCCAGGAGCACCT
CCGAGAGCACAGCCGCCCTGGGCTGCCTGGTCAAGGACTACTTCCCCGAA
CCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGG
TGACCGTGCCCTCCAGCAGCTTGGGCACGAAGACCTACACCTGCAACGTA
GATCACAAGCCCAGCAACACCAAGGTGGACAAGAGAGTTGAGTCCAAATA
TGGTCCCCCATGCCCACCCTGCCCAGCACCTGAGGCCGCCGGGGGACCAT
CAGTCTTCCTGTTCCCCCCAAAACCCAAGGACACTCTCATGATCTCCCGG
ACCCCTGAGGTCACGTGCGTGGTGGTGGACGTGAGCCAGGAAGACCCCGA
GGTCCAGTTCAACTGGTACGTGGATGGCGTGGAGGTGCATAATGCCAAGA
CAAAGCCGCGGGAGGAGCAGTTCAACAGCACGTACCGTGTGGTCAGCGTC
CTCACCGTCCTGCACCAGGACTGGCTGAACGGCAAGGAGTACAAGTGCAA
GGTCTCCAACAAAGGCCTCCCGTCCTCCATCGAGAAAACCATCTCCAAAG
CCAAAGGGCAGCCCCGAGAGCCACAGGTGTACACCCTGCCCCCATCCCAG
GAGGAGATGACCAAGAACCAGGTCAGCCTGACCTGCCTGGTCAAAGGCTT
CTACCCCAGCGACATCGCCGTGGAGTGGGAAAGCAATGGGCAGCCGGAGA
ACAACTACAAGACCACGCCTCCCGTGCTGGACTCCGACGGCTCCTTCTTC
CTCTACAGCAGGCTAACCGTGGACAAGAGCAGGTGGCAGGAGGGGAATGT
CTTCTCATGCTCCGTGATGCATGAGGCTCTGCACAACCACTACACACAGA
AGAGCCTCTCCCTGTCTCTGGGT
```

C8-co16 IgG4 HC (SEQ ID NO: 48)
```
CAGGTTCAGCTGGTGCAGTCTGGTGCTGAGGTGAAGAAGCCTGGTGCCTC
AGTGAAGGTCTCCTGCAAGGCTTCTGGTTACACATTCACTGACTACTACA
TGCACTGGGTGCGTCAGGCCCCTGGTCAAGGTCTTGAGTGGATGGGTCGT
GTTAATCCTTATCGGGGTAGTACTACCTACAACCAGAAATTCGAGGGCCG
TGTCACCATGACCACAGACACATCCACGAGCACAGCCTACATGGAGCTGC
GTAGCCTGCGTTCTGACGACACGGCCGTGTATTACTGTGCGCGTGCGAAC
ATTCTTGACTACTGGGGCCAGGGCACCACCGTCACCGTCTCCTCCGCCTC
CACCAAGGGCCCATCGGTCTTCCCGCTAGCGCCCTGCTCCAGGAGCACCT
CCGAGAGCACAGCCGCCCTGGGCTGCCTGGTCAAGGACTACTTCCCCGAA
CCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGG
TGACCGTGCCCTCCAGCAGCTTGGGCACGAAGACCTACACCTGCAACGTA
GATCACAAGCCCAGCAACACCAAGGTGGACAAGAGAGTTGAGTCCAAATA
TGGTCCCCCATGCCCACCCTGCCCAGCACCTGAGGCCGCCGGGGGACCAT
CAGTCTTCCTGTTCCCCCCAAAACCCAAGGACACTCTCATGATCTCCCGG
ACCCCTGAGGTCACGTGCGTGGTGGTGGACGTGAGCCAGGAAGACCCCGA
GGTCCAGTTCAACTGGTACGTGGATGGCGTGGAGGTGCATAATGCCAAGA
CAAAGCCGCGGGAGGAGCAGTTCAACAGCACGTACCGTGTGGTCAGCGTC
CTCACCGTCCTGCACCAGGACTGGCTGAACGGCAAGGAGTACAAGTGCAA
GGTCTCCAACAAAGGCCTCCCGTCCTCCATCGAGAAAACCATCTCCAAAG
CCAAAGGGCAGCCCCGAGAGCCACAGGTGTACACCCTGCCCCCATCCCAG
GAGGAGATGACCAAGAACCAGGTCAGCCTGACCTGCCTGGTCAAAGGCTT
CTACCCCAGCGACATCGCCGTGGAGTGGGAAAGCAATGGGCAGCCGGAGA
ACAACTACAAGACCACGCCTCCCGTGCTGGACTCCGACGGCTCCTTCTTC
CTCTACAGCAGGCTAACCGTGGACAAGAGCAGGTGGCAGGAGGGGAATGT
CTTCTCATGCTCCGTGATGCATGAGGCTCTGCACAACCACTACACACAGA
AGAGCCTCTCCCTGTCTCTGGGT
```

Human cMet-ECD-Fc-Flis (SEQ ID NO: 72)
_MKAPAVLAPGILVLLFTLVQRSNG_ECKEALAKSEMNVNMKYQLPNFTAET
PIQNVILHEHHIFLGATNYIYVLNEEDLQKVAEYKTGPVLEHPDCFPCQD
CSSKANLSGGVWKDNINMALVVDTYYDDQLISCGSVNRGTCQRHVFPHNH
TADIQSEVHCIFSPQIEEPSQCPDCVVSALGAKVLSSVKDRFINFFVGNT
INSSYFPDHPLHSISVRRLKETKDGFMFLTDQSYIDVLPEFRDSYPIKYV
HAFESNNFIYFLTVQRETLDAQTFHTRIIRFCSINSGLHSYMEMPLECIL
TEKRKKRSTKKEVFNILQAAYVSKPGAQLARQIGASLNDDILFGVFAQSK
PDSAEPMDRSAMCAFPIKYVNDFFNKIVNKNNVRCLQHFYGPNHEHCFNR
TLLRNSSGCEARRDEYRTEFTTALQRVDLFMGQFSEVLLTSISTFIKGDL
TIANLGTSEGRFMQVVVSRSGPSTPHVNFLLDSHPVSPEVIVEHTLNQNG
YTLVITGKKITKIPLNGLGCRHFQSCSQCLSAPPFVQCGWCHDKCVRSEE
CLSGTWTQQICLPAIYKVFPNSAPLEGGTRLTICGWDFGFRRNNKFDLKK
TRVLLGNESCTLTLSESTMNTLKCTVGPAMNKHFNMSIIISNGHGTTQYS
TFSYVDPVITSISPKYGPMAGGTLLTLTGNYLNSGNSRHISIGGKTCTLK
SVSNSILECYTPAQTISTEFAVKLKIDLANRETSIFSYREDPIVYEIHPT
KSFISGGSTITGVGKNLNSVSVPRMVINVHEAGRNFTVACQHRSNSEIIC
CTTPSLQQLNLQLPLKTKAFFMLDGILSKYFDLIYVHNPVFKPFEKPVMI
SMGNENVLEIKGNDIDPEAVKGEVLKVGNKSCENIHLHSEAVLCTVPNDL
LKLNSELNIEWKQAISSTVLGKVIVQPDQNFTLEVLFQGPDIEPKSCDKT
HTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKV
SNKALPAPIEKTISKAKGQPREPQEYTLPPSREEMTKNQVSLTCLVKGFY
PSDIAVEWESNGQPENNYKTTPPVLDSDGSFFLYSKLTVDKSRWQQGNVF
SCSVMHEALHNHYTQKSLSLSPGKRIDYKDDDDKHVHHHHHH

Bold, italicized amino acids represent the signal sequence; bold underlined amino acids represent the Flis tag.

Cynomolgus Monkey cMet-ECD-Fc-Flis (SEQ ID NO: 73)
_MKAPAVLVPGILVLLFTLVQRSNG_ECKEALAKSEMNVNMKYQLPNFTAET
AIQNVILHEHHIFLGATNYIYVLNEEDLQKVAEYKTGPVLEHPDCFPCQD
CSSKANLSGGVWKDNINMALVVDTYYDDQLISCGSVNRGTCQRHVFPHNH
TADIQSEVHCIFSPQIEEPNQCPDCVVSALGAKVLSSVKDRFINFFVGNT
INSSYFPHHPLHSISVRRLKETKDGFMFLTDQSYIDVLPEFRDSYPIKYI -continued HAFESNNFIYFLTVQRETLNAQTFHTRIIRFCSLNSGLHSYMEMPLECIL
TEKRKKRSTKKEVFNILQAAYVSKPGAQLARQIGASLNDDILFGVFAQSK
PDSAEPMDRSAMCAFPIKYVNDFFNKIVNKNNVRCLQHFYGPNHEHCFNR
TLLRNSSGCEARRDEYRAEFTTALQRVDLFMGQFSEVLLTSISTFVKGDL
TIANLGTSEGRFMQVVVSRSGPSTPHVNFLLDSHPVSPEVIVEHPLNQNG
YTLVVTGKKITKIPLNGLGCRHFQSCSQCLSAPPFVQCGWCHDKCVRSEE
CPSGTWTQQICLPAIYKVFPTSAPLEGGTRLTICGWDFGFRRNNKFDLKK
TRVLLGNESCTLTLSESTMNTLKCTVGPAMNKHFNMSIIISNGHGTTQYS
TFSYVDPIITSISPKYGPMAGGTLLTLTGNYLNSGNSRHISIGGKTCTLK
SVSNSILECYTPAQTISTEFAVKLKIDLANRETSIFSYREDPIVYEIHPT
KSFISGGSTITGVGKNLHSVSVPRMVINVHEAGRNFTVACQHRSNSEIIC
CTTPSLQQLNLQLPLKTKAFFMLDGILSKYFDLIYVHNPVFKPFEKPVMI
SMGNENVLEIKGNDIDPEAVKGEVLKVGNKSCENIHLHSEAVLCTVPNDL
LKLNSELNIEWKQAISSTVLGKVIVQPDQNFTLEVLFQGPDIEPKSCDKT
HTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKV
SNKALPAPIEKTISKAKGQPREPQEYTLPPSREEMTKNQVSLTCLVKGFY
PSDIAVEWESNGQPENNYKTTPPVLDSDGSFFLYSKLTVDKSRWQQGNVF
SCSVMHEALHNHYTQKSLSLSPGKRIDYKDDDDKHVHHHHHH

Bold, italicized amino acids represent the signal sequence; bold underlined amino acids represent the Flis tag.

Rat cMet-ECD-Fc-Flis
(SEQ ID NO: 74)
*MKAPTALAPGILLLLLTLAQRSHG*ECKEALVKSEMNVNMKYQLPNFTAET
PIHNVVLHGHHIYLGATNYIYVLNDKDLQKVSEFKTGPVVEHPDCFPCQD
CSSKANVSGGVWKDNVNMALLVDTYYDDQLISCGSVNRGTCQRHVLPPDN
AADIQSEVHCMFSPLAEEESGQCPDCVVSALGAKVLLSEKDRFINFFVGN
TINSSYPPDYSLHSISVRRLKETQDGFKFLTDQSYIDVLPEFRDSYPIKY
IHAFESNHFIYFLTVQKETLDAQTFHTRIIRFCSVDSGLHSYMEMPLECI
LTEKRRKRSTREEVFNILQAAYVSKPGANLAKQIGASPYDDILYGVFAQS
KPDSAEPMNRSAVCAFPIKYVNDFFNKIVNKNNVRCLQHFYGPNHEHCFN
RTLLRNSSGCEVRSDEYRTEFTTALQRVDLFMGRLNHVLLTSISTFIKGD
LTIANLGTSEGRFMQVVLSRTAHFTPHVNFLLDSYPVSPEVIVEHPSNQN
GYTLVVTGKKITKIPLNGLGCGHFQSCSQCLSAPYFIQCGWCHNRCVHSN
ECPSGTWTQEICLPAVYKVFPTSAPLEGGTMLTICGWDFGFKKNNKFDLR
KTKVLLGNESCTLTLSESTTNTLKCTVGPAMSEHFNVSVIVSNSRETTQY
SAFSYVDPVITSISPRYGPHAGGTLLTLTGKYLNSGNSRHISIGGKTCTL
KSVSDSILECYTPGHTVSAEFPVKLKIDLADRVTSSFSYREDPVVSEIHP
TKSFISGGSTITGIGKNLNSVSTPKLVIEVHDVGVNYTVACQHRSSSEII
CCTTPSLQQLDLQLPLKTKAFFLLDGILSKHFDLTYVHDPMFKPFEKPVM
ISMGNENVVEIKGDDIDPEAVKGEVLKVGNKSCENLHWHSEALLCTVPSD LLKLNGGELNIEWKQAVSSTVLGKVIVQPDQNFALEVLFQGPDIEPKSCD
KTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKC
KVSNKALPAPIEKTISKAKGQPREPQEYTLPPSREEMTKNQVSLTCLVKG
FYPSDIAVEWESNGQPENNYKTTPPVLDSDGSFFLYSKLTVDKSRWQQGN
VFSCSVMHEALHNHYTQKSLSLSPGKRIDYKDDDDKHVHHHHHH

Bold, italicized amino acids represent the signal sequence; bold underlined amino acids represent the Flis tag.

Human c-Met ECD
(SEQ ID NO: 75)
*MKAPAVLAPGILVLLFTLVQRSNG*ECKEALAKSEMNVNMKYQLPNFTAET
PIQNVILHEHHIFLGATNYIYVLNEEDLQKVAEYKTGPVLEHPDCFPCQD
CSSKANLSGGVWKDNINMALVVDTYYDDQLISCGSVNRGTCQRHVFPHNH
TADIQSEVHCIFSPQIEEPSQCPDCVVSALGAKVLSSVKDRFINFFVGNT
INSSYFPDHPLHSISVRRLKETKDGFMFLTDQSYIDVLPEFRDSYPIKYV
HAFESNNFIYFLTVQRETLDAQTFHTRIIRFCSINSGLHSYMEMPLECIL
TEKRKKRSTKKEVFNILQAAYVSKPGAQLARQIGASLNDDILFGVFAQSK
PDSAEPMDRSAMCAFPIKYVNDFFNKIVNKNNVRCLQHFYGPNHEHCFNR
TLLRNSSGCEARRDEYRTEFTTALQRVDLFMGQFSEVLLTSISTFIKGDL
TIANLGTSEGRFMQVVVSRSGPSTPHVNFLLDSHPVSPEVIVEHTLNQNG
YTLVITGKKITKIPLNGLGCRHFQSCSQCLSAPPFVQCGWCHDKCVRSEE
CLSGTWTQQICLPAIYKVFPNSAPLEGGTRLTICGWDFGFRRNNKFDLKK
TRVLLGNESCTLTLSESTMNTLKCTVGPAMNKHFNMSIIISNGHGTTQYS
TFSYVDPVITSISPKYGPMAGGTLLTLTGNYLNSGNSRHISIGGKTCTLK
SVSNSILECYTPAQTISTEFAVKLKIDLANRETSIFSYREDPTVYEIHPT
KSFISGGSTITGVGKNLNSVSVPRMVINVHEAGRNFTVACQHRSNSEIIC
CTTPSLQQLNLQLPLKTKAFFMLDGILSKYFDLIYVHNPVFKPFEKPVMI
SMGNENVLEIKGNDIDPEAVKGEVLKVGNKSCENIHLHSEAVLCTVPNDL
LKLNSELNIEWKQAISSTVLGKVIVQPDQNFT Bold, italicized amino acids represent the signal sequence.

Human c-Met Sema Domain with Flis tag
(SEQ ID NO: 76)
*MKAPAVLAPGILVLLFTLVQRSNG*ECKEALAKSEMNVNMKYQLPNFTAET
PIQNVILHEHHIFLGATNYIYVLNEEDLQKVAEYKTGPVLEHPDCFPCQD
CSSKANLSGGVWKDNINMALVVDTYYDDQLISCGSVNRGTCQRHVFPFTN
HTADIQSEVHCIFSPQIEEPSQCPDCVVSALGAKVLSSVKDRFINFFVGN
TINSSYFPDHPLHSISVRRLKETKDGFMFLTDQSYIDVLPEFRDSYPIKY
VHAFESNNFIYFLTVQRETLDAQTFHTRIIRFCSINSGLHSYMEMPLECI
LTEKRKKRSTKKEVFNILQAAYVSKPGAQLARQIGASLNDDILFGVFAQS
KPDSAEPMDRSAMCAFPIKYVNDFFNKIVNKNNVRCLQHFYGPNHEHCFN
RTLLRNSSGCEARRDEYRTEFTTALQRVDLFMGQFSEVLLTSISTFIKGD -continued

LTIANLGTSEGRFMQVVVSRSGPSTPHVNFLLDSHPVSPEVIVEHTLNQN

GYTLVITGKKITKIPLNGLGCRHFQSCSQCLSAPPFVQCGWCHDKCVRSE

ECLSGTWTQQICLDYKDDDDKHVHHHHHH

Bold, italicized amino acids represent the signal sequence; bold underlined amino acids represent the Flis tag

```
C8- Antibody Epitopes in the Human c-Met
Extracellular Domain
121VVDTYYDDQL130                   (SEQ ID NO: 77)
131ISCGSVNRGTCQRHVFPHNHTADIQS156   (SEQ ID NO: 78)
179ALGAKVLSSVKDRFINF195            (SEQ ID NO: 79)
216VRRLKETKDGFM227                 (SEQ ID NO: 80)
123DTYYDD128                       (SEQ ID NO: 81)
144HVFPHNHTADIQS156                (SEQ ID NO: 82)
192FINF195                         (SEQ ID NO: 83)
220KETKDGFM227                     (SEQ ID NO: 84)

D11- Antibody Epitopes in the Human c-Met
Extracellular Domain
84YKTGPVLEHPDCFPCQDCSSKANL95       (SEQ ID NO: 85)
95CFPCQDCSSKA105                   (SEQ ID NO: 86)
```

Consensus CDR Sequences

```
D11- Antibody Light Chain CDR2
GTSX1LX2S,                         (SEQ ID NO: 87)
``` wherein $X_1$ is Y or R, and $X_2$ is A or R;

```
C8- Antibody Light Chain CDR1
SVSSSVX3SIYLH,                     (SEQ ID NO: 88)
``` wherein $X_3$ is S or R;

```
C8- Antibody Light Chain CDR3
X4X5YX6GYPLT,                      (SEQ ID NO: 89)
``` wherein $X_4$ is I or Q, $X_5$ is Q or V, and $X_6$ is S or R;

```
D11- Heavy Chain Antibody CDR2
WIYPVTGDTYYX7EX8FKG,               (SEQ ID NO: 90)
``` wherein $X_2$ is N, I, or R, and $X_8$ is K or P;

```
D11- Antibody Heavy Chain CDR 3
GYGAFX9Y,                          (SEQ ID NO: 91)
``` wherein $X_9$ is Y or F;

```
C8- Antibody Heavy Chain CDR 2
RVNPX10RX11X12TTYNQKFEG,           (SEQ ID NO: 92)
``` wherein $X_{10}$ is N or Y, $X_{11}$ is G or R, and $X_{12}$ is G or S;

```
C8- Antibody Heavy Chain CDR3
X13NX14LDY,                        (SEQ ID NO: 93)
``` wherein $X_{13}$ is T or A, and $X_{14}$ is W or I;

Consensus Light Chain Variable Region Sequences

```
D11- Antibody Light Chain Variable Region
Consensus Sequence
                                   (SEQ ID NO: 94)
EIVLTQSPGTLSLSPGERATLSCSVSSSISSTNLHWYQQKPGQAPRLLIY

GTSX1LX2SGIPDRFSGSGSGTDFTLTISRLEPEDFAVYYCQQWSSYPYS

FGQGTKLEIK
``` wherein $X_1$ is Y or R, and $X_2$ is A or R;

```
C8- Antibody Light Chain Variable Region
Consensus Sequence
                                   (SEQ ID NO: 95)
DIQMTQSPSSLSASVGDRVTITCSVSSSVX3SIYLHWYQQKPGKAPKLLI

YSTSNLASGVPSRFSGSGSGTDFTLTISSLQPEDFATYYCX4X5YX6GYP

LTFGGGTKVEIK
``` wherein $X_3$ is S or R, $X_4$ is I or Q, $X_5$ is Q, or V, and $X_6$ is S or R;

Consensus Heavy Chain Variable Region Sequences

```
D11- Antibody Heavy Chain Variable Region
Consensus Sequence
                                   (SEQ ID NO: 96)
QVQLVQSGAEVKKPGSSVKVSCKASGYTFTSRYIHWVRQAPGQGLEWMGW

IYPVTGDTYYX7EX8FKGRVTITADKSTSTAYMELSSLRSEDTAVYYCAR

GYGAFX9YWGQGTLVTVS
``` wherein $X_7$ is N, I, or R, $X_8$ is K or P, and $X_9$ is Y or F;

```
C8- Antibody Heavy Chain Variable Region
Consensus Sequence
                                   (SEQ ID NO: 97)
QVQLVQSGAEVKKPGASVKVSCKASGYTFTDYYMHWVRQAPGQGLEWMGR

VNPX10RX11X12TTYNQKFEGRVTMTTDTSTSTAYMELRSLRSDDTAVY

YCARX13NX14LDYWGQGTTVTVS
``` wherein $X_{10}$ is Y or N, $X_{11}$ is G or R, $X_{12}$ is S or G, $X_{13}$ is A or T, and $X_{14}$ is I or W.

---

We claim:

1. A purified monoclonal antibody, or antigen-binding fragment thereof, that binds human c-Met, comprising three light chain complementarity determining regions (LCDRs) and three heavy chain complementarity determining regions (HCDRs), wherein said three LCDRs and said three HCDRs are a LCDR1 comprising the amino acid sequence SVSSS-VSSIYLH (SEQ ID NO: 53), a LCDR2 comprising the amino acid sequence STSNLAS (SEQ ID NO: 54), a LCDR3 comprising the amino acid sequence IQYSGYPLT (SEQ ID NO: 55), a HCDR1 comprising the amino acid sequence GYTFT-DYYMH (SEQ ID NO: 65), a HCDR2 comprising the amino acid sequence RVNPNRGGTTYNQKFEG (SEQ ID NO: 66), and a HCDR3 comprising the amino acid sequence TNWLDY (SEQ ID NO: 67).

2. A purified monoclonal antibody, or antigen-binding fragment thereof, that binds human c-Met, comprising three light chain complementarity determining regions (LCDRs) and three heavy chain complementarity determining regions (HCDRs), wherein said three LCDRs and said three HCDRs are a LCDR1 comprising the amino acid sequence SVSSS-VSSIYLH (SEQ ID NO: 53), a LCDR2 comprising the amino acid sequence STSNLAS (SEQ ID NO: 54), a LCDR3 comprising the amino acid sequence QVYSGYPLT (SEQ ID NO: 56), a HCDR1 comprising the amino acid sequence GYTFT-DYYMH (SEQ ID NO: 65), a HCDR2 comprising the amino acid sequence RVNPNRRGTTYNQKFEG (SEQ ID NO: 68), and a HCDR3 comprising the amino acid sequence ANWLDY (SEQ ID NO: 69).

3. The monoclonal antibody, or antigen-binding fragment thereof, of claim 1, which comprises a light chain variable region (LCVR) and a heavy chain variable region (HCVR), wherein the LCVR comprises the amino acid sequence of SEQ ID NO: 4 and the HCVR comprises the amino acid sequence of SEQ ID NO: 16.

4. The monoclonal antibody, or antigen-binding fragment thereof, of claim 2, which comprises a light chain variable region (LCVR) and a heavy chain variable region (HCVR), wherein the LCVR comprises the amino acid sequence of SEQ ID NO: 5 and the HCVR comprises the amino acid sequence of SEQ ID NO: 17.

5. The monoclonal antibody of claim 3, wherein said antibody comprises a light chain having the amino acid sequence of SEQ ID NO: 28 and a heavy chain having the amino acid sequence of SEQ ID NO: 40.

6. The monoclonal antibody of claim 4, comprising a light chain having the amino acid sequence of SEQ ID NO: 29 and a heavy chain having the amino acid sequence of SEQ ID NO: 41.

7. The monoclonal antibody of claim 5, comprising two light chains having the amino acid sequence of SEQ ID NO: 28 and two heavy chains having the amino acid sequence of SEQ ID NO: 40.

8. The monoclonal antibody of claim 6, comprising two light chains having the amino acid sequence of SEQ ID NO: 29 and two heavy chains having the amino acid sequence of SEQ ID NO: 41.

9. A pharmaceutical composition, comprising the monoclonal antibody, or antigen-binding fragment thereof, of claim 1, and a pharmaceutically acceptable carrier, diluent, or excipient.

10. A pharmaceutical composition, comprising the monoclonal antibody, or antigen-binding fragment thereof, of claim 2, and a pharmaceutically acceptable carrier, diluent, or excipient.

11. A pharmaceutical composition, comprising the monoclonal antibody of claim 7, and a pharmaceutically acceptable carrier, diluent, or excipient.

12. A pharmaceutical composition, comprising the monoclonal antibody of claim 8, and a pharmaceutically acceptable carrier, diluent, or excipient.

13. The monoclonal antibody, or antigen-binding fragment thereof, of claim 2, wherein said antibody comprises a light chain having the amino acid sequence of SEQ ID NO: 29 and a heavy chain having an IgG4 heavy chain constant region.

14. The monoclonal antibody, or antigen-binding fragment thereof, of claim 4, wherein said antibody comprises a light chain having the amino acid sequence of SEQ ID NO: 29 and a heavy chain having an IgG4 heavy chain constant region.

15. The monoclonal antibody, or antigen-binding fragment thereof, of claim 14, wherein the amino acid sequence of said light chain is encoded by SEQ ID NO: 35, and the amino acid sequence of said heavy chain is encoded by SEQ ID NO: 47.

16. The monoclonal antibody of claim 15, wherein the antibody comprises two light chains and two heavy chains and wherein the amino acid sequence of said light chains is encoded by SEQ ID NO: 35, and the amino acid sequence of said heavy chains is by SEQ ID NO: 47.

17. A pharmaceutical composition, comprising the monoclonal antibody, or antigen-binding fragment thereof, of claim 4, and a pharmaceutically acceptable carrier, diluent, or excipient.

18. A pharmaceutical composition, comprising the monoclonal antibody, or antigen-binding fragment thereof, of claim 15, and a pharmaceutically acceptable carrier, diluent, or excipient.

19. A pharmaceutical composition, comprising the monoclonal antibody of claim 16, and a pharmaceutically acceptable carrier, diluent, or excipient.

\* \* \* \* \*